United States Patent
Thompson et al.

(10) Patent No.: US 11,083,732 B2
(45) Date of Patent: Aug. 10, 2021

(54) USE OF NEGATIVE MODULATORS OF GABA RECEPTORS CONTAINING ALPHA5 SUBUNITS AS FAST ACTING ANTIDEPRESSANTS

(71) Applicant: University of Maryland, Baltimore, Baltimore, MD (US)

(72) Inventors: Scott Thompson, Baltimore, MD (US); Mark D. Kvarta, Ellicott City, MD (US); Adam Van Dyke, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 240 days.

(21) Appl. No.: 15/300,984

(22) PCT Filed: Mar. 31, 2015

(86) PCT No.: PCT/US2015/023667
§ 371 (c)(1),
(2) Date: Sep. 30, 2016

(87) PCT Pub. No.: WO2015/153658
PCT Pub. Date: Oct. 8, 2015

(65) Prior Publication Data
US 2017/0020892 A1    Jan. 26, 2017

Related U.S. Application Data

(60) Provisional application No. 61/972,446, filed on Mar. 31, 2014.

(51) Int. Cl.
*A61K 31/5517* (2006.01)
*A61K 31/53* (2006.01)
(Continued)

(52) U.S. Cl.
CPC ...... *A61K 31/5517* (2013.01); *A61K 31/4375* (2013.01); *A61K 31/455* (2013.01); *A61K 31/53* (2013.01); *A61K 45/06* (2013.01)

(58) Field of Classification Search
CPC ............ A61P 25/24; A61P 25/22; A61P 25/00
See application file for complete search history.

(56) References Cited

U.S. PATENT DOCUMENTS

2011/0086828 A1    4/2011   Winsauer

OTHER PUBLICATIONS

Jones, Pharmacokinetics and metabolism studies on (3-tert-butyl-7-(5-methylisoxazol-3-yl)-2-(1-methyl-1H-1,2,4-triazol-5-ylmethoxy) pyrazolo[1,5-d][1,2,4]triazine, a functionally selective GABAA α5 inverse agonist for cognitive dysfunction, Bioorganic & Medicinal Chemistry Letters, 2006, 16, pp. 872-875.*

(Continued)

*Primary Examiner* — Savitha M Rao
*Assistant Examiner* — Andrew P Lee
(74) *Attorney, Agent, or Firm* — Norton Rose Fulbright US LLP

(57) ABSTRACT

Embodiments of the disclosure include methods and compositions related to treatment of one or more medical conditions with one or more negative modulators of $GABA_A$ receptors. In specific embodiments, depression and/or suicidality is treated or ameliorated or prevented with one or more negative modulators of $GABA_A$ receptors, such as a partial inverse agonist of a $GABA_A$ receptor comprising an alpha5 subunit.

11 Claims, 12 Drawing Sheets

(51) Int. Cl.
    A61K 45/06    (2006.01)
    A61K 31/455   (2006.01)
    A61K 31/4375  (2006.01)

(56) References Cited

OTHER PUBLICATIONS

Mohler, The GABA system in anxiety and depression and its therapeutic potential, Neuropharmacology, 2012, 62, pp. 42-53.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Smalley, Evidence that the dopamine D4 receptor is a susceptibility gene in attention deficit hyperactivity disorder, Molecular Psychiatry, 1998, 3, pp. 427-430.*
Amat et al., "Behavioral Control Over Shock Blocks Behavioral and Neurochemical Effects of Later Social Defeat," Neuroscience 2010; 165(4): 1031-1038.
Atack et al., "In vivo labelling of α5 subunit-containing $GABA_A$ receptors using the selective radioligand [$^3$H]L-655,708," Neuropharmacology, 2005; 49: 220-229.
Atack et al., "L-655,708 enhances cognition in rats but is not proconvulsant at a selective for α5-containing $GABA_A$ receptors," Neuropharmacology, 2006; 51: 1023-1029.
Atack et al., "In vitro and in vivo properties of 3-tert-Butyl-7-(5-methylisoxazol-3-yl)-2-(1-methyl-1H-1,2,4-triazol-5-ylmethoxyl)-pyrazolo[1,5-d]-[1,2,4]triazine (MRK-016), a $GABA_A$ receptor α5 subtype-selective inverse agonist," Journal of Pharmacology and Experimental Therapeutics, 2009; 331(2): 470-484.
Ballard et al., "RO4938581, a novel cognitive enhancer acting at $GABA_A$ α5 subunit-containing receptors," Psychopharmacology, 2009; 202: 207-223.
Berman et al., "Antidepressant effects of ketamine in depressed patients," Society of Biological Psychiatry, 2000; 47: 351-354.
Burgard et al., "Properties of Recombinant γ-Aminobutyric $Acid_A$ Receptor Isoforms Containing the α5 Subunit Subtype," Molecular Pharmacology, 1996; 50: 119-127.
Cai et al., "Local potentiation of excitatory synapses by serotonin and its alteration in rodent models of depression," Nature Neuroscience, 2013; 16(4): 464-474.
Chen et al., "Structural model for γ-aminobutyric acid receptor noncompetitive antagonist binding: Widely diverse structures fit the same site," PNAS, 2006; 103(13): 5185-5190.
Collinson et al., "Enhanced Learning and Memory and Altered GABAergic Synaptic Transmission in Mice Lacking the α5 Subunit of the $GABA_A$ Receptor," The Journal of Neuroscience, 2002; 22(13): 5572-5580.
Fischell et al., "Rapid Antidepressant Action and Restoration of Excitatory Synaptic Strength After Chronic Stress by Negative Modulators of Alpha5-Containing $GABA_A$ Receptors," Neuropsychopharmacology, 2015; 1-11.
Fritschy et al., "$GABA_A$-Receptor Heterogeneity in the Adult Rat Brain: Differential Regional and Cellular Distribution of Seven Major Subunit," The Journal of Comparative Neurology, 1995; 359:154-194.
Ibrahim et al., "Course of Improvement in Depressive Symptoms to a Single Intravenous Infusion of Ketamine vs Add-on Riluzole: Results from a 4-Week, Double-Blind, Placebo-Controlled Study," Neruopsychopharmacology, 2012; 37: 1526-1533.
Kallarackal et al., "Chronic Stress Induces a Selective Decrease in AMPA Receptor-Mediated Synaptic Excitation at Hippocampal Temporoammonic-CA1 Synapses," The Journal of Neuroscience, 2013; 15669-15674.
Li et al., "Glutamate NMDA Receptor Antagonists Rapidly Reverse Behavioral and Synaptic Deficits Caused by Chronic Stress Exposure," Biol Psychiatry, 2011; 69(8): 754-761.

Machadi-Viera et al., "Ketamine and the Next Generation of Antidepressants with a Rapid Onset of Action," Pharmacol Ther., 2009; 123(2): 143-150.
Maeng et al., "Cellular Mechanisms Underlying the Antidepressant Effects of Ketamine: Role Acid Receptors of α-Amino-3-Hydroxy-5-Methylisoxazole-4-Propionic Acid Receptors," Biol. Psychiatry, 2008; 63: 349-352.
Mohler et al., "A New Benzodiazepine Pharmacology," Perspectives in Pharmacology, 300(1): 2-8.
Rudolph et al., "Benzodiazepine actions mediated by specific γ-aminobutyric $acid_A$ receptor subtypes," Nature, 1999; 401: 796-800.
Serwanski et al., "Synaptic and non-synaptic localization of $GABA_A$ receptors containing the α5 subunit in the rat brain," J. Comp. Neurol. 2006; 499(3): 458-470.
Shansky et al., "Estrogen mediates sex differences in stress-induced prefrontal cortex dysfunction," Molecular Psychiatry, 2004; 9: 531-538.
Sieghart, W. and G. Sperk, "Subunity Composition, Distribution and Fuction of $GABA_A$ Receptor Subtypes," Current Topics in Medicinal Chemistry, 2002; 2: 795-816.
Sieghart et al., "A novel $GABA_A$ receptor pharmacology: drugs interacting with the α$^+$γ$^-$ interface," British Journal of Pharmacology, 2012; 166: 476-485.
Wafford, Keith, "$GABA_A$ receptor subtypes: any clues to the mechanism of benzodiazepine dependence?" Current Opinion in Pharmacology, 2005; 5: 47-52.
Wainwright et al., "Expression of $GABA_A$ receptor α5 subunit-like immunoreactivity in human hippocampus," Molecular Brain Research, 2000; 80: 228-232.
Willner et al., "Reduction of sucrose preference by chronic unpredictable mild stress, and its restoration by a tricyclic antidepressant," Psychopharmacology, 1987; 93(3): 358-364.
Zarate Jr. et al., "A Randomized Trial of an N-methyl-D-aspartate Antagonist in Treatment-Resistant Major Depression," Arch Gen Psychiatry, 2006; 63: 856-864.
Zarate Jr. et al., "Replication of Ketamine's Antidepressant Efficacy in Bipolar Depression: A Randomized Controlled Add-on Trial," Biol Psychiatry, 2012; 71(11): 939-946.
Berton et al., "Essential role of BDNF in the mesolimbic dopamine pathway in social defeat stress," Science, 311(5762): 864-8, (2006).
LeGates et al., "Aberrant light directly impairs mood and learning through melanopsin-expressing neurons," Nature, 491(7425):594-598, (2012).
Will et al., "Selectively bred Wistar-Kyoto rats: an animal model of depression and hyper-responsiveness to antidepressants," Mol. Psychiatry, 8(11): 925-932, (2003).
Redrobe et al., "Negative modulation of GABAY 5 receptors by RO4938581 attenuates discrete sub-chronic and early postnatal phencyclidine (PCP)-induced cognitive deficits in rats", Psychopharmacology, Nov. 29, 2011, vol. 221, No. 3, pp. 451-468, Springer, Berlin, DE.
Lecker et al., "Potentiation of GABAA receptor activity by volatile anaesthetics is reduced by 5GABAA receptor-preferring inverse agonists", British Journal of Anaesthesia, vol. 110, No. S1, 2013,— 2013, pp. 173-181.
Gabriella Guerrini, et al; "Benzodiazepine Receptor Ligands: a Patent Review (2006-2012)"; Informa Healthcare; Expert Opin. There.Patents Downloaded from informahealthcare.com by University of Florence on Mar. 25, 2013.
John R. Atack; GABAA Receptor Subtype-Selective Modulators. I. A2/A3-Selective Agonists as Non-Sedating Anxiolytics; Department of Neuroscience, Janssen Pharmaceutical Research and Developmenatl Turnhoutseweg 30, Beerse, B-2340; Current Topics in Medicinal Chemistry, 2011, 11, 1176-1202-2011.
JM Fritschy, et al; GABAA Receptors and Plasticity of Inhibitory Neurotransmission in the Central Nervouse System; European Journal of Neourscience—ISSN 0953-816X—Stampa.—39:11 (2014) pp. 1845-1865.
John R. Atack; GABAA Receptor Subtype-Selective Modulators. II. a5-Selective InverseAgonists for Cognition Enhancement; Department of Neuroscience, Janssen Pharmaceutical Research and Devel-

(56) References Cited

OTHER PUBLICATIONS opment, Turnhoutseweg 30, Beerse, B-2340, Current Topics in Medicinal Chemistry, 2011, 11, 1203-1214.

Panos Zanos, et al; A Negative Allosteric Modulator for a5 Subunit-Containing GABA Receptors Exerts a Rapid and Persistent Antidepressant-Like Action without the Side Effects of the NMDA Receptor Antagonist Ketamine in Mice; Dept. of Psychiatry, University of Maryland School of Medicine; eNeuro; Jan./Feb. 2017, 4(1) e0285-16.2017 1-11.

Fischell J, Van Dyke AM, Kvarta MD, LeGates TA, Thompson SM. Rapid antidepressant action and restoration of excitatory synaptic strength after chronic stress by negative modulators of alpha5-containing GABA-A Receptors. Neuropsychopharmacology. 40: 2499-2509, 2015.

Xu NZ, Ernst M, Treven M, Cerne et al. Negative allosteric modulation of alpha 5-containing GABA(A) receptors engenders antidepressant-like effects and selectively prevents age-associated hyperactivity in tau-depositing mice. Psychopharmacology 235: 1151-1161, 2018.

David J. Nutt, et al: "Searching for Perfect Sleep: The Continuing Evolution of GABAA Receptor Modulators as Hypnotics": Journal of Phychopharmacology' 24(11) 1601-1612; 2010.

Samardzic et al., "Antidepressant Effects of an Inverse Agonist Selective for ?5 GABA-A Receptors in the Rat Forced Swim Test" Acta Veterinaria-Beograd 2014, 64 (1), 52-60.

\* cited by examiner

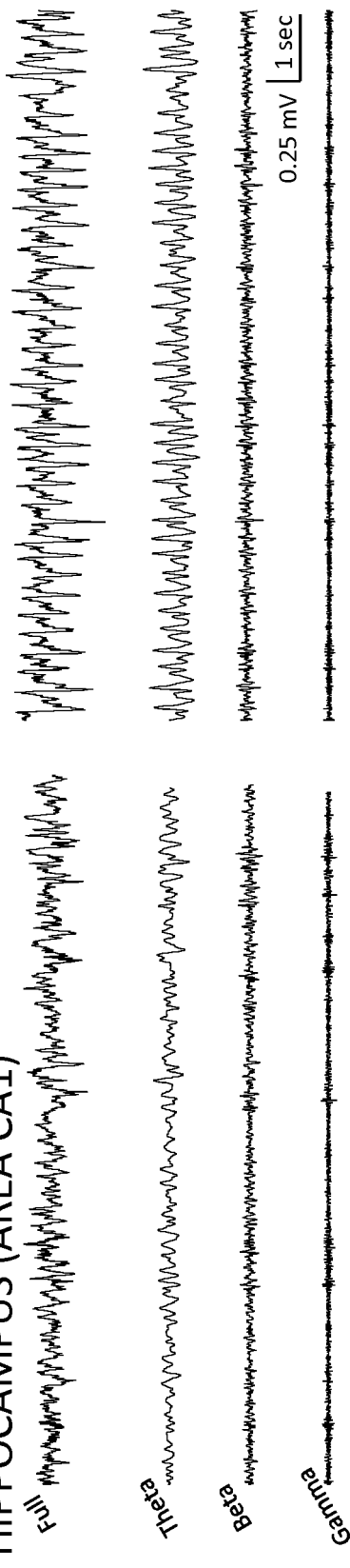
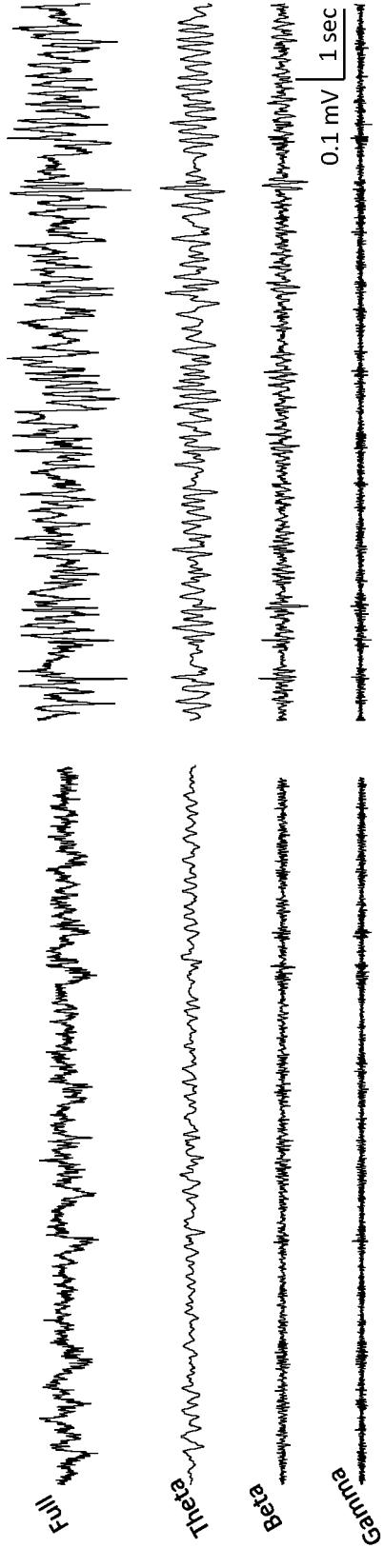
FIG. 2

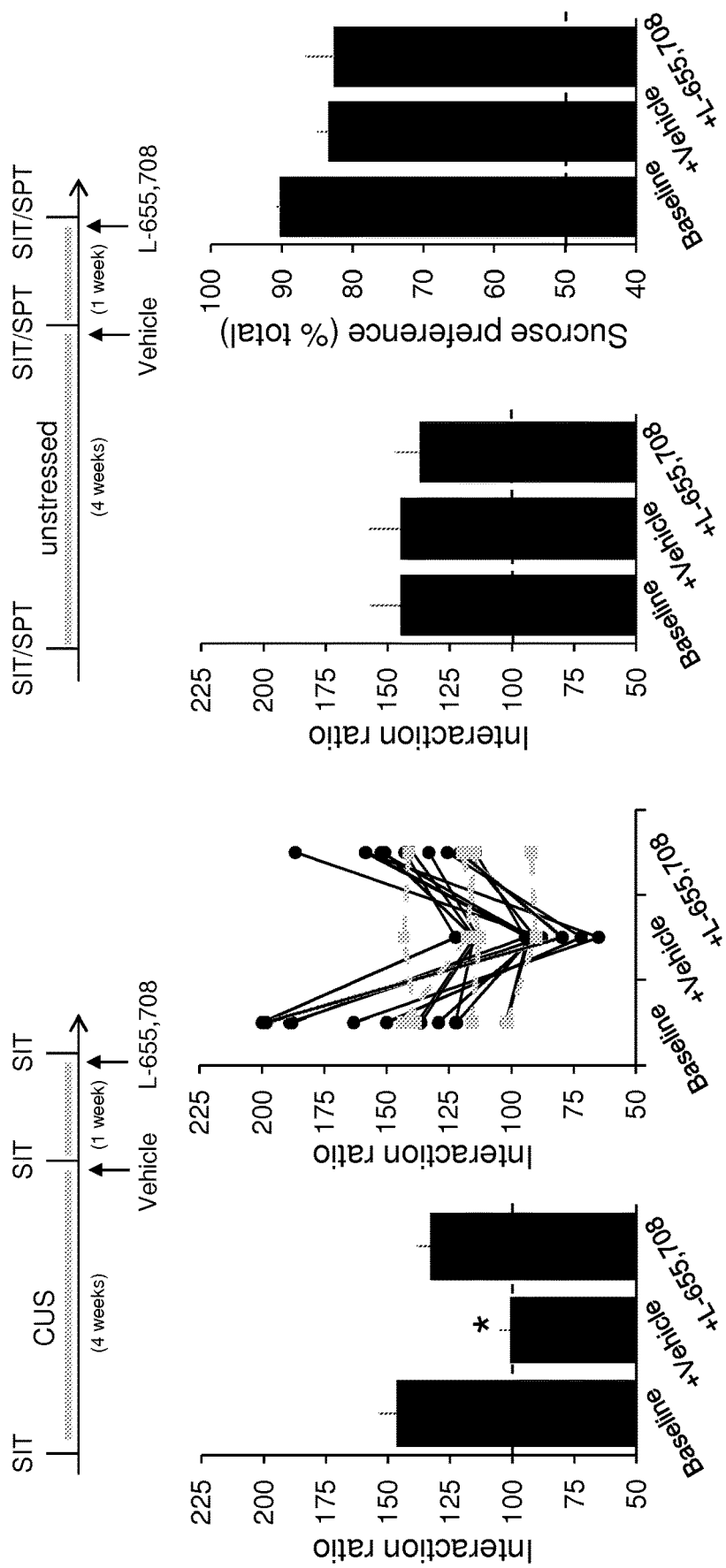

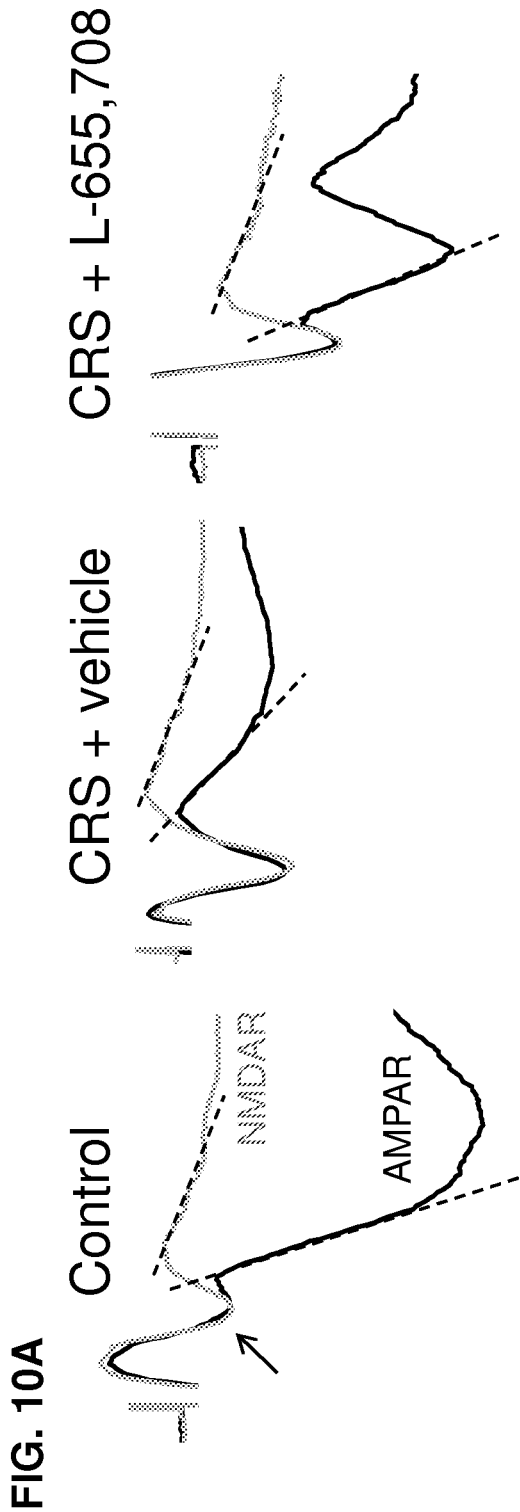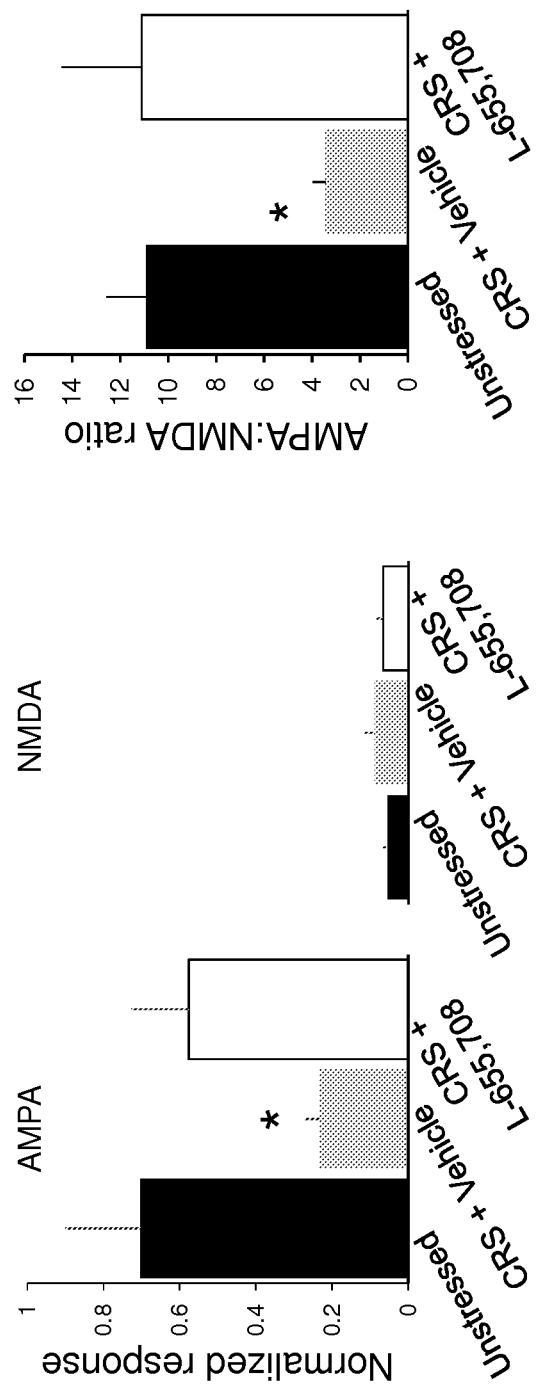
FIG. 10A
FIG. 10B
FIG. 10C

USE OF NEGATIVE MODULATORS OF GABA RECEPTORS CONTAINING ALPHA5 SUBUNITS AS FAST ACTING ANTIDEPRESSANTS

CROSS-REFERENCE TO RELATED APPLICATIONS

This application is a national phase application under 35 U.S.C. § 371 that claims priority to International Application No. PCT/US2015/023667 filed Mar. 31, 2015, which claims priority to U.S. Provisional Patent Application No. 61/972,446, filed on Mar. 31, 2014, all of which are incorporated by reference herein in their entirety.

STATEMENT REGARDING FEDERALLY SPONSORED RESEARCH OR DEVELOPMENT

This invention was made with government support under Grant Number MH086828 awarded by the National Institutes of Health. The government has certain rights in the invention.

TECHNICAL FIELD

Embodiments of the disclosure are related at least to the fields of cell biology, molecular biology, biochemistry, neurology, psychiatry, pharmacology, psychology, and medicine. In specific embodiments, the disclosure relates to methods for treating or ameliorating depression and/or suicidality in a subject by administering one or more modulators of the $GABA_A$ receptor that can produce a rapid antidepressant action.

BACKGROUND

There is a need to identify new drugs that can be used to treat depressive disorders and reduce the incidence of suicide on a worldwide basis. Selective serotonin reuptake inhibitors (SSRIs) are often the first line of treatment, but many patients do not respond to these medications and prolonged treatment (several weeks or months) is often required to achieve therapeutic improvement.

The $GABA_A$ receptor is an ionotropic receptor and ligand gated ion channel. Its endogenous ligand is gamma-aminobutyric acid (GABA), the major inhibitory neurotransmitter in the central nervous system. The primary activation site of the $GABA_A$ receptor is the binding site for GABA and several drugs, such as muscimol, gaboxadol, and bicuculline. A second binding site is the so-called "benzodiazepine receptor" site. Drugs binding at this site can promote or impair the ability of GABA to activate the $GABA_A$ receptor. $GABA_A$ receptors occur in all organisms with a central nervous system. Because of their wide distribution within the nervous system of mammals, they play a role in virtually all brain functions.

Ketamine, a recognized antagonist of the NMDA-type glutamate receptor, has demonstrated fast-acting antidepressant properties. However, ketamine is recognized to have potent psychotomimetic effects and the mechanism of action of ketamine remains uncertain. Thus, there is a clear clinical need for the identification of other fast-acting antidepressants for depression and suicidality that have enhanced pharmacokinetic properties and that can yield more robust responses with less negative side effects.

BRIEF SUMMARY

Embodiments of the disclosure concern methods and compositions for the treatment of one or more medical conditions. In particular embodiments, the one or more medical conditions includes depression and similar conditions. The condition may be of any kind, but in specific embodiments the condition being treated is major depression and/or suicidality. In specific embodiments, treatment of the medical condition occurs at a more rapid rate than currently known treatments and has fewer deleterious side effects. In specific embodiments, the medical condition is a depression-related disorder; an anxiety-related disorder; an attention-related disorder; a psychosis-related disorder; an eating disorder; a personality disorder; cognitive impairment, including that follows traumatic brain injury (TBI) or that is non-TBI cognitive impairment; neuropathic pain; chronic muscle or bone pain; diabetic complications resulting in nerve injury; generalized attack of muscular weakness; recurring sleep episodes during the day; migraine; addiction; or a combination thereof.

Embodiments of the present disclosure relate to a method for treating or ameliorating depression and/or suicidality in a human subject comprising administering to the subject a therapeutically effective amount of a modulator of a $GABA_A$ receptor. Although any modulator of a $GABA_A$ receptor that ameliorates a medical condition as described herein, in a specific embodiment the modulator is a negative modulator of the receptor. In specific embodiments, the modulator is a negative allosteric modulator of $GABA_A$ receptors containing an alpha5 subunit.

Specific embodiments of the disclosure concern the use of negative allosteric modulators of alpha5 subunit-containing GABA receptors as fast-acting antidepressants to address depression and/or reduce suicidality. In specific embodiments, fast-acting as used herein is defined as the onset of therapeutic effects being within hours to days compared to current therapies that take days to weeks to months.

In particular embodiments, any and all drugs that are negative allosteric modulators of alpha5 subunit-containing GABA receptors (including inverse agonists at the benzodiazepine binding site of $GABA_A$ receptors containing alpha5 subunits) will produce a rapid antidepressant action and will produce a rapid decrease in depression and/or suicidality in patients suffering from major depression or in patients suffering from depression that are not suicidal. Because alpha5-containing GABA receptors are narrowly expressed in the hippocampus and cortex, and because in at least some embodiments the substances are weak inverse agonists, in certain embodiments they have a significantly greater therapeutic potential than current treatments.

In one embodiment the present disclosure relates to a method for treating or ameliorating depression and/or suicidality in a human subject comprising administering to the subject a therapeutically effective amount of a negative allosteric modulator of the $GABA_A$ receptor, and in some embodiments the modulator is administered orally, intradermally, intramuscularly, intraperitonealy, intravenously, via insufflation, or in a dermal patch.

The present disclosure relates to a method for treating or ameliorating depression and/or suicidality in a human subject comprising administering to the subject a therapeutically effective amount of a negative allosteric modulator of the alpha5 subunit of the $GABA_A$ receptor and in some embodiments the modulator is administered orally intradermally, intramuscularly, intraperitonealy, intravenously, via insufflation, or in a dermal patch.

In another embodiment the present disclosure relates to a method for treating or ameliorating depression and/or suicidality in a human subject comprising administering to the subject a therapeutically effective amount of L655,708 or a derivative or analog thereof and wherein L655,708 is (but not limited to) administered orally, intradermally, intramuscularly, intraperitoneally, intravenously, via insufflation, or in a dermal patch, in specific embodiments.

In another embodiment the present disclosure relates to a method for treating or ameliorating depression and/or suicidality in a human subject comprising administering to the subject a therapeutically effective amount of MRK-016 or a derivative or analog thereof and wherein MRK-016 is (but not limited to) administered orally, intradermally, intramuscularly, intraperitoneally, intravenously, via insufflation, or in a dermal patch, in specific embodiments.

In another embodiment the present disclosure relates to a method for treating or ameliorating depression and/or suicidality in a human subject comprising administering to the subject a therapeutically effective amount of CP-457,920 or a derivative or analog thereof and wherein CP-457,920 is (but not limited to) administered orally, intradermally, intramuscularly, intraperitoneally, intravenously, via insufflation, or in a dermal patch, in specific embodiments.

In another embodiment the present disclosure relates to a method for treating or ameliorating depression and/or suicidality in a human subject comprising administering to the subject a therapeutically effective amount of RG-1662 or a derivative or analog thereof and wherein RG-1662 is (but not limited to) administered orally, intradermally, intramuscularly, intraperitoneally, intravenously, via insufflation, or in a dermal patch, in specific embodiments.

In another embodiment the present disclosure relates to a method for treating or ameliorating depression and/or suicidality in a human subject comprising administering to the subject a therapeutically effective dose of a negative allosteric modulator of the alpha5 subunit-containing $GABA_A$ receptor either alone or in combination with an another antidepressant drug including, for example, one or more selected from the group consisting of monoamine oxidase inhibitors (MAOis), selective serotonin reuptake inhibitors (SSRis), serotonin-norepinephrine reuptake inhibitors (SNRis), norepinephrine reuptake inhibitors (NRIs), triple reuptake inhibitors, modulators of CNS acetylcholine function, stimulants, anti-glucocorticoids, antagonists of NMDA-type glutamate receptors, tricylic antidepressants (TCAs), and a combination thereof.

In another embodiment the present disclosure relates to a method for treating or ameliorating depression and/or suicidality in a human subject comprising administering to the subject a therapeutically effective dose of one or more of L655,708; MRK-016; CP-457,920; RG-1662; or a derivative or analog thereof, either alone or in combination with one or more other antidepressant drugs selected from the group consisting of monoamine oxidase inhibitors (MAOis), selective serotonin reuptake inhibitors(SSRis), serotonin-norepinephrine reuptake inhibitors (SNRis), norepinephrine reuptake inhibitors (NRIs), triple reuptake inhibitors, modulators of CNS acetylcholine function, stimulants, anti-glucocorticoids, antagonists of NMDA-type glutamate receptors, tricylic antidepressants (TCAs), and combinations thereof.

In another embodiment the present disclosure relates to a method for treating or ameliorating unipolar and bipolar forms of depression, suicidality, and other depressive symptoms of unipolar and bipolar depression, posttraumatic stress disorder, and/or postpartum depression in a human subject comprising administering to the subject a therapeutically effective amount of one or more negative modulators of a $GABA_A$ receptor, including an alpha5 subunit-containing $GABA_A$ receptor and, in some embodiments, the modulator is a partial inverse agonist of an alpha5-containing $GABA_A$ receptor.

In another embodiment the present disclosure relates to a method for treating or ameliorating unipolar and bipolar forms of depression, suicidality, and other depressive symptoms of unipolar and bipolar depression, posttraumatic stress disorder, and/or postpartum depression in a human subject comprising administering to the subject a therapeutically effective dose of one or more negative modulators of a $GABA_A$ receptors, such as an inverse agonist of the alpha5 subunit-containing $GABA_A$ receptor, for example, either alone or in combination with one or more other antidepressant drugs selected from the group consisting of monoamine oxidase inhibitors (MAOis), selective serotonin reuptake inhibitors(SSRis), serotonin-norepinephrine reuptake inhibitors (SNRis), norepinephrine reuptake inhibitors (NRIs), triple reuptake inhibitors, modulators of CNS acetylcholine function, stimulants, anti-glucocorticoids, antagonists of NMDA-type glutamate receptors, tricylic antidepressants (TCAs), and a combination thereof.

In another embodiment, the present disclosure relates to a method for boosting excitatory synapse function in multiple brain regions of a human subject comprising administering to the subject a therapeutically effective amount of a negative modulator of the alpha5 subunit-containing $GABA_A$ receptor.

In another embodiment, the present disclosure relates to a method for restoring sucrose preference in a rodent animal model with stress-induced anhedonia wherein the sucrose preference increases following administration of a therapeutically effective amount of a negative modulators of a $GABA_A$ receptors, such as a negative modulator of the alpha5 subunit-containing $GABA_A$ receptor, such as L-655,708; MRK-016; CP-457,920; RG-1662; a derivative or analog thereof; or a combination thereof.

In another embodiment, the present disclosure relates to a method for treating or ameliorating depression and/or suicidality in a human subject comprising administering to the subject a therapeutically effective amount of compound L-655, 708 (ethyl (13aS)-7 -methoxy-9-oxo-11, 12,13,13 a-terahydro-9H-imidazo[1,5-a]pyrrolo[2,1-c] [1,4]benzodiazepine-1-carboxylate; MRK-016; CP-457,920; RG-1662; a derivative or analog thereof; or a combination thereof.

In another embodiment, the present disclosure relates to a method for treating or ameliorating depression and/or suicidality in a human subject comprising administering to the subject a therapeutically effective amount of compound L-655,708; MRK-016; CP-457,920; RG-1662; a derivative or analog thereof; or a combination thereof.

In another embodiment, the present disclosure relates to a method for treating or ameliorating depression and/or suicidality in a human subject comprising administering to the subject a therapeutically effective amount of compound L-655,708; MRK-016; CP-457,920; RG-1662; a derivative or analog thereof; or a combination thereof that is administered to the subject orally, intradermally, intramuscularly, intravenously, intraperitoneally, via insufflation, or in a dermal patch, in certain embodiments.

In another embodiment, the present disclosure relates to a method for treating or ameliorating depression and/or suicidality in a human subject comprising administering to the subject a therapeutically effective dose of a negative allosteric modulator of $GABA_A$ receptor, including one that comprises an alpha5 subunit, and in some cases is an inverse agonist of the alpha5 subunit-containing $GABA_A$ receptor, wherein the modulator is one or more benzodiazepine binding site inverse agonists or other binding sites that produce negative allosteric modulation of $GABA_A$ receptors containing alpha5 subunits.

In another embodiment the present disclosure relates to a method for treating or ameliorating depression in a human subject comprising administering to the subject a therapeutically effective dose of a negative allosteric modulator of $GABA_A$ receptor (including a negative modulator of a $GABA_A$ receptor that has an alpha5 subunit, such as an inverse agonist of the alpha5 subunit-containing $GABA_A$ receptor) such as L-655,708; MRK-016; CP-457,920; RG-1662; a derivative or analog thereof; or a combination thereof in combination with one or more antidepressant drugs selected from the group consisting of monoamine oxidase inhibitors (MAOis), selective serotonin reuptake inhibitors (SSRis), serotonin-norepinephrine reuptake inhibitors (SNRis), norepinephrine reuptake inhibitors (NRIs), modulators of CNS acetylcholine function, stimulants, antagonists of NMDA-type glutamate receptors, tricylic antidepressants, or a combination thereof.

In another embodiment the present disclosure relates to a method for treating or ameliorating depression in a human subject comprising administering to the subject a therapeutically effective dose of an inverse agonist of the alpha5 subunit-containing $GABA_A$ receptor, such as L-655,708; MRK-016; CP-457,920; RG-1662; a derivative or analog thereof; or a combination thereof, wherein the effective dose results in the presence of the inverse agonist in the cerebrospinal fluid at a concentration sufficient to bind 10 to 75% of all $GABA_A$ receptors and thereby reduce $GABA_A$ receptor function by 10 to 75%.

In another embodiment the present disclosure relates to a method for treating or ameliorating depression in a subject comprising administering to the subject a therapeutically effective dose of one or more negative allosteric modulators of $GABA_A$ receptor (including a negative allosteric modulator of an alpha5 subunit-comprising $GABA_A$ receptor, such as an inverse agonist of the alpha5 subunit-containing $GABA_A$ receptor), such as L-655,708 or derivatives or analogs thereof (or MRK-16 or analogs or derivatives thereof; or CP-457,920, or analogs or derivatives thereof; or RG-1662 or analogs or derivatives thereof), or a combination thereof. In particular embodiments, the effective dose of the negative allosteric modulator of $GABA_A$ receptor is administered to the subject every 0.5, 1, 2, 3, or more days or in repetitive dosing regimens. Repetitive dosing may occur when the modulator is provided alone or when it is provided with one or more other therapies, and when one or more other therapies are utilized with the modulator, the other therapies may be provided in repetitive dosing regimens.

In another embodiment the present disclosure relates to a method for treating or ameliorating depression and/or suicidality in a human subject comprising administering to the subject a therapeutically effective amount of compound L-655,708; MRK-016; CP-457,920; RG-1662; a derivative or analog thereof; or a combination thereof, in combination with another benzodiazepine binding site inverse agonist such as RO4882224, RO4938581 or other negative allosteric modulators of $GABA_A$ receptor function.

In another embodiment the present disclosure relates to a method for treating or ameliorating depression and/or suicidality in a human subject comprising administering to the subject a therapeutically effective amount of compound L-655,708; MRK-016; CP-457,920; RG-1662; a derivative or analog thereof; or a combination thereof, in combination with a 3-phenyl-5-arylpyridazine class of compounds such as RO 15-4513, RY-010, RY-023, RY-080, or RG-1662.

Embodiments of the disclosure include methods to reduce the risk of suicide in an individual prone to suicide and/or depression.

In one embodiment, there is a method of treating or preventing or ameliorating at least one symptom of a medical condition in an individual, comprising the step of providing to the individual a therapeutically effective amount of one or more negative modulators of $GABA_A$ receptors, wherein the medical condition is selected from the group consisting of a depression-related disorder; an anxiety-related disorder; an attention-related disorder; a psychosis-related disorder; an eating disorder; a personality disorder; cognitive impairment following traumatic brain injury; neuropathic pain; chronic muscle or bone pain; diabetic complications resulting in nerve injury; generalized attack of muscular weakness; recurring sleep episodes during the day; migraine; addiction; suicidality; and a combination thereof. In specific embodiments, the onset of amelioration of one or more depression-related symptoms occurs within hours, days, or weeks. In particular embodiments, the $GABA_A$ receptor comprises an alpha5 subunit. The negative modulator may be selected from the group consisting of a negative allosteric modulators acting at the benzodiazepine binding site; negative allosteric modulators acting at the barbiturate steroid binding site; negative allosteric modulators acting at the neuroactive steroid binding site; competitive antagonists of the $GABA_AR$; negative modulators acting in the pore of the $GABA_AR$ channel; nicotinamide and related compounds; inverse agonists and antagonists of the propofol binding site of the $GABA_AR$; and a combination thereof.

In certain embodiments, the depression-related disorder is major depressive disorder (MDD); dysthymia; cyclothymic disorder; seasonal affective disorder/seasonal depression; depression after traumatic brain injury; postpartum depression; premenstrual dysphoric disorder; depressive symptoms associated with menopause; depression following substance abuse/withdrawal; bipolar disorder; bipolar disorder in remission; or depressive episodes of bipolar disorder. In specific embodiments, the anxiety-related disorder is general anxiety disorder; obsessive compulsive disorder; Impulse control disorder; anxiousness associated with depression; repeated episodes of anxiety, extreme apprehension or fear of social interaction (social phobia); panic disorders; posttraumatic stress syndrome or posttraumatic stress disorder; or separation anxiety disorder. In some embodiments, the attention-related disorder is attention deficit hyperactive disorder; or adult attention deficit hyperactive disorder. The psychosis-related disorder may be schizophrenia, schizophrenia-spectrum disorder or psychotic depressive illness, in some embodiments. When the individual has an eating disorder, it may be anorexia nervosa; bulimia; or obesity. In some embodiments, the individual has avoidant personality disorder; antisocial personality disorder; borderline personality disorder; conduct disorder; dependent personality disorder; depressive personality disorder; histrionic personality disorder; narcissistic personality disorder; negativistic personality disorder; obsessive-compulsive personality disorder; paranoid personality disorder; schizoid personality disorder; or schizotypal personality disorder.

An individual treated with embodiments of the disclosure includes an individual that has been or has not been diagnosed with the medical condition.

In particular embodiments, the negative modulator of $GABA_A$ receptor is a negative allosteric modulators acting at the benzodiazepine binding site; the negative modulator of $GABA_A$ receptor is a negative allosteric modulator acting at the barbiturate steroid binding site; the negative modulator of $GABA_A$ receptor is a negative allosteric modulator acting at the neuroactive steroid binding site; the negative modulator of $GABA_A$ receptor is a competitive antagonist of the $GABA_A$R; negative modulator acting in the pore of the $GABA_A$R channel; and/or the negative modulator of $GABA_A$ receptor is a partial inverse agonist of a $GABA_A$ receptor comprising an α5 subunit. In specific embodiments, the partial inverse agonist of a $GABA_A$ receptor comprising an α5 subunit is L-655,708, RO4938581, CP-457,920, MRK-016, or a combination thereof.

In particular embodiments, the method further comprises the step of providing to the individual a therapeutically effective amount of another therapy, such as one selected from the group consisting of monoamine oxidase inhibitors (MAOis), selective serotonin reuptake inhibitors(SSRis), serotonin-norepinephrine reuptake inhibitors (SNRis), norepinephrine reuptake inhibitors (NRIs), triple reuptake inhibitors, modulators of CNS acetylcholine function, stimulants, anti-glucocorticoids, antagonists of NMDA-type glutamate receptors, tricylic antidepressants (TCAs), and a combination thereof. The other therapy may be an antidepressant.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 2. Injection of L-655,708 produced a rapid increase in oscillatory activity In str. pyramidale of area CA1 (upper row) and the NAc shell (lower row) in vivo, particularly in the theta and beta frequency bands, that persisted for more than one hour.

FIGS. 7A, 7B, 7C, and 7D. L-655,708 rapidly reverses loss of social interaction behaviors after chronic unpredictable stress but does not affect hedonic behavior in unstressed rats. Quantification of results from the social interaction test (SIT) at three time points: before CUS, after 4 weeks of CUS and a vehicle injection given 24 hrs earlier, and after an additional week of CUS and an injection of L-655,708 given 24 hrs earlier. FIG. 7A, Mean social interaction ratio differed significantly in the CUS+vehicle group compared to all other groups (3×2 repeated-measures ANOVA group-time interaction $F(2,50)=6.538$, $p=0.005$; *, $p<0.05$ vs all other groups, Bonferroni test, n=18 CUS rats, 9 unstressed rats). FIG. 7B, Analysis of individual animals revealed that 14 of 18 animals displayed robust responses to CUS and L-655,708 (black). The 4 rats that failed to respond to L-655,708 appeared largely resilient to the effects of CUS (gray symbols). Unstressed controls were also given vehicle and L-655,708 injections at the same time points. Neither injection produced a significant change in social interaction (FIG. 7C) or sucrose preference (FIG. 7D).

FIG. 9A, Quantification of results from one group of rats in the sucrose preference test at five time points: baseline, after 2 weeks of CRS, 24 hrs after an additional 3 days of CRS and 24 hrs after injection of vehicle, after one week of CRS and 24 hrs after an injection of MRK-016 (3 mg/kg), and in the same animals after an additional week of CRS and 7 days after the injection of MRK-016. Mean sucrose preference differed significantly following vehicle injection compared with all other groups ($F(3,33)=20.63$, $p<0.0001$, n=12 rats). *, $p<0.05$ compared to pre-CUS baseline, Tukey's post-hoc test). FIG. 9B, Results in individual animals for the full experiment. FIG. 9C, Quantification of results from one group of rats in the social interaction test at four time points: baseline, after 2 weeks of CRS and 24 hrs after injection of vehicle, after one week of CRS and 24 hrs after an injection of MRK-016 (3 mg/kg), and in the same animals after an additional week of CRS and 7 days after the injection of MRK-016. Mean social interaction ratios differed significantly following vehicle injection compared with all other groups (F*2,14* 11.84, p=0.0009, n=8 rats). *, p<0.05 compared to pre-CUS baseline, Tukey's post-hoc test).

FIGS. 10A, 10B, and 10C. L-655,708 rapidly reverses stress-induced weakening of AMPAR-mediated synaptic transmission in TA-CA1 synapses of the rat hippocampus. FIG. 10A, representative traces showing the AMPAR- and NMDAR-mediated components of the fEPSP, recorded extracellularly in SLM of area CA1 in response to simulation of TA afferents in saline lacking added Mg2+. Traces are shown before (black) and after (gray) addition of 50µM DNQX to block AMPARs. Traces were recorded from slices taken from unstressed controls (left) and rats subjected to 10 days of CRS then given an injection 24 hrs earlier of either vehicle solution (middle) or L-655,708 (right). FIG. 10B, the mean slope of the relationship between AMPAR- (left) and NMDAR-mediated response (right) and FV amplitude over a range of stimulation intensities from the three groups of animals. The slope of the AMPAR-mediated responses was decreased significantly in slices from vehicle-treated CRS rats (gray, middle bar of triplet of bars) compared to slices from unstressed (black, left bar of triplet of bars) or L-655,708-treated CRS rats (white, right bar of triplet of bars) across the range of stimulation intensities (1-Way ANOVA, F(2,17), 3.675, p=0.047; n=5 unstressed, 8 CRS+vehicle, 7 CRS+L-655,708; *, p<0.05, LSD post hoc test). There were no significant differences in NMDAR-mediated responses (1-Way ANOVA, F(2,17)=0.549, p=0.588). FIG. 10C, AMPA:NMDA ratios were computed from the initial slopes of the responses in each slice before and after application of DNQX (shown by dotted lines in A). AMPA:NMDA ratios were decreased significantly in slices from vehicle-treated CRS rats compared to slices from either unstressed or L-655,708-treated CRS rats (1-Way ANOVA F(2,17)=4.345 p=0.03; n=5 unstressed, 8 CRS+vehicle, 7 CRS+L-655,708; *, p<0.05 compared to unstressed and CRS+L-655,708, LSD post-hoc test). Bar notations in FIG. 10C are the same as in FIG. 10B.

FIG. 11A, Representative Western blots of GluA1 and β-actin protein levels in SLM samples from unstressed rats (left) and rats subjected to 10 days of CRS then given an injection 24 hrs earlier of either vehicle solution (middle) or L-655,708 (right). FIG. 11B, GluA1 expression, normalized to β-actin levels, was decreased significantly in tissue from vehicle-treated CRS rats (gray, middle bar of triplet of bars) compared to tissue from unstressed (black, left bar of triplet of bars) or L-655,708-treated CRS rats (white, right bar of triplet of bars) (Kruskal-Wallis H test: χ2(2)=10.62, p=0.0049; n=6 unstressed, 6 CRS+vehicle, 8 CRS+L-655,708; *, p<0.05 compared to unstressed and CRS+L-655,708, post-hoc Mann-Whitney U test).

FIG. 12A, Percent time spent in the interaction zone is quantified for rats during the baseline period and 24 hrs after injection of either vehicle (white, right bar of pair of bars) or L-655,708 (black, left bar of pair of bars) for the experiments illustrated in FIG. 12A. FIG. 12B, Percent time spent in the interaction zone is quantified for rats subjected to CUS (black, left bar of pair of bars) or unstressed rats (white, right bar of pair of bars) during the baseline period, 24 hrs after injection of vehicle, and 24 hrs after injection of L-655,708 for the experiments illustrated in FIG. 6B.

DETAILED DESCRIPTION

I. Exemplary Definitions

Figure 1:
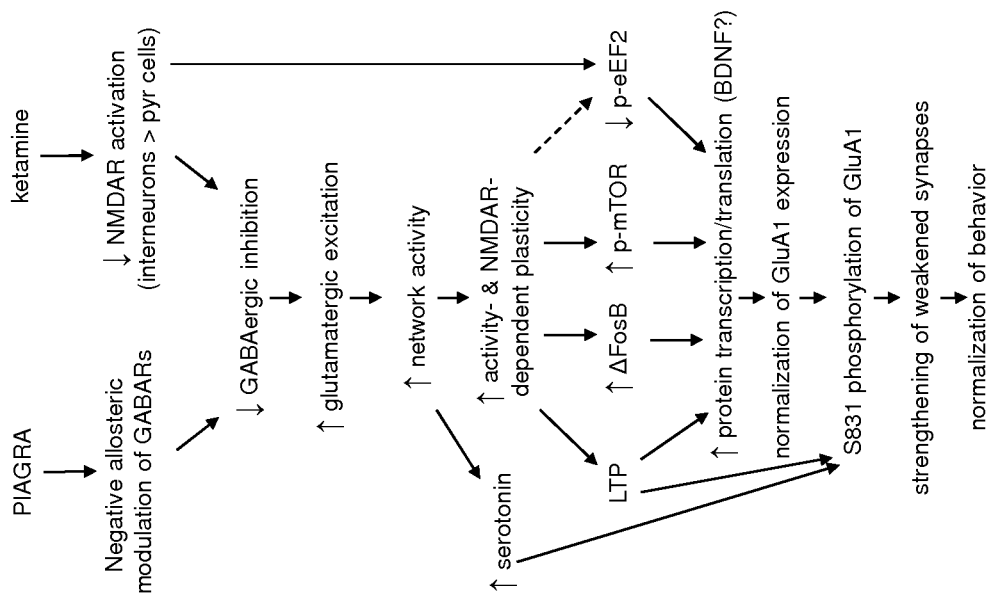
FIG. 1 illustrates an example of ketamine's fast-acting therapeutic action and the involvement of excitatory synapses in depression.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The terms "therapeutic level;" "therapeutically effective dose," "therapeutically effective amount," and the like, as used herein, refer to an amount or concentration of a compound or agent, e.g., a $GABA_AR$ antagonist, that achieves a therapeutic effect in a subject, wherein the therapeutic effect can be an amelioration, or alleviation, if not complete cessation, of one or more symptoms of clinical depression and other similar conditions, including suicidality as defined elsewhere herein. In particular embodiments, an effective dose is the dose of the compound that results in the presence of the compound in the cerebrospinal fluid at a concentration sufficient to bind to $GABA_A$ receptors, including those containing alpha 5 subunits. In specific embodiments, an effective dose is the dose of the compound that results in the presence of the compound in the cerebrospinal fluid at a concentration sufficient to bind to 10-75% of all $GABA_ARs$ and thereby reduce $GABA_AR$ function by 10-75%, although in specific embodiments the percentages are 10-100%, 10-90%, 10-80%, 10-70%, 10-60%, 10-50%, 10-40%, 10-30%, 10-20%, 20-100%, 20-90%, 20-80%, 20-70%, 20-60%, 20-50%, 20-40%, 20-30%, 30-100%, 30-90%, 30-80%, 30-70%, 30-60%, 30-50% 30-40%, 40-100%, 40-90%, 40-80%, 40-70%, 40-60%, 40-50%, 50-100%, 50-90%, 50-80%, 50-70%, 50-60% 60-100%, 60-90%, 60-80%, 60-70%, 70-100%, 70-80%, 70-90%, 70-80%, 80-100%, 80-90%, 90-100, and so forth. In specific embodiments, the percentage of receptors that are bound is greater than 10, 20, 30, 40, 50, 60, 70, 80, 90, or 95%.

II. General Embodiments

Major depressive disorder (MDD) afflicts nearly 20 percent of the world population, with suicide as a too-common and tragic end. Monoaminergic antidepressants (ADs), such as selective serotonin reuptake inhibitors (SSRIs), are the first line treatment for MDD, but many patients do not respond to these medications and clinical improvement generally requires prolonged treatment (weeks to months) in patients that do. The delay in efficacy, as well as the high non-response rate, have motivated the search for better AD drugs. Ketamine, a noncompetitive NMDA receptor (NMDAR) antagonist, has demonstrated efficacy as a rapidly acting AD in treatment refractory patients. Low doses of ketamine result in a rapid and sustained improvement in core depressive symptoms and a decrease in suicidal ideation in individuals with treatment-resistant MDD (Berman et al., 2000; Zarate et al., 2006). Similarly, systemic ketamine administration at sub-anesthetic doses (3-50 mg/kg) results in AD-like behavior in several rodent models of depression (Maeng et al., 2008; Li et al., 2011). Although ketamine exerts a rapid AD action in humans, its potential for use outside of the research setting is limited because it is addictive and because it produces dissociative, psychotomimetic effects even at low doses (e.g. Machado-Vieira et al., 2009). Thus, even though ketamine itself has limited therapeutic potential, its rapid action has kindled great enthusiasm for the possibility of developing rapidly acting ADs. Ketamine has also provided a critical mechanistic insight into how rapid AD actions may be produced (e.g. Li et al., 2011), raising hopes that new drugs can be developed that lack its disadvantages and risks.

The mechanism of ketamine's fast-acting therapeutic action remains uncertain. It has been postulated that ketamine is somewhat selective for NMDARs on inhibitory interneurons, so that their excitation is diminished by ketamine, resulting in a mild disinhibition of the neuronal population and overall increase in its activity. Ketamine-induced increases in activity then cause stimulation of activity-dependent processes such as long-term potentiation and activation of the mammalian target of the rapamycin (mTOR) signaling pathway leading to the rapid induction of synaptogenesis via increased synthesis of synaptic proteins (Li et al., 2010) and restoration of normal activity.

In the present disclosure, in certain embodiments it was considered that it is ultimately the mild increase in global activity in forebrain neural circuits that is a mechanism via which rapid therapeutic AD actions are exerted. Therefore, other means were sought to produce such changes. In one embodiment, it was considered to produce a direct decrease in the strength of inhibition mediated by y-aminobutyric acid type-A receptors ($GABA_A Rs$). Disinhibition promotes anxiety and epileptiform discharge, however. In another embodiment, related to efforts to develop memory-enhancing drugs, an alternative to ketamine as a rapidly acting AD includes partial inverse agonists of α5-containing $GABA_A Rs$.

$GABA_A Rs$ are heteropentameric, ligand-gated ion channels. Nineteen $GABA_A$ receptor subunits have been identified to date. Most $GAB_A A$ receptors contain α, β, and γ2 subunits in a 2:2:1 stoichiometry. β subunits direct membrane insertion whereas adjacent γ2 and α subunits form the benzodiazepine site, an allosteric modulator of channel gating. The identity of the α subunit determines the pharmacological profile of this site. Receptors containing α1, α2, or α3 subunits are potentiated by zolpidem, a benzodiazepine type 1 agonist, whereas receptors containing α5 subunits are essentially insensitive to zolpidem. Recent studies have shown that α1 subunits mediate the sedative, anticonvulsant and amnestic effects of benzodiazepines preferentially, whereas the α2 and α3 subunits mediate their anxiolytic effects. In addition to the anxiolytic agonists of benzodiazepines, there is a class of drugs, exemplified by the β-carbolines, that act as full or partial inverse agonists at the benzodiazepine site to decrease $GABA_A$ receptor function. Partial inverse agonists offer the advantage of a wider therapeutic concentration range and a lower likelihood of producing anxiety or epileptiform discharge, in specific embodiments of the disclosure.

α5-subunit mRNA is highly expressed in the pyramidal cells of the hippocampus and cortex (Allen Brain Atlas) and α5-containing $GABA_A$ receptors are localized in the dendrites of hippocampal CA1 pyramidal cells at synaptic and extrasynaptic sites. Because disinhibition promotes induction of long-term potentiation (LTP), and because of their selective forebrain localization, drugs that selectively inhibit α5-containing receptors are being developed as cognitive enhancers. It has been shown, for example, that partial inverse agonists of α5-containing $GABA_A$ receptors enhance associative memory acquisition in hippocampal-dependent learning tasks.

Thus, in particular embodiments of the disclosure one or more partial inverse agonists of the benzodiazepine binding site of $GABA_A$ receptors, particularly those containing an α5 subunit, produce a rapid antidepressant action in unipolar and bipolar forms of depression and reduce suicidal ideation by restoring the normal function of excitatory synapses. Such considerations may be characterized, by example, using a rodent model of depression with face, construct, and predictive validity, chronic unpredictable stress (CUS) to compare the actions of acute administration (24 hrs) of the α5-selective partial inverse agonists (RO4938581, Ballard et al., 2009; MRK-016, Atack et al., 2009) and the non-selective inverse agonist (FG7142; Shansky et al., 2004) with the actions of acutely administered ketamine. Antidepressant efficacy of partial inverse agonists of α5 subunit-containing $GABA_A$ receptors are then tested in vivo using the sucrose preference and social exploration tests (Amat et al., 2010), for example. One could also determine the ability of partial inverse agonists of α5 subunit-containing $GABA_A$ receptors to reverse the electrophysiological correlates of stress-induced depression using electrophysiological and biochemical analyses in vitro.

In embodiments of the disclosure, partial inverse agonists of α5 subunit-containing $GABA_A$ receptors exert an antidepressant action comparable to ketamine's (Ibrahim et al., 2012). In certain embodiments, patients may undergo standard psychiatric screening for DSM-IV criteria for major depressive episodes. In specific embodiments, a saline solution comprising one or more of the agonists are provided to the individual, such as infused slowly (ca. 30-60 min), for example. Depression-related and other rating tests, such as the Hamilton Depression Rating Scale, Beck Depression Inventory, Visual Analog Scales score for intoxication "high", and the Brief Psychiatric Rating Scale, may be given repeatedly; as an example only, they may be given over a four hour period after drug administration, and daily over the following seven days. Antidepressant efficacy, as well as psychotomimetic or anxiogenic responses, is determined upon changes in the test scores, in specific embodiments to show efficacy with a particular compound.

The studies encompassed herein are the first to characterize the antidepressant-like efficacy of partial inverse agonists of α5 subunit-containing $GABA_A$ receptors. Rapid onset of antidepressant action, shown using established preclinical models, for example, is highly desirable from a clinical perspective and has never been attempted with these compounds. The studies allow one to demonstrate that partial inverse agonists of α5 subunit-containing $GABA_A$ receptors are useful at least as a treatment for depression.

III. Medical Conditions of the Disclosure

There are a variety of medical conditions in which treatment as encompassed in this disclosure produces a beneficial therapeutic response. The medical condition may be diagnosed prior to treatment. In specific embodiments, the individual is suspected of having the medical condition, is at risk for having the medical condition, has shown behavior indicative of the medical condition, has a personal or family history of the medical condition, and so forth. In certain embodiments, symptoms of the medical condition may overlap with symptoms form other types of related medical conditions.

In specific embodiments, there is clinical efficacy in any condition in which antidepressant medication(s) are currently being used, either with regulatory approval or through 'off label' use. Specific examples of medical conditions in which the methods and compositions of the disclosure are useful include but are not limited to depression-related disorders (such as Major depressive disorder (MDD); dysthymia; cyclothymic disorder; seasonal affective disorder/ seasonal depression; depression after traumatic brain injury; postpartum depression; premenstrual dysphoric disorder; depressive symptoms associated with menopause; depression following substance abuse/withdrawal; bipolar disorder; bipolar disorder in remission; and depressive episodes of bipolar disorder); anxiety-related disorders(such as general anxiety disorder; obsessive compulsive disorder; Impulse control disorder; anxiousness associated with depression; repeated episodes of anxiety, extreme apprehension or fear of social interaction (social phobia); panic disorders; posttraumatic stress syndrome or posttraumatic stress disorder; and separation anxiety disorder); attention-related disorders (such as attention deficit hyperactive disorder; adult attention deficit hyperactive disorder); psychosis-related disorders (such as schizophrenia, schizophrenia-spectrum disorder; psychotic depressive illness); eating disorders (such as anorexia nervosa; bulimia; obesity); personality disorders (such as avoidant personality disorder; antisocial personality disorder; borderline personality disorder; conduct disorder; dependent personality disorder; depressive personality disorder; histrionic personality disorder; narcissistic personality disorder; negativistic personality disorder; obsessive-compulsive personality disorder; paranoid personality disorder; schizoid personality disorder; schizotypal personality disorder) and other conditions such as cognitive impairment following traumatic brain injury; neuropathic pain; chronic muscle or bone pain; diabetic complications resulting in nerve injury; generalized attack of muscular weakness; recurring sleep episodes during the day; migraine treatment and prevention; and nicotine addiction. Also, treatment-related issues may be addressed, such as lack of compliance with current treatment(s) and intolerance of side-effects from current treatments(s). Embodiments of the disclosure provide for an improvement over other therapies in the art in cases wherein the treatment of the disclosure is effective with fewer doses than other therapies in the art.

In particular embodiments, the individual is known to have or is suspected of having MDD (which is also known as clinical depression, major depression, unipolar depression, or unipolar disorder; or as recurrent depression in the case of repeated episodes), which is a mental disorder characterized by a pervasive and persistent low mood that is accompanied by low self-esteem and by a loss of interest or pleasure in normally enjoyable activities. In specific embodiments, the individual with MDD (or with another medical condition) is suicidal, although in specific embodiments the suicidal person does not have depression. As an example, an individual may be suicidal who has one or more of the following attributes: depression; previous suicide attempts; preoccupation with death; making troubling or morose statements; talking openly about wanting to kill oneself; having developed a suicide plan; having acquired the means to carry out a suicide plan; "rehearsal" behavior; setting a time for a suicidal attempt; self-inflicted injuries, such as cuts, burns, and/or head banging; engaging in risky behavior, such as driving recklessly, using drugs and/or high-risk sexual behavior; making out a will or giving away favorite possessions; inappropriately saying goodbye, and so forth. In cases where the individual has depression, it may be unipolar or bipolar. The individual may have a propensity for depression and/or suicidal thoughts because of a genetic or familial predisposition, for example, but not limited to, having the brain-derived neurotrophic factor (BDNF) Va166Met polymorphism and/or the transporter gene 5HTLPPR promoter region polymorphism.

In specific embodiments, the condition being treated with methods and compositions encompassed by the disclosure is considered resistant to treatment with previously existing treatments for depression (including SSRIs, SNRIs and/or TCAs for example), such as treatment-resistant MDD, for example.

Although in particular embodiments the medical condition is diagnosed prior to treatment, in other embodiments the individual is treated without formal diagnosis of the condition, such as in cases where a first responder, medical responder, family member, hospital worker, or so forth considers the treatment to be warranted. The individual may or may not be treated in a medical facility. In specific embodiments, the individual suffers from depression, has had one or more concussions or other brain injury, is being treated with a therapy (such as a drug) that has suicide and/or depression as a side effect, abuses alcohol or other prescription or recreational drugs, is a victim of mental and/or sexual abuse, a combination thereof, and so forth. The individual may be a professional athlete that has had one or more concussions, as an example. The individual may currently be in the military or may have been in the military. The individual may be of any race or gender or age.

In specific embodiments, the treatment for the individual is considered to be effective in a shorter period of time than known treatment(s) for the condition. For example, in the case of compositions of the disclosure, the individual may have a therapeutic effect within minutes, hours, days or weeks of the first administration. In particular embodiments, the individual is given the therapeutic composition(s) once or more than once. In specific embodiments, there are one or more therapeutic effects with the composition of the disclosure no more than days, hours, or minutes after the first administration. For example, the therapeutic effect may take place no more than 14, 13, 12, 11, 10, 9, 8, 7, 6, 5, 4, 3, 2, or 1 day after the first administration. The therapeutic effect may take place no more than 96, 72, 48, 24, 23, 22, 21, 5, 4, 3, 2, or 1 hour after the first administration. The therapeutic effect may take place no more than 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 minute after the first administration. A therapeutic effect may comprise a situation where the individual no longer wants to commit suicide, or has a reduced desire to commit suicide, or is having second thoughts about committing suicide, or is now uncertain about committing suicide, for example. A therapeutic effect may comprise when an individual no longer has depression or when the individual is less depressed or has fewer depression symptoms or has longer periods of time in between depressive moods, for example.

IV. Compositions of the Disclosure

In specific embodiments of the disclosure, one may employ one or more compositions for the treatment of one or more medical conditions in which modulation of the $GABA_A$ receptor is therapeutically effective for the condition(s). In specific embodiments, the $GABA_A$ receptor comprises an alpha5 subunit. Although in particular embodiments any such condition is treatable, in specific embodiments the condition has depression or suicidality as at least one symptom. In particular embodiments, administration of one or more compositions of the disclosure to the individual provides treatment of the condition or prevention of the condition and/or reduces the onset of the condition and/or reduces the severity of one or more symptoms of the condition.

In specific embodiments, the composition utilized for methods of the disclosure includes one or more $GABA_A$ receptor negative modulators. The term $GABA_A$ receptor negative modulators, as used in this disclosure, may refer to compounds that decrease the activity of the $GABA_A$ receptor, e.g., by blocking or reducing the influx of chloride ions through the pore of the $GABA_AR$ (i.e. channel blockers), and/or by blocking or reducing binding of an agonist to the $GABA_AR$ (i.e. $GABA_AR$ antagonists) and/or blocking or reducing an effect of an agonist on the $GABA_AR$ (i.e. negative allosteric modulators). An exemplary $GABA_AR$ channel blocker is picrotoxin. Exemplary $GABA_AR$ antagonists include bicuculline and pentylenetetrazole. An exemplary $GABA_AR$ channel blocker is picrotoxin. Exemplary $GABA_AR$ negative allosteric modulators include non-selective and selective benzodiazepine receptor inverse agonists.

Examples of $GABA_A$ receptor negative modulators are as follows:

1. Negative allosteric modulators acting at the benzodiazepine binding site. Beta-subunits direct membrane insertion whereas adjacent gamma2 and alpha subunits form the so-called benzodiazepine site, an allosteric modulator of channel gating. The identity of the a subunit determines the pharmacological profile of this site. $GABA_AR$ s containing alpha1, alpha2 or alpha3 subunits are potentiated by zolpidem, a benzodiazepine type 1 agonist, whereas $GABA_ARs$ containing alpha5 subunits are essentially insensitive to zolpidem (Burgard et al., 1996). Recent studies have shown that a1 subunits mediate the sedative/anticonvulsant and amnestic effects of benzodiazepines preferentially, whereas the alpha2 and alpha3 subunits mediate their anxiolytic effects (Rudolph et al., 1999; Mohler et al., 2002), In addition to the anxiolytic agonists of benzodiazepines there is a class of drugs, exemplified by the β-carbolines which act as full or partial inverse agonists at the benzodiazepine site to decrease $GABA_AR$ function. Partial inverse agonists offer the advantage of a wider therapeutic concentration range and a lower likelihood of producing anxiety or epileptiform discharge, in specific embodiments.

alpha5-subunit mRNA is highly expressed in the pyramidal cells of the hippocampus and cortex (Allen rain Atlas) and alpha5-containing $GABA_ARs$ are localized in the dendrites of hippocampal CA1 pyramidal cells (Fritschy and Mohler, 199S; Wainwright et al., 2000) at synaptic and extrasynaptic sites (Serwanski et al. 2006). Because disinhibition promotes induction of long-term potentiation (LTP), and because of their selective forebrain localization, drugs that selectively inhibit alpha5-containing receptors are being developed as cognitive enhancers (Ballard et al., 2009). It has been shown, for example, that partial inverse agonists of α5-containing $GABA_ARs$ enhance associative memory acquisition in hippocampal-dependent learning tasks (Collinson et al., 2002).

Representative examples of benzodiazepine binding site inverse agonists are as follows:

General, non-subunit-selective: sarmazenil, beta-carbolines, S-8510, DMCM, FG 7142.

Alpha5 subunit-selective: the imidazo[1,5-a][1,2,4]-triazolo[1,5-d][1,4]benzodiazepine class of compounds (such as R04882224, R04938581, L-655,708), the triazolophthalazine class of compounds (such as α5IA), the 7,8,9,10-tetrahydro-(7,10-ethano)-1,2,4-triazolo[3,4-a]phthalazine class of compounds, the pyrazolotriazine class of compounds (such as MRK-016), the 6,7-Dihydro-2-benzothiophen-4(5H)-one class of compounds, 6,6-Dimethyl-3-(2-hydroxyethyl)thio-1-(thiazol-2-yl)-6,7 -dihydro-2-benzothiophen-4(5H)-one, the 3,4-Dihydronaphthalen-1 (2H)-one class of compounds, (3-tert-butyl-7-(5-methylisoxazol-3-yl)-2-(1-methyl-1H-1,2,4-triazol-5-ylmethoxy)pyrazolo [1,5-d] [1,2,4]triazine, the 3-Phenyl-5-arylpyridazine class of compounds, Ro 15-4513, RY-010, RY-023, RY-024, RY-080, and RG1662.

2. Negative allosteric modulators acting at the barbiturate steroid binding site. Barbiturates are drugs that were originally developed for their sedative properties. They act as positive allosteric modulators of $GABA_ARs$ to increase the efficacy of GABA through an increase in channel open time. Barbiturates are thought to bind at the interface between an α and β subunit of the $GABA_AR$ (Sieghart et al., 2012). Barbiturates at supra-clinical concentrations may also directly open the channel in the absence of GABA. Although negative allosteric modulators acting at this site have not yet been described, in specific embodiments they exert antidepressant actions and may or may not be selective for alpha5 subunit containing receptors.

3. Negative allosteric modulators acting at the neuroactive steroid binding site. Neuroactive steroids are endogenous compounds that can be synthesized in the brain from cholesterol or steroidal precursors or by metabolism of adrenal steroids or gonadal steroids, such as testosterone (Mellon and Griffin, 2002). Examples of neuroactive steroids include pregnenolone and dehydroepiandrosterone, their sulfates, and their reduced metabolites. Allopregnanolone and tetrahydrodeoxycorticosterone are positive allosteric modulators of $GABA_AR$-mediated chloride currents, whereas pregnenolone sulfate and dehydroepiandrosterone (DHEA) sulfate are negative allosteric modulators. Neuroactive steroids bind to the delta subunit of the $GABA_AR$, which is expressed heavily in the forebrain and ventral striatum; brain regions implicated in the genesis of depression. There is evidence that pregnancy is associated with decreases in the expression of delta subunits and elevation of neurosteroid levels (Maguire et al., 2009), in specific embodiments implicating dysregulation in their interactions as a contributing factor in post-partum depression.

Drugs have been developed to mimic the positive allosteric effects of neuroactive steroids and are used clinically as sedatives and anesthetics, such as alphaxolone, alphadolone, hydroxydione and minaxolone. Because of the presence of endogenous neuroactive steroids in the brain, an antagonist of this site can also be predicted to weaken $GABA_AR$-mediated inhibition. Because some selective serotonin reuptake inhibitors (SSRIs), such as fluoxetine, are reported to elevate levels of endogenous neuroactive steroids in the brain (Pinna et al., 2006), in specific embodiments an antagonist at this site also amplifies the effects of such SSRIs. Drugs interacting at this site are useful in the treatment of postpartum depression, in specific embodiments.

4. Competitive antagonists of the $GABA_AR$. Numerous compounds have been developed that act to block the binding of GABA to the $GABA_AR$ in a competitive manner. A well-known example is bicuculline. Competitive antagonists decrease the ability of synaptically released GABA to activate the channel. Potent members of this class of compound reduce inhibition so much that they are often used to elicit epileptiform discharge in preclinical studies. A proconvulsive action would need to be greatly minimized to render a member of this class of compounds clinically useful, however an antagonist with low affinity is useful, in certain embodiments.

Representative examples of $GABA_AR$ antagonists are as follows: picrotoxin, bilobalide, pentylenetetrazol, thujone, and ginkgolide B.

5. Negative modulators acting in the pore of the $GABA_AR$ channel. Numerous compounds have been developed that act to block the flux of Cl-ions through the pore of the $GABA_AR$. Because they do not compete with GABA at its receptor on the channel, they are referred to as noncompetitive antagonists (NCA). The best known example is picrotoxinin, which is also highly epileptogenic. Drugs active at this site are widely used as insecticides and act by physically blocking the channel, although allosteric modulation has not been ruled out. The β3 subunit may be particularly relevant for NCA binding (Chen et al., 2006). Low affinity blockers would be helpful for clinical utility.

6. Other negative modulators. Nicotinamide and related compounds, as well as inverse agonists and antagonists of the propofol binding site of the $GABA_AR$, are useful negative modulators of $GABA_AR$-mediated inhibition, in specific embodiments.

Thus, in specific embodiments one or more negative modulators of $GABA_A$ receptors, whether acting allosterically, blocking the channel, or blocking the receptor for GABA itself, are utilized in therapeutic methods of the disclosure, for example to produce a robust antidepressant action in unipolar and bipolar forms of depression, in posttraumatic stress disorder, and in postpartum depression, by elevating mood and/or reducing suicidal ideation. In specific embodiments, the mechanism of action of these compounds is a strengthening of excitatory synapses that are pathologically weakened in depressed patients. In specific embodiments, these compounds act more rapidly than conventional antidepressants, such as inhibitors of monoamine neurotransmitter reuptake and catabolism. In particular embodiments, depression results from a pathological weakening of excitatory synapses in multiple brain regions affecting the function of reward circuits in the ventral midbrain, and the methods of the disclosure provide a therapy that addresses this physiological event.

In one embodiment of this disclosure, $GABA_AR$ negative modulators are given alone at a therapeutically effective dose. In another embodiment, $GABA_AR$ negative modulators are given at a therapeutically effective dose together with one or more conventional antidepressant treatments. In this embodiment, the conventional antidepressant(s) can be given (for example, orally) at current FDA-approved standard dosing regimens.

In an embodiment of the disclosure, $GABA_AR$ negative modulators are given at a therapeutically effective dose, fixed or varying, over an unlimited period of time to treat depression and related conditions. In specific embodiments, an individual is provided an initial dosing regimen that has a stronger dose of the treatment than a later dosing regimen that has a dose that is less than the initial dose. In some embodiments, an individual is provided an initial dosing regimen that has a smaller dose of the treatment than a later dosing regimen that has a dose that is greater than the initial dose.

In an embodiment of the disclosure, $GABA_AR$ negative modulators are given at a therapeutically effective dose on a limited number of occasions (e.g., once per week or once every 2-3 days) for a limited period of time (e.g., 1-4 months). The modulator may be given 1, 2, 3, or 4 or more times a day for a particular period of time, such as 1, 2, 3, 4, 5, 6, 7, 8, 9, 10, 11, 12 or more weeks, or 1, 2, 3, 4, 5, 6, 7, 8, 9, 10, 11, 12, or more months. Conventional antidepressant treatments may be given continuously, as per current dosing regimens approved by the FDA and other regulatory authorities. The depressive status of the individual may or may not be ascertained throughout the course of treatment.

In specific embodiments, a $GABA_AR$ negative modulator acts on alpha 5 but also acts on other subunits of the $GABA_AR$.

In particular embodiments, one or more analogs or derivatives of a $GABA_AR$ negative modulator are utilized. One of skill in the art recognizes how to modify a modulator and test its activity in methods described elsewhere herein, such as in mouse models.

In certain embodiments, the formulation of the one or more modulators is tailored toward the need of the individual. For example, in cases wherein an individual has a chronic depression problem, the formulation may need to be such that the amount in the individual is kept at a plateau, yet the modulator for an individual with imminent severe depression and/or suicide may need to be formulated so that it enters the bloodstream quickly.

V. Combination Therapy

In certain embodiments, methods of the present disclosure for clinical aspects are combined with other agents effective in the treatment of one or more medical conditions encompassed by the disclosure. The present inventive therapy may precede or follow the other agent treatment by intervals ranging from minutes to days to weeks, for example. In embodiments where the other agent and composition(s) of the present disclosure are given separately to the individual, one would generally ensure that a significant period of time did not expire between the time of each delivery, such that the other agent and inventive therapy would still be able to exert an advantageously combined effect on the cell. In such instances, it is contemplated that one may contact the cell with both modalities within about 0-24 h of each other and, in specific embodiments, within about 6-12 h, 1-6 h, less than one hour, 1-12 h, 1-3 h, or 1-24 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In specific embodiments, the treatment cycles would be repeated as necessary.

In certain embodiments, an additional therapy is provided to the individual at the onset of treatment with methods and/or compositions of the disclosure, although the additional therapy may be provided before, during, and/or after the onset of treatment with methods and/or compositions of the disclosure. In some cases, the individual may cease the treatment with methods and/or compositions of the disclosure once an additional therapy has been given to the individual, including for such a period of time that the additional therapy is able to be effective.

In particular embodiments, one or more additional therapies other than those encompassed by the disclosure and in addition thereto are provided to the individual. The additional therapy may be for depression, suicidal tendencies, and so forth. Examples of conventional antidepressant drugs and treatment are provided below, and one or more of these may be employed with compositions of the disclosure. Doses are mg/day per os (p.o.) unless otherwise noted.

Monoamine oxidase inhibitors (MAOJs) include Selegiline −1.25-12 mg/day; Tranylcypromine 10-60 mg/day;

Moclobemide 100-600 mg/day (reversible MAOI, approved outside the US); Phenelzine 15-90 mg/day; Isocarboxazid; and a combination thereof.

Selective Serotonin reuptake inhibitors (SSRIs) include Citalopram 10-20 mg/day; Escitalopram 10-20 mg/day; Fluoxetine 10-40 mg/day, or 90 mg/week slow release; Paroxetine 10-40 mg/day; Sertraline 25-200 mg/day; Fluvoxamine 50-300 mg/day; and a combination thereof.

Selective Serotonergic and Noradrenergic Reuptake Inhibitors (SSRI/SNRI) include Venlafaxine XR 37.5-225 mg/d; Desvenlafaxine 50-100 mg/day; Duloxetine 20-120 mg/day; Milnacipran 12.5-200 mg/day; Levomllnacipran; Amoxapine; Protriptyline; Nefazodone (moderate antagonist at 5HT-2 and alpha1-adrenergic receptors); and a combination thereof.

Stimulants (off-label use) include Methylphenidate 2.5-20 mg/day p.o., or 10-30 mg transdermal; Modafinil 100-400 mg; and a combination thereof.

Examples of antagonists of NMDA-type glutamate receptors include ketamine 6.5-13 mg/kg intramuscular injection, or 1-4.5 mg/l<g intravenous; Lanicemine (aka AZD6765 or AR-R15896AR); Memantine 5-20 mg/day; Amantadine 100-200 mg/day; Methoxetamine 6-10 mg/kg (NMDAR and serotonin reuptake); Riluzole 50 mg/day; and a combination thereof.

Examples of Tricyclic antidepressants (TCAs) include Desipramine 10-150 mg/day; Nortriptyline 10-100 mg/day; Amitriptyline 20-300 mg/day; Clomipramine 25-250 mg/day; Doxepin 10-300 mg/day; Imipramine 30-300 mg/day; Melitracen 10-225 mg/day; Amlneptine 25-250 mg/day; Opipramol 50-300 mg/day; Tianeptine 12.5-75 mg/day; Trimipramine 25-300 mg/day; and a combination thereof.

Examples of other medications include Atomoxetine 40-100 mg/day (Strattera-selective norepinephrine only reuptake); Bupropion 75q12h or 150-300/day; Busplrone (off-label) 10-30 mg/day in multiple doses; Hypericum perforatum (St.John's wort-off-label) 300-3600 mg/day; Lamotrigine XR 25-200 mg/day; Mirtazapine 7.5-45 mg/day; Trazadone 25-400 mg/day; L-triiodothyronine (off-label) 25-50 micrograms/day; Vilazodone 10-40 mg/day; Dexanabinol (HU-211) 150mg IV (cannabinoid-derived Immune modulator and NMDAR antagonist) Quetlapine (atypical antipsychotic); Ariprazole (atypical antipsychotic; often used in combination with other medications); and a combination thereof.

Commonly used drug combinations include Chlordiazepoxide/Amitriptyline; Fluoxetine/Oianzapine; and Perphenazine/ Amitri, and one or more of the combinations may be employed with compositions of the disclosure Other interventions include Electroconvulsive therapy (ECT)—unilateral or bilateral; Transcranial magnetic stimulation (TMS) or repetitive TMS (rTMS) therapy; Psychotherapy (such as but not limited to problem-solving therapy; cognitive-behavioral therapy; interpersonal psychotherapy; psychosocial interventions (family-focused, interpersonal and social rhythms therapies) and Problem adaptation therapy (PATH), and one or more of the interventions may be employed with compositions of the disclosure.

Exercise therapy (focusing on behavioral activation—a core concept of cognitive-behavioral therapy) may be employed and one or more types of exercise may be employed with compositions of the disclosure.

VI. Pharmaceutical Compositions

Pharmaceutical compositions of the present disclosure comprise an effective amount of one or more compositions as disclosed herein dissolved or dispersed in a pharmaceutically acceptable carrier. The phrases "pharmaceutical" or "pharmacologically acceptable" refer to molecular entities and compositions that do not produce an adverse, allergic or other untoward reaction when administered to an animal, such as, for example, a human, as appropriate. The preparation of a pharmaceutical composition that in some cases contains at least one negative modulator of a $GABA_A$ receptor of the invention, and in some cases an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition(s) may comprise different types of carriers depending on whether it is to be administered in solid, liquid or aerosol form, and whether it needs to be sterile for such routes of administration such as injection. The present disclosure can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), as an aerosol, or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an individual can be determined by physical and physiological factors such as body weight, severity of condition, the type of disease being treated, previous or concurrent therapeutic interventions, and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a composition. In other embodiments, the active compound may comprise between about 2% to about 75% of the weight of the unit, or between about 25% to about 60%, for example, and any range derivable therein. In other non-limiting examples, a dose may also comprise from about 0.1 mg/kg/ body weight, 0.5 mg/kg/ body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above. In certain embodiments of the invention, various dosing mechanisms are contemplated. For example, the composition may be given one or more times a day, one or more times a week, or one or more times a month, and so forth.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The composition may be formulated in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, it will be preferable to include isotonic agents, such as, for example, sugars, sodium chloride or combinations thereof.

Sterile injectable solutions are prepared by incorporating the instant invention in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

VII. Kits of the Disclosure

Any of the one or more negative modulators of $GABA_A$ receptor compositions encompassed herein may be comprised in a kit, and they are housed in a suitable container. The kits will thus comprise, in suitable container means, one or more compositions and, in some cases, an additional agent of the present invention. In some cases, there are one or more agents other than the composition of the disclosure that are included in the kit, such as one or more other agents for the treatment of depression or suicidal tendencies. In particular embodiments, there is an apparatus or any kind of means for the diagnosing of depression and/or suicidal tendencies.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also may generally contain a second, third or other additional container into which the additional components may be separately placed. However, various combinations of components may be comprised in a vial. The kits of the present disclosure also will typically include a means for containing the composition, additional agent, and any other reagent containers in close confinement for commercial sale. Such containers may include injection or blow molded plastic containers into which the desired vials are retained.

Compositions may also be formulated into a syringeable composition. In which case, the container means may itself be a syringe, pipette, and/or other such like apparatus, from which the formulation may be applied to an infected area of the body, injected into the individual, and/or even applied to and/or mixed with the other components of the kit. However, the components of the kit may be provided as dried powder (s). When reagents and/or components are provided as a dry powder, the powder can be reconstituted by the addition of a suitable solvent. It is envisioned that the solvent may also be provided in another container means. The kit may be configured such that it is easily used in or out of a medical facility setting, including in public, in an ambulance, in a home, or in a school, for example.

EXAMPLES

The following examples are presented in order to more fully illustrate the preferred embodiments of the disclosure. They should in no way, however, be construed as limiting the broad scope of the disclosure.

Example 1

Negative Modulator of $GABA_A RS$ in Model for Depression

Using a rodent model of depression with face, construct, and predictive validity, chronic unpredictable stress (CUS), it is shown that the acute administration (24 hrs) of a negative modulator of $GABA_A Rs$ does have an antidepressant-like efficacy in this model. Specifically, a partial inverse agonist of α5 subunit-containing $GABA_ARs$, L-655,708, restores the behavior of rats previously subjected to CUS for 3-6 weeks to the behavior seen in unstressed control rats in both the sucrose preference test and the social interaction tests (Amat et al., 2010; Winner et al., 1987). Consistent with widely held views in the field, the restoration of sucrose preference indicates that the compound has reversed stress-induced anhedonia, a primary symptom of human depression.

In certain embodiments, other α5-selective partial inverse agonists (R04938S81, Ballard et al., 2009; MRK-016, Atack et al., 2009) and a non-selective inverse agonist (FG7142; Shansky et al., 2004) exert similar actions. Consistent with previous findings, there is no evidence of increased anxiety in the open field test with L-655,708. One can determine whether administration of partial inverse agonists of α5 subunit-containing $GABA_A$ receptors can reverse the electrophysiological correlates of stress-induced depression (decreased GluA1 expression, decreased AMPA:NMDA ratios, prolonged responses to 5-HT1BR agonists) that are described elsewhere (Cai et al., 2013; Kallarackal et al., 2013), using electrophysiological and biochemical analyses in vitro.

Given that partial inverse agonists of α5 subunit-containing $GABA_ARs$ exert an antidepressant action in animal studies, comparable to those shown by others for ketamine (Ibrahim et al., 2012), in specific embodiments many other compounds that weaken $GABA_AR$-mediated synaptic inhibition in the forebrain and hippocampus reward circuits demonstrate similar efficacy in a clinical setting in humans. In particular embodiments, the compounds may be orally active and/or self-administered, but could be infused intravenously, for example. In specific embodiments, individuals show an improvement in one or more standard assays of depression, such as the Hamilton Depression Rating Scale, Beck Depression Inventory, and/or the Brief Psychiatric Rating Scale, for example. Antidepressant efficacy, as well as any potential negative side effects, such as psychotomimetic of anxiogenic responses, may be readily apparent from changes in the test scores. One can determine in animals or humans how long the improvement would persist after administration with repeated completion of widely used clinical questionnaires (e.g. Hamilton Rating Scale for Depression, Montgomery-Åsberg Depression Rating Scale etc.), for example.

Example 2

Negative Modulator of $GABA_ARS$ and Treatment of Depression

Depression is a leading cause of mortality and morbidity worldwide. Severe depression affects as much as 5% of the US population, while 20% suffers from milder forms (Nestler et al., 2002). The annual economic burden of depression in the US is billions of dollars. Among the many devastating symptoms of depression, the prevalence of suicide (38,000 deaths/year) makes it a disease in desperate need of more effective therapeutic treatment. Despite its high incidence and socioeconomic impact, the etiology of depression remains poorly understood. Depression likely involves a combination of genetics (Flint and Kendler, 2014; Hamet and Tremblay, 2005) and environmental factors (Nestler et al., 2002). Many genes that increase risk for depression have been identified, but no single gene has strong penetrance.

It is not clear how genetics and environmental factors interact to trigger depression. A common environmental factor that increases the likelihood of depressive episodes is stress. Depressed patients report more stressful life events than non-depressed subjects, including physical illness, troubled family relationships, and financial difficulty (Billings et al., 1983). The nature of the change(s) produced in the brain by stress that promotes depression in susceptible individuals remains unknown.

Antidepressants (ADs). Increasing monoaminergic signaling by inhibiting their reuptake with medications like SSRIs is the present standard of care, but SSRIs are effective in only about half of patients. In addition, the 3-8 week delay between the onset of medication and the therapeutic effect complicates optimization of medication and delays symptomatic relief. A better understanding is needed in order to devise more effective therapies.

The discovery that ketamine exerts a rapid antidepressant action (Trullas and Skolnick, 1990) when administered in a clinical setting has caused great excitement (Berman et al., 2000; Zarate et al., 2006). However, there are concerns that its addictive nature and ability to trigger psychotomimetic episodes (e.g. Machado-Vieira et al., 2009) may prevent it from reaching its potential to save lives and reduce disability. Nevertheless, its ability to rapidly alleviate suicidal ideation and other core depressive symptoms has forced the medical community to rethink the causes of depression and the targets at which to direct antidepressant drugs. As in patients, ketamine administration results in an AD-like behavioral response in rodents subjected to chronic stress (Maeng et al., 2008; Li et al., 2011). Ketamine has also provided a critical mechanistic insight into how rapid AD actions may be produced (e.g. Li et al., 2011; Autry et al., 2011), raising hopes that new drugs can be developed that target the same signaling mechanisms, but lack ketamine's disadvantages and risks.

Excitatory synapses and depression. A common element linking stress with the therapeutic actions of SSRIs (Cal et al., 2013) and ketamine (Kavalali and Monteggia, 2012) is their shared, but opposing, effects on excitatory synapses. There is increasing evidence that chronic stress exerts deleterious effects on excitatory synaptic structure and function in multiple brain regions that are associated with cognition and emotion (McEwen, 1999), whereas ketamine, serotonin, and SSRIs exert an opposing action to promote excitatory synaptic transmission in some of these same areas (Autry et al., 2011; Cai et al., 2013; Kallarackal et al., 2013). In the nucleus accumbens (NAc), for example, Lim et al. (2012) showed that excitatory synapses in D1-expressing medium spiny stellate cells have a selective decrease in AMPAR-mediated excitation after 5 days of chronic restraint stress. This decrease in excitation occurs in parallel with many behavioral changes, including anhedonia in the sucrose preference test and impaired conditioned place preference. Experimental manipulations that cause a decrease in AMPAR-mediated excitation mimic the stress-induced behavioral changes in unstressed animals and manipulations that prevent the decrease in AMPAR-mediated excitation block the behavioral changes in stressed animals, indicating that this decrease in excitation is sufficient and necessary for these behavioral changes. The source of the axons forming these excitatory synapses was not identified, but is likely to include afferents from the hippocampus, prefrontal cortex, and amygdala. Activation of D1-expressing neurons promotes dopamine release from cells in the ventral tegmental area (VTA), so a decrease in their ability to drive dopamine release due to decreased excitation, together with changes in VTA cell firing (Chaudhury et al., 2013), may contribute to the loss of the rewarding properties of normally pleasurable stimuli. Chronic stress also weakens excitatory synapses within the prefrontal cortex (PFC) (Yen et al., 2012) and the hippocampus (Kallarackal et al., 2013), likely reducing afferent drive of the NAc and further decreasing the release of dopamine by rewarding stimuli. Chronic administration of fluoxetine restores the strength of hippocampal synapses and reverses stress-induced decreases in GluA1 expression (Kallarackal et al., 2013).

In embodiments of the disclosure, chronic stress promotes depression by weakening subsets of excitatory synapses in multiple brain regions that are critical in the determination of affect and reward. Depression results because the net effect of the weakened synaptic excitation is to impair activation of reward circuits (e.g. Nestler and Carlezon, 2005). Following this consideration, restoration of excitatory synaptic strength is a critical action of all effective antidepressants, in particular embodiments.

Although it remains under active investigation, ketamine's fast-acting therapeutic action is consistent with the involvement of excitatory synapses in depression (FIG. 1). One hypothesis is that ketamine is somewhat selective for NMDARs on inhibitory interneurons (Moghaddam et al., 1997; Farber et al., 1998; Kavalali and Monteggia, 2012), such that ketamine decreases their excitation. This results in a mild disinhibition of the neuronal population and overall increase in high frequency oscillatory activity in animals (e.g. Kittleberger et al., 2012) and humans (Cornwell et al., 2012). Presumably because of this increase in network activity, ketamine triggers several activity-dependent processes, such as long-term potentiation, increased expression of the immediate early gene deltaFosB, and activation of the mTOR and/or eEF2 signaling pathways. This ultimately leads to the rapid induction of synapse-related genes, increased synthesis of synaptic proteins (Li et al., 2010; Autry et al., 2011), and restoration of normal synaptic strength. These results indicate that it is ultimately the mild increase in global activity in forebrain neural circuits that is a mechanism via which rapid therapeutic AD actions are exerted.

One can test another means of producing such changes, namely mild and selective weakening of the strength of inhibition mediated by gamma-aminobutyric acid type-A receptors (GABARs or $GABA_A Rs$). GABARs are heteropentameric ion channels, containing alpha, beta, and gamma subunits in a 2:2:1 stoichiometry (Sieghart and Sperk, 2002). The interface between a gamma2 subunit and an α subunit forms the benzodiazepine receptor, a positive allosteric modulator of channel gating that increases GABAR function. In addition to benzodiazepine agonists, there are drugs (e.g. beta- carboline) that act as inverse agonists at the benzodiazepine site to decrease GABAR function. The molecular identity of the alpha subunit in the benzodiazepine receptor site determines its pharmacological profile. GABARs containing alpha1 subunits mediate the sedative, anticonvulsant and amnestic effects of benzodiazepines preferentially, whereas GABARs containing alpha2 and alpha3 subunits mediate their anxiolytic effects (Rudolph et al., 1999; Mohler et al., 2002). Partial inverse agonists offer the potential advantage of a wider therapeutic concentration range and a lower likelihood of producing negative side effects, such as anxiety or epileptiform discharge.

Negative allosteric modulators of GABARs containing alpha5 subunits, or alpha5 GABA-NAMs, have been developed recently (Quirk et al., 1996; Atack et al., 2006; 2009). Whereas non-selective benzodiazepine inverse agonists are anxiogenic in humans, alpha5 GABA-NAMs are not. alpha5-subunit mRNA is abundant in pyramidal cells in the hippocampus and cortex (Allen Brain Atlas) and α5-containing GABARs are localized to synaptic and extrasynaptic sites in the dendrites (Fritschy and Mohler, 1995; Wainwright et al., 2000; Serwanski et al. 2006). α5-containing GABARs mediate tonic inhibition and lower the excitability of pyramidal cells (Bonin et al., 2006). Interestingly, α5 subunits are up-regulated in mice after chronic stress (Matsumoto et al., 2007). Because disinhibition promotes induction of long-term potentiation (LTP), the presumptive cellular basis of memory, alpha5 GABA-NAMs are being developed clinically as cognitive enhancers (Ballard et al., 2009). It has been shown, for example, that alpha5 GABA-NAMs increase LTP and enhance memory acquisition in hippocampus-dependent learning tasks (Collinson et al., 2002). Indeed, one alpha5 GABA-NAM compound is already in clinical trials for Down Syndrome. The ability of this class of compounds to promote excitatory drive in regions of the brain like the hippocampus indicates their utility as rapidly acting antidepressants, similar to ketamine but lacking the deleterious side effects.

In embodiments of the disclosure, partial inverse agonists of the benzodiazepine binding site of $GABA_A$ receptors containing alpha5 subunits (L-665,708 and MRK-016) produce a rapid and persistent restoration of a range of behaviors that are impaired by chronic stress in rats and mice because they restore the strength of pathologically weakened excitatory synapses.

One can utilize studies that will challenge and seek to shift the current paradigm for understanding the genesis and treatment of depression. Namely, one can provide a definitive proof-of-concept test of a completely innovative class of potential medications, with potential for rapid implementation in the clinic. The outcome of these studies also tests the consideration that dysfunction of excitatory synapses contributes to the genesis of depression. One can utilize both standard experimental approaches and invaluable existing transgenic mouse models that are well suited to demonstrate effectiveness. One can also employ a variety of chronic stress paradigms with face, construct, and predictive validity with respect to depression and antidepressant development, as well as a battery of behavioral, electrophysiological, and biochemical assays. The studies thus span levels of analysis from behavior to circuits to synapses to molecules, as encouraged by the NIMH's Research Domain Criteria initiative, in order to accelerate the translation of the findings from preclinical research in rodents to human clinical trials.

Depression is a purely human condition, but behavioral changes can be induced in rodents in response to environmental conditions, like chronic stress, that promote depression in humans. Many of the behaviors affected by chronic stress, such as reward, are analogous to human behaviors that are symptomatic of human depression, such as anhedonia. Furthermore, susceptibility to several chronic stress paradigms is associated with genes known to have a high correlation with depression (Hasler et al., 2004). It is important to assess validity in relating the effects of chronic stress in rodents to human depression. The behavioral and electrophysiological phenotypes of rodents subjected to chronic stress paradigms resemble human depression because they 1) include changes in affective state, cognition, and motivation; 2) result from a factor implicated in human depression; and 3) respond to chronic, but not acute, administration of SSRIs (Willner and Mitchell, 2002), as do the symptoms of depressed humans. Understanding how chronic stress affects the brain in rodents reveals insights into the genesis and treatment of human depression.

Chronic stress paradigms. One can use four different chronic stress paradigms in rats or mice to determine whether the effects of the compounds are paradigm-independent. One can employ chronic unpredictable stress (CUS), which involves repeated delivery of mild stressors twice per day for 3 weeks (Wilner et al., 1987). One can use chronic social defeat stress (SDS), a form of psychosocial stress in which animals chronically lose social stature to a more dominant animal (Malatynska and Knapp, 2005). In this paradigm, individual juveniles (>4w old) are placed in the home cage of a dominant resident animal for 1 hr while separated by a perforated protective screen, permitting olfactory, visual and auditory contact. The SDS protocol is repeated daily over 3 weeks. Third, one can use chronic restraint stress (CRS), in which animals are held in tight-fitting restraint tubes for 4h every day for 8-10 days (Lim et al., 2012). Finally, one can directly elevate stress hormone levels by administering corticosterone (Gourley et al., 2008). All of these paradigms induce changes in animal behaviors that are reversed by chronic, but not acute, administration of SSRIs (Papp et al., 1996; Grippo et al., 2006; Bondi et al., 2008), comparable to the 3-8 week delay in patients in response to SSRIs.

Behavioral consequences of stress in rodents. What behaviors in rodents most closely resemble the symptoms of depressed humans and can also best predict effective therapeutic treatments for depression? Ideal signs of a depressive-like state will 1) have ethological relevance, 2) be robust and accurately quantifiable, and 3) be responsive to chronic, but not acute administration of SSRIs, like human depression. The forced swim test and the tail suspension test are considered to provide a measure of behavioral despair. While these tests are popular for their ease of use and reliability, they lack some face validity because changes in these tasks can be detected following a single administration of SSRIs in control animals (Detke et al., 1997; Petit-Demoulier et al., 2005). Another behavioral measure that is affected by chronic stress but is responsive only to chronic, but not acute, SSRIs is an assay of hedonic state called the sucrose preference test (SPT) (Rygula et al., 2006). In this test, rodents are presented with a two bottle choice task with one bottle containing normal water and one bottle containing a dilute sucrose solution. The naturally high preference of rats and mice for the sucrose solution is greatly diminished by chronic stress and restored with chronic, but not acute, SSRI treatment (Pothion et al., 2004). A lack of sucrose preference is said to reveal anhedonia, or the inability to experience reward, a core symptom of human depression. Defects in social reward are also a prominent symptom of human depression. One assay of rodents' social curiosity, the social interaction test (SIT) (Berton et al., 2006), measures the amount of time animals spend interacting with a novel target animal and provides a measure of the rewarding value of social interactions.

The use of these models allows one to reveal a rapid onset of action, which distinguishes embodiments of the present disclosure from the prior art. What has been done previously using animal models is insufficient to have predicted a rapid onset, fast acting antidepressant action of these compounds. Use of other models and methods, such as the forced swim test and tail suspension test, do not provide predictive validity of a fast onset of therapeutic relief of depressive symptoms and suicidal thinking in animals (i.e. humans).

The hippocampus in depression. Depression is likely caused by dysfunction in many brain regions and cell types, including the hippocampus. Glucocorticoid receptors are expressed at high levels in pyramidal cells, rendering it particularly sensitive to stress (Reul & de Kloet, 1985; Magarinos et al., 1996). Indeed, chronic stress induces hippocampal dysfunction, including dendritic atrophy and spine Joss (McEwen, 1999), deficits in synaptic plasticity (Aifarez et al., 2003), decreased neurogenesis and synaptogenesis (Duman and Li, 2012), and aberrant circuitry (Airan et al., 2007). Notably, depressed patients have reduced hippocampal volume and deficits in hippocampus-dependent behavioral tasks (MacQueen et al., 2003; Campbell and MacQueen, 2004) such as visuospatial navigation (Hickie et al., 2005; Gould et al., 2007).

Output from the hippocampus drives activity in the NAc, a key regulator of motivation and reward value, and is known to influence motivation, perhaps through its ability to promote dopamine secretion (Kelley and Mittleman, 1999; Boulenguez et al., 1996; Floresco et al., 2001; Tye et al., 2013). A dialogue between the hippocampus and the neocortex is also important for maintaining normal cognitive function (Gray, 1998; Lisman and Otmakhova, 2001; Morris et al., 1982; Remondes and Schuman, 2004). The entorhinal cortex (EC) provides the principal inputs to the hippocampus, and the projection from area CA 1 to the EC is a principal output. The apical dendrites of CA 1 pyramidal neurons in the hippocampus receive a direct EC input, the temporoammonic (TA) pathway, on their distal apical dendrites in stratum/acunosum molecular (SLM) (Remondes and Schuman, 2002; Steward & Scoville, 1976). The TA pathway is important for consolidation of long-term memory, as well as spatial recognition tasks (Brunet et al., 2002; Remondes & Schuman, 2004). Chronic stress produces a number of changes in TA-CA 1 excitatory synapses and deficits in memory consolidation (Cai et al., 2013; Kallarackal et al., 2013). One can use this synapse as a convenient archetype for the changes that are known to occur at multiple sites in the brain in depression.

Determination of the persistence and generality of alpha5 GABA-NAM's antidepressant actions on behavior.

Figures 3A, 3B:
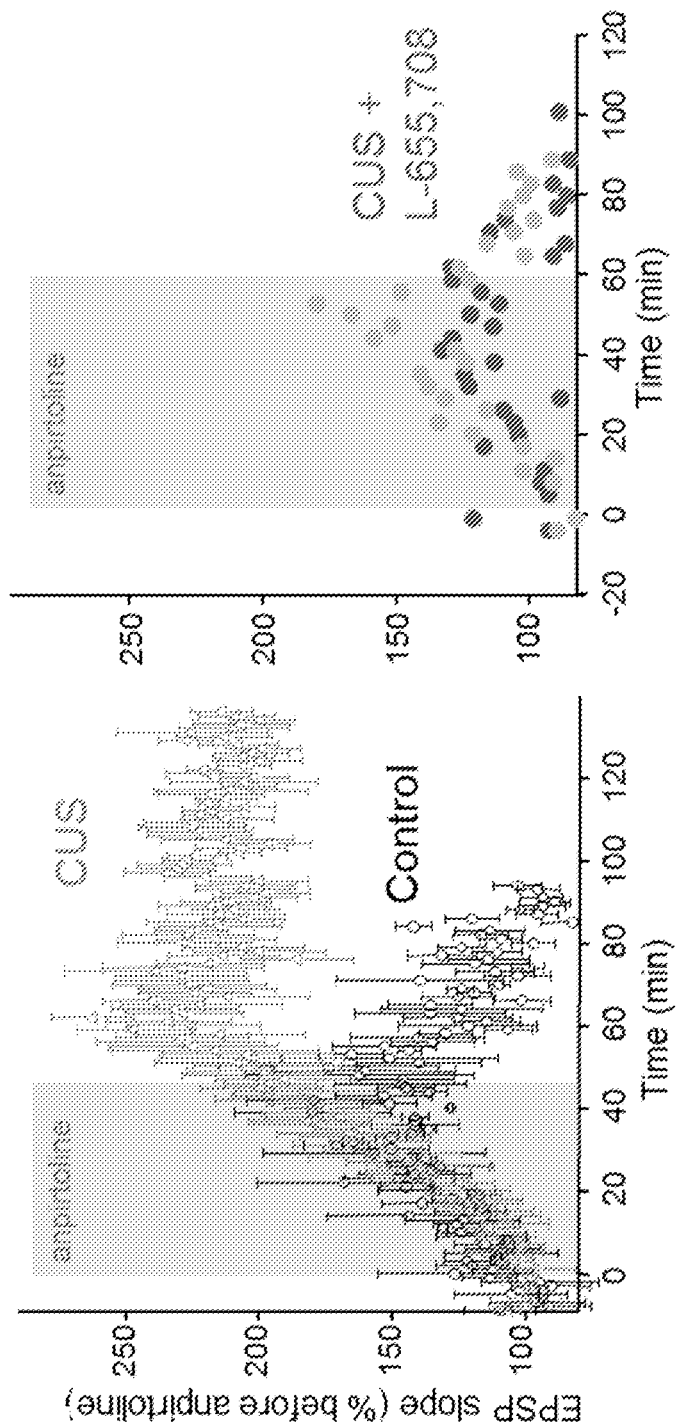
FIG. 3A. In control slices (black), anpirtoline produced a fully reversible potentiation of TA-CA1 EP8P slope of −175%. After CUS (gray), the potentiation was larger and persisted for >60 min after washout.
FIG. 3B, In two slices from CUS rats given an injection of L-655,708 24 hours earlier, the potentiation was similar to controls.
Figure 4:
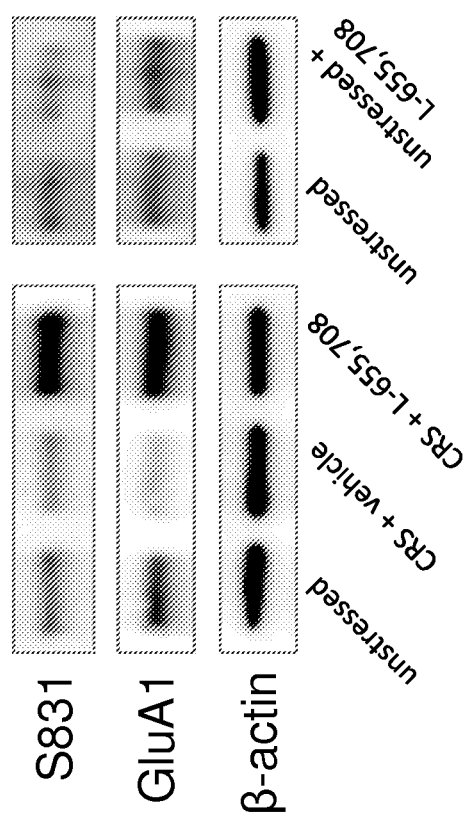
FIG. 4. 24 hours after injection of L-655,708, but not vehicle, phosphorylation of S831 and total GluA1 expression were increased in SLM of hippocampal tissue from CRS rats to levels comparable to unstressed controls. In contrast, L-655,708 had no effect in unstressed animals.

Rationale: A single injection of one of the two commercially available alpha5 GABA-NAM L-665,708 (1 mg/kg, intraperitoneally, IP) (Quirk et al., 1996) reverses the loss of sucrose preference (FIGS. 3A and 3B) and the decrease in social interaction induced by two forms of chronic stress within 24 hrs: chronic unpredictable stress and chronic restraint stress. For this class of compounds to have use as effective ADs in humans, in specific embodiments their restorative effects should 1) hold true over a wide range of behaviors that are affected by chronic stress, 2) be independent of the paradigm by which the stress is applied, and 3) be persistent.

Figures 9A, 9B, 9C:
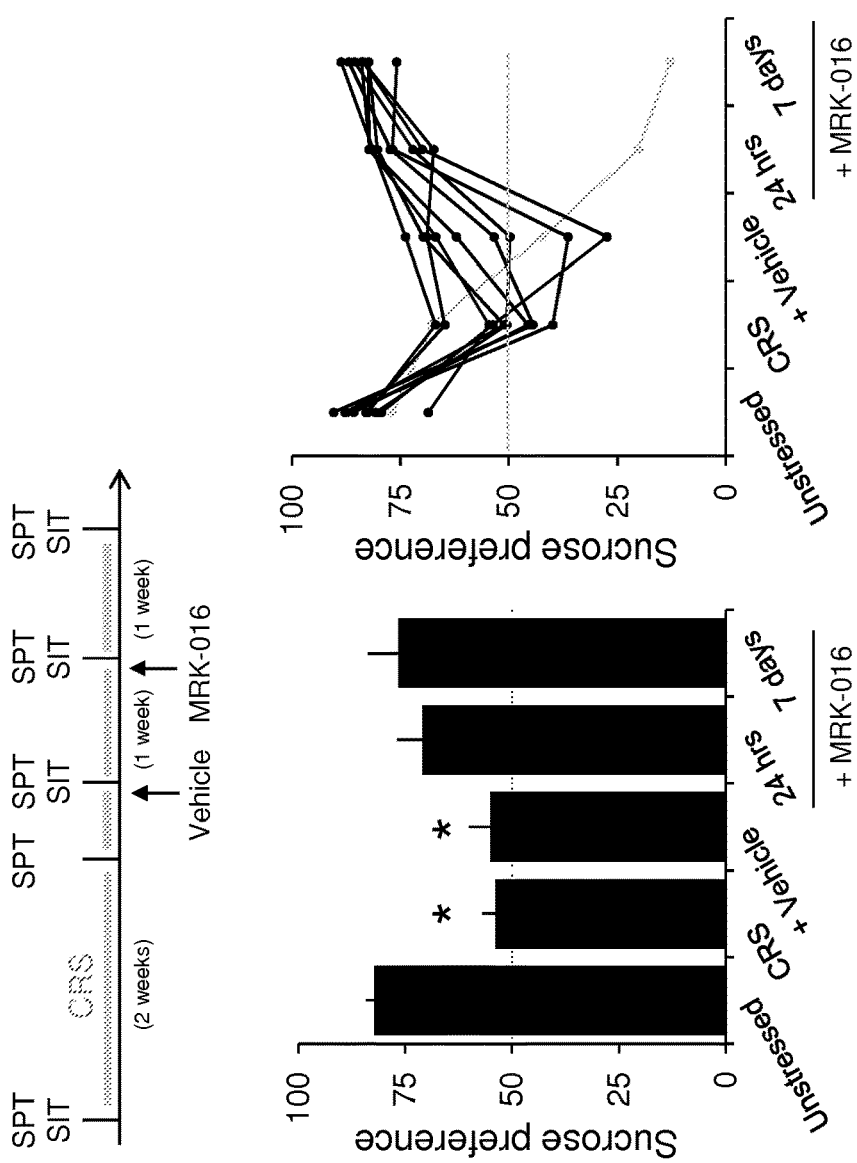
FIGS. 9A, 9B, and 9C. MRK-016 rapidly reverses loss of sucrose preference and social interaction behaviors after chronic restraint stress.

In specific embodiments, a single injection of L-665, 708 or another commercially available alpha5 GABA-NAM, MRK-016 (Atack et al., 2009), at a maximally effective dose rapidly (within days) reverses stress-induced changes in a wide range of behaviors regardless of how the stress is applied, and these effects persist for several days after the injection (FIG. 9).

Definition of control and susceptible animals. As an example, in this and at least some other studies described herein, adult male rats are tested over 2 weeks using the sucrose preference and social interaction tests (SPT, SIT) to establish baselines. Only animals that repeatedly meet pre-established criteria of control rats based on prior results (sucrose preference >75%, social interaction ratio >130%) are considered as acceptable controls. Those that do not are excluded from further study so that a starting population is as homogeneous as possible. Rats are then subjected to one of the chronic stress paradigms, followed by SPT and SIT. At this point, only those animals with sucrose preference <65% and social interaction ratios <115% are considered to have been susceptible to the chronic stress and therefore useful for studying the effects of the test compounds and other manipulations.

Experiment A. What is the alpha5 GABA-NAM dose-dependence? How long do its effects last? One can use the chronic restraint stress (CRS) paradigm for determining dose-dependence. A single injection of L-665,708 or MRK-016 is administered to susceptible rats at doses of 0.3, 1, 3, 10, or 30 mg/kg IP, followed by SPT and SIT<24 hrs later. Dose-response curves are prepared by plotting 1) the mean sucrose preference and social interaction ratio as a function of alpha5 GABA-NAM dose and 2) the percentage of animals that responded to the drug with an increase in sucrose preference to 75% and an increase in social interaction ratio to 130% as a function of dose. Animals are then retested with the SPT and SIT at 5, 10, and 15 days post-injection to determine the persistence of the effects. One set of control group of animals can undergo CRS, receive an injection of vehicle, and be tested with SPT and SIT at 1, 5, 10, and 15 days post-injection. A second set of control animals are not subjected to CRS, but receive an injection of the maximally effective dose of L-665,708 or MRK-016. In specific embodiments, the effects of the compounds are dose-dependent in both behaviors by both measures, and the effects persist for 5-15 days after injection. In specific embodiments, vehicle injection does not restore control responses in either behavior and the compounds do not affect either behavior significantly in unstressed animals. One can use the maximally effective dose of the more effective compound, as determined in these studies, in other studies described elsewhere herein.

Experiment B. How generalized are the restorative behavioral effects of alpha5 GABA-NAMs? One can extend the data on alpha5 GABA-NAM's effects in the SPT and SIT to a broader range of stress-affected behaviors: novelty suppressed feeding, sexual place preference, social hierarchy, and forced swim.

B1. Novelty suppressed feeding (NSF) is a widely used fluoxetine-sensitive measure of chronic stress (Cal et al., 2013). In the first cohort of animals, baseline latency in the NSF test is measured, as done previously. Rats are then subjected to CRS and susceptible animals selected. CRS continues for 5 more days, then half the animals are randomly selected to receive a vehicle injection and the other half receives a single injection of L-655, 708. 24 hrs later they again undergo the NSF test.

B2. Conditioned place preference is a well-established assay of reward valuation and affective state. Therefore, a second cohort of animals undergoes the same procedure but is tested with a sexual place preference test. Control male rats are conditioned to associate sexually receptive females with specific olfactory and visual cues, then given a probe test of environmental preference (Camacho et al., 2004). They are then subjected to CRS and susceptible animals selected. Half of the rats receive vehicle injection and the other half are given an injection of L-665,708. 24 hrs later the place preference probe test is repeated. For both cohorts, two way comparisons are then made between behavioral scores (before vs. after injection×drug vs. vehicle). Mount and intromission latencies, which are known to be sensitive to chronic stress (Gronli et al., 2005), are also measured as indicators of sexual motivation (Hull, 2002). In specific embodiments, only rats receiving L-665,708 display NSF latencies and place preferences that are different from their own scores before injection and different from vehicle-injected rats. Control rats are given NSF or sexual place preference tests. One week later they receive an injection of L-665,708 and are retested 24 hrs later. In specific embodiments, the injections have no effect on either behavior in unstressed control rats, as was observed with SPT and SIT.

B3. Rodents display a prominent innate social hierarchy that is known to be sensitive to chronic stress and is restored by chronic fluoxetine (Lehmann et al., 2013). Urine scent marking, a form of social communication in rodents, correlates with dominance status, with socially dominant rats making more and larger marks than those that are socially subordinate. Another robust test of social dominance, the tube test (Wang et al., 2011), may be used. Control rats are housed in pairs for one week, then given a series of tube tests and a urine marking test to identify the dominant and subordinate rat in each pair. Dominant animals are then subjected to 10 days of CRS, tested for sucrose preference to identify susceptible individuals, then given sucrose preference, urine marking, and tube tests. In specific embodiments, dominant animals lose their dominance as a consequence of stress. If so, one can administer an injection of L-665,708 or vehicle. In specific embodiments, dominance is restored by alpha5 GABA-NAM, but not vehicle, injection in parallel with sucrose preference. Controls are treated as above, but not subjected to CRS. 24 hrs later they are retested in the sucrose preference, urine marking, and tube tests.

B4. A third cohort of control rats receive an injection of L-665,708 or vehicle then undergo forced swim tests 1 hr later. Statistical comparisons of time spent immobile are made between vehicle and drug injected animals. Acute ketamine reduces immobility time in the forced swim test (Maeng et al., 2008), much like acute fluoxetine administration, indicating that the alpha5 GABA-NAM compounds also decrease immobility in this test.

Experiment C. Does alpha5 GABA-NAM induce adverse behavioral effects? Two complex behaviors that might be affected adversely by benzodiazepine inverse agonists are tested: anxiety and sleep.

C1. One cohort of control rats are given a baseline open field test. One week later, half of the animals receive an injection of L-665,708 or vehicle, followed 24 hrs later by a second open field test in a new arena. In a specific embodiment, a mixed design analysis of variance reveals no difference of either alpha5 GABA-NAM or vehicle injection on the amount of time spent in the center zone, an indicator of anxiety, or in total line crossings, an indicator of locomotion, compared to either their own baseline or across groups.

C2. A second cohort is tested for altered daily activity rhythms, as an initial indicator of altered sleep. Rats are housed singly in a cage with multiple crossed infrared beams (SmartCage, Afasci, Inc). Frequency of beam breaks is recorded continuously over a 48 hr-period prior to an injection of L-665,708 or vehicle. Activity is then recorded over the following 48 hrs. Total number of beam breaks and the duration of periods of inactivity are compared in individual animals before and after injection, and between treatment and vehicle groups in another mixed ANOVA.

Experiment D. Can alpha5 GABA-NAMs reverse the effects of multiple stress paradigms? One can complete initial studies with CRS and CUS and extend them to rats subjected to social defeat stress (SDS) (Papciak et al., 2013) and direct corticosterone administration (Gourley et al., 2008).

D1. One cohort of controls experience social defeat daily for 1hr each day for 3 weeks.

D2. Another cohort of controls receives corticosterone hemisuccinate (50 pg/ml) via the drinking water in their home cage for 4 weeks, to produce elevated blood concentrations correlating with the animals' diurnal cycle. Previous studies have shown that peak levels are comparable to those elicited in rats during chronic stress procedures (Gourley et al., 2008). Susceptible rats in each group then undergo another week of SDS or corticosterone administration. Half of the rats in each group receive an injection of L-665,708 and half vehicle. 24 hrs later they again undergo SPT and SITs. Within- and between-subjects statistical comparisons of sucrose preference and social interaction ratios are made for individuals before and after vehicle or drug injection in a mixed design ANOVA. In specific embodiments, injection of the test compound, but not the vehicle, produces a significant change in the animals' sucrose preference and social interaction ratios in both SDS and corticosterone-treated rats.

In cases wherein one needs to detect small differences in behaviors in response to stress or alpha5 GABA-NAM administration, studies may be designed with standardized starting behaviors and evidence of susceptibility so as to reduce variability due to unknown events during the breeding and delivery of animals, resilient individuals, etc. The studies may also be designed to allow use of repeated measures and paired comparisons wherever possible, thus increasing the ability to detect small effects. Initial experiments on the effect of CRS and alpha5 GABA-NAM treatment gave robust effect sizes for the SPT and SIT (f=0.73 and f=0.43, respectively). Using the smaller SIT effect size, and a.=0.05, 8 animals/group are required to have a 95% chance of observing significant differences in future SPTs in a mixed-design ANOVA format (calculated with G*Power and IBM SPSS software). These group sizes are consistent with prior experience and published results for similar experiments (i.e. Lim et al., 2012). Stress effects on social dominance in rats have not been demonstrated, but it is adversely affected in mice and restored by fluoxetine (Lehmann et al., 2013). If dominance is not achieved with CRS in rats, then the studies are performed in C57BL6/J mice, as in earlier published work.

Upon completion of the aforementioned studies, one establishes whether alpha5 GABA-NAM antidepressant-like restorative actions on stress-sensitive behaviors are highly generalizable across a range of the motivational behavioral phenotype (feeding, social, sexual) and whether they are independent from the means in which the stress was applied (direct vs. physical vs. social). In specific embodiments, a useful antidepressant compound is broadly effective, regardless of the proximate cause of the altered behavior, and has few side effects.

Determination of the mechanism of action of alpha5 GABA-NAM at the level of synaptic circuits.

Rationale: Ketamine induces a rapid increase in neural oscillations in circuits in the hippocampus, entorhinal cortex, NAc, and PFC in rodents (e.g. Kittleberger et al., 2012; Middleton et al., 2008; Hunt et al., 2011) and in humans (Driesen et al., 2013). It is widely accepted that this increase in circuit activity underlies the induction of ketamine's antidepressant-like actions because oscillatory activity at these frequencies promotes not only LTP (e.g. Huerta and Lisman, 1993) but also other forms of activity-dependent strengthening of excitatory synapses that are critical to the reversal of the stress phenotype. One can examine whether alpha5 GABA-NAM's ability to reverse the stress phenotype results from triggering similar oscillatory activity.

In specific embodiments, alpha5 GABA-NAMs bind to benzodiazepine receptors to induce rapid activation of neural circuits in the reward circuitry and restore stress-altered behaviors because of their ability to activate activity-dependent synaptic plasticity.

Experiment A. Does alpha5 GABA-NAM administration produce activation of neuronal circuits in vivo as a result of binding to benzodiazepine receptors? Rats have electrodes placed stereotaxically into str. pyramidale of area CA1 (the output of the hippocampus), layer II of the entorhinal cortex (source of the temporoammonic pathway), or the shell of the NAc. After recovery, they are trained to remain still in a plastic tube without anesthesia with their heads secured.

A1. A 60 min period of continuous recording of spontaneous field potential activity is made under dim illumination. Rats are then injected with either L-665,708 or vehicle, and placed back in the tube for an additional 60-90 min of recording. Discrete fast Fourier transforms are made on 60s-long recording segments for preparation of spectrograms. Oscillation power (area under the curve) is integrated for different frequency bandwidths for power spectral density plots ($\Theta$=3-7 Hz; $\alpha$=8-12 Hz; $\beta$=13-29 Hz; $\gamma$=30-80 Hz) (Buhl et al., 1998; Raver et al., 2013). Just as with ketamine (e.g. Kittleberger et al., 2012; Lazarewicz et al., 2010; Hinman et al., 2013), in specific embodiments increases in power are observed by pairwise comparison of spectra before and after drug injection. Initial studies are consistent with this consideration (FIG. 2).

A2. One can next test whether alpha5 GABA-NAMs exert their influence on activity through binding to the benzodiazepine site on the GABAR. The experiments above are repeated in a second cohort of animals with the co-injection of the pharmacological antagonist of the benzodiazepine receptor, flumazenil (20 mg/kg IP) (Tietz et al., 1999), 30 min prior to L-665,708 injection. In specific embodiments, L-665,708 produces no significant change in oscillatory activity under these conditions because it cannot bind to the GABAR.

Experiment B. Do alpha5 GABA-NAMs actions depend on serotonin signaling? One way in which alpha5 GABA-NAM-induced oscillatory activity might restore stress-altered behavior is by promoting serotonin release from raphe neurons.

Bi. One can use Pet1cre-Lmx1bflox mice (Zhao et al., 2006), in which adults lack any serotonergic neurons in the CNS, to characterize this. Surprisingly, these mice have not yet been characterized in many depression-related behaviors, but it is possible that these behaviors are abnormal. One can first characterize these mice in the SPT and SIT. If their behavioral responses are within the same range as wild type littermate mice, then one can subject them to 10 days of CRS. One week later, they receive a single injection of L-665,708 or vehicle, followed 24 hrs later by a second round of SPT and SIT. In specific embodiments, alpha5 GABA-NAMs restorative action on these behaviors is independent of serotonin release and serotonin receptor activation. In specific embodiments, L-655,708 triggers an increase in both measures so that they are different compared to levels before drug injection in repeated measures comparisons, whereas in certain embodiments vehicle-treated animals do not have different measures in a mixed ANOVA design. If these mice do not have sucrose preferences >75% and social interaction ratios >130%, then one does not pursue the experiments further.

B2. One can select control and CRS susceptible rats. Half of the susceptible rats are injected twice with the toxin PCPA (300 mg/kg., IP, 24 hrs apart) (Dewar et al., 1992) to deplete serotonin acutely. The other half is injected with saline. 24 hrs after the second PCPA injection, both sets of rats are given a single injection of L-665,708. 24 hrs later they are given SPT and SITs. Animals are sacrificed and sections stained with an antibody against serotonin to verify PCPA-induced serotonin depletion, as has been done previously (Cai et al., 2013). If alpha5 GABA-NAMs act independently of serotonin, in specific embodiments both PCPA- and saline-injected rats show normalization of stress-sensitive behaviors in response to alpha5 GABA-NAM treatment.

Experiment C. Do alpha5 GABA-NAM's actions depend on NMDAR-dependent plasticity or GluA1 phosphorylation? Ketamine's actions probably depend on blockade of interneuron NMDARs, with the subsequent increase in activity driving strong activation of pyramidal cell NMDARs. One can now test whether alpha5 GABA-NAM converges on this latter effector mechanism (FIG. 1).

C1. One can use CxNR1KO mice (Iwasato et al., 2000), in which NMDARs are genetically deleted in hippocampal and cortical pyramidal cells. These mice are also uncharacterized in many depression-related behaviors and it is possible that these behaviors are abnormal (see however: Rompala et al., 2013). One can first characterize these mice in SPT and SIT. If their behavior responses are within the same range as wild type littermate controls, then one can subject them to 10 days of CRS and repeat SPT and SITs. After an additional 5 days of CRS, they receive a single injection of L-665,708 or vehicle, followed 24 hrs later by a third round of SPT and SIT. In specific embodiments, alpha5 GABA-NAM's restorative action on these behaviors is dependent on pyramidal cell NMDAR receptor activation and therefore, in the absence of these NMDARs, alpha5 GABA-NAMs are unable to restore stress-induced behavioral changes. Paired comparisons in either alpha5 GABA-NAM—or vehicle-injected rats reveal no significant differences in sucrose preference or social interaction compared to before injection, in specific embodiments. If these mice do not display responses in the normal range of responses in SPT and SIT under control conditions, then one can administer a single injection of L-665, 708 or vehicle at the maximal dose, followed by a second round of SPT and SIT 24 hrs later. In specific embodiments, their behavior is not significantly different in either test after injection, If alpha5 GABA-NAM is effective in the CxNR1KO mice; in which NMDARs in the NAc are not deleted, then in specific embodiments activation of inputs from the cortex and hippocampus by alpha5 GABA-NAM are crucial in its AD-like actions.

C2. One can next use S831A mice in which serine 831 of the GluA1 subunit of the AMPAR has been mutated to alanine, rendering them incapable of being phosphorylated by CaM kinase. Previous studies have shown that NMDAR-dependent L TP is abnormal in these mice (Lee et al., 2010). These mice have a behavioral phenotype that resembles that produced by chronic stress, although social interaction was not yet tested. One can therefore give baseline SPT and SITs to naive mice. Because in particular embodiments their responses are not in the normal range in these tests, 5 days later one can give a single injection of L-665,708 or vehicle, followed by a second round of SPT and SIT 24 hrs later. In specific embodiments, their behavior is not significantly different in either test. Hippocampal brain slices may be harvested upon completion for electrophysiological and biochemical analyses, as described below, to test correlations between behavior and synaptic function.

In specific embodiments, alpha5 GABA-NAM's antidepressant-like restorative actions on stress-sensitive behaviors 1) are induced by a benzodiazepine receptor-dependent increase in oscillatory circuit activity and 2) require NMDAR-dependent activity-dependent strengthening of excitatory synapses for their expression.

Determination of the molecular and synaptic mechanisms of alpha5 GABA-NAM action.

Rationale: The inventors and others have observed a weakening of specific excitatory synapses after chronic stress and in specific embodiments this contributes to the genesis of depression. Chronic fluoxetine administration reverses these deficits and in specific embodiments these effects underlie the restoration of normal behavior by effective ADs. Qualitative and quantitative changes in the response of TACA 1 synapses to activation of 5-HT18Rs following chronic stress, which are reversed by AD treatment (Cai et al., 2013), are described. Here one can test the effects of alpha5 GABA-NAMs on these stress-induced phenotypes. The TA-CA1 synapse can be used as an archetype for changes that may occur in multiple brain regions. One can also begin to identify the signaling pathways through which these changes are mediated.

The rapid reversal of stress-induced changes in behavior by alpha5 GABA-NAMs, as described above, is accompanied by a rapid 1) strengthening of AMPAR-mediated excitatory synaptic transmission, 2) normalization of 5-HT1BR-mediated synaptic potentiation, and 3) increase in GluA1 expression levels.

Experiment A. Do alpha5 GABA-NAMs restore AMPAR-mediated synaptic responses? Control and CRS-susceptible rats are given a single injection of L-665, 708 or vehicle, followed 24 hrs later by a second round of SPT and SIT. Hippocampal brain slices are then prepared for electrophysiological recording. Because TA-CA1 synapses are electrotonically remote from CA 1 cell somata, one can use extracellular recording of local field excitatory postsynaptic potentials (fEPSPs) in SLM. AMPAR-mediated responses are compared using two independent methods (fiber volley amplitude and NMDAR-mediated responses) to control for the intensity of stimulation and the health of the slices, as has been done previously (Kallarackal et al., 2013). One can first normalize AMPAR responses to the amplitude of fiber volley over a range of stimulation intensities. One can also normalize responses by comparing the slopes of the AMPAR- and NMDAR-mediated components at a modest stimulation intensity producing fiber volleys of −0.2 mV before and after application of DNQX. Schaffer collateral responses are measured as a control because they are not affected by chronic stress by this measure (Kallarackal et al., 2013). In specific embodiments, AMPAR-mediated excitation is decreased in slices from vehicle-injected CRS rats compared to unstressed, vehicle-injected controls. Injection of alpha5 GABA-NAMs restores control levels of excitation in slices from CRS rats, but has no effect in control rats. This is what has been observed in initial studies (FIGS. 10A, 10C).

Experiment B. Do alpha5 GABA-NAMs restore 5-HT1BR-mediated potentiation? One can consider whether alpha5 GABA-NAMs reverse another phenotypic alteration of stressed TA-CA 1 synapses: amplification and persistence of responses to the 5-HT1BR agonist anpirtoline (FIG. 3A) (Cai et al., 2013). Slices are prepared from the four groups described in Experiment A. Anpirtoline (501.1M) is bath applied for 60 min, followed by a 90 min washout period. In specific embodiments, anpirtoline potentiation of TA-CA1 fEPSPs is of a larger magnitude and is persistent in slices from vehicle-injected CRS animals compared to unstressed, vehicle-injected controls and that injection of alpha5 GABA-NAM restores control levels of reversible potentiation in slices from CRS rats, but has no effect in control rats (see FIG. 3B).

Experiment C. Do alpha5 GABA-NAM restore GluA1 phosphorylation and/or expression? Tissue punches are obtained from the SLM region (where the stress-sensitive TA-CA1 synapses are) in the slices prepared for Experiment A. Control punches are taken from str. radiatum (where the stress-insensitive Schaffer collateral synapses are). Western blotting is used to compare expression of GluA1 and S831 phosphorylation, GluA2, PSD-95, and NR1, as has been done previously (Cai et al., 2013; Kallarackal et al., 2013). In specific embodiments, expression of GluA1 and PSD-95, but not GluA2 or NR1, is decreased in the SLM in vehicle-injected CRS animals compared to unstressed, vehicle-injected controls and injection of alpha5 GABA-NAM increases GluA1 S831 phosphorylation and restores control levels of expression in CRS rats, but has no effect in control rats (see FIG. 3).

Experiment D. What signaling pathway does alpha5 GABA-NAM activate to mediate its beneficial actions?

D1. Duman and colleagues (Li et al., 2011) showed that ketamine increases expression of several genes associated with synaptic function through rapid activation of the mTOR signaling pathway. One can use the same approach to test the role of this pathway in alpha5 GABA-NAM's actions. Cannulae are positioned in the cerebral ventricles. One week later, CRS-susceptible rats are identified. Rats are then divided into three groups. Group one receives rapamycin (0.2 nmol, ICV) 30 min prior to an injection of L-665,708, group two receives saline ICV 30 min prior to an injection of L-665,708, and group three receives rapamycin ICV prior to an IP injection of vehicle. 24 hrs later they are retested in SPT and SITs. If mTOR signaling is required for the effects of alpha5 GABA-NAMs, then in specific embodiments pairwise comparisons show that alpha5 GABA-NAM +saline rats have increased sucrose preference and social interactions as compared to before injection, whereas the alpha5 GABA-NAM+rapamycin and vehicle+rapamycin rats do not. Rats are then sacrificed for electrophysiological and biochemical analyses, as above. In specific embodiments, the restorative alpha5 GABA-NAMs-induced synaptic and biochemical changes observed in Experiments A-C are also blocked by rapamycin. One can also use Western blotting to look for increases in phospho-mTOR and BDNF after alpha5 GABA-NAM injection in the NAc, area CA1, EC, and PFC.

D2. Kavalali and Monteggia (2012) have advanced an mTOR-independent model of ketamine action in which inhibition of NMDARs de-phosphorylates eukaryotic elongation factor eEF2, allowing rapid de-suppression and translation of dendritic mRNAs, including BDNF. One can use the same approach to test this mechanism of alpha5 GABA-NAM action. Control and CRS-susceptible rats are given an injection of L-665, 708. One hour later, rats are sacrificed and tissue harvested. Tissue punches are taken from the NAc, area CA 1 (separating dendritic and somatic layers), the EC, and the PFC and subjected to Western blotting for quantification of BDNF and phosphorylated and total eEF2 expression, as in Autry et al. (2011). If dephosphorylation of eEF2 contributes to alpha5 GABA-NAM's actions, then in specific embodiments phosphorylated eEF2 decreases and BDNF increases in tissue from alpha5 GABA-NAM-injected rats, compared to tissue from vehicle-injected rats. In the hippocampal samples, the changes in phospho-eEF2 and BDNF are greater in dendritic tissue than in somatic tissue.

Figure 5:
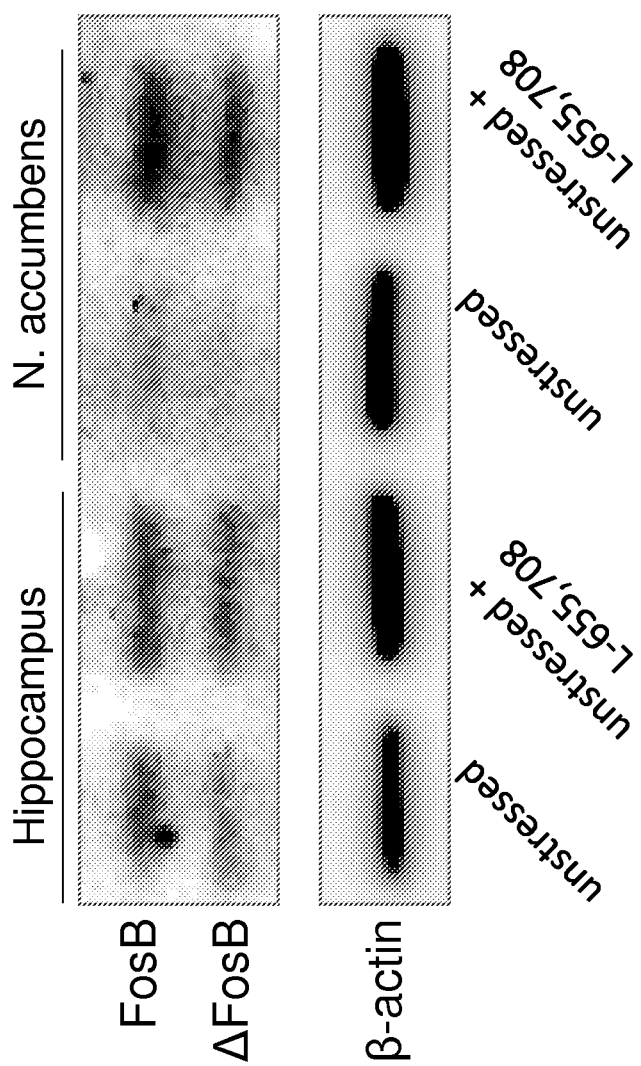
FIG. 5. One hour after injection of L-655,708 there was an increase in expression of FosS and ΔFosB in unstressed animals in the NAc but not in the hippocampus. No changes were apparent 24 hrs after injection.

D3. Nestler and colleagues have shown that induction of the transcription factor ΔFosB in D1R-expressing medium spiny neurons in the NAc in response to chronic stress is an important mediator of resilience and may play a role in the antidepressant actions of fluoxetine by changing gene expression and synaptic strength (Perrotti et al., 2004; Lobo et al., 2013; Grueter et al., 2013). It is considered whether alpha5 GABA-NAM injection also affects deltaFosB expression. Control and CRS-susceptible rats receive an injection of L-665, 708. One hour later, rats are sacrificed and tissue harvested. Tissue punches are taken from the NAc, area CA1, EC, and PFC and subjected to Western blotting for quantification of deltaFosB levels. Sections are prepared from these same regions and stained for ΔFosB in order to count immunoreactive nuclei with stereological techniques (Vialou et al., 2010). Sections through the ventral striatum are co-stained with an antibody against the D1R, since the expression of ΔFosB in these cells may be particularly important for SSRI actions (Lobo et a/., 2013). Similar to fluoxetine, in specific embodiments in stressed and unstressed animals, alpha5 GABA-NAM affects ΔFosB expression in the NAc and other brain regions, consistent with initial studies (FIG. 5).

With regard to the sensitivity of the assays, power analysis based on previously published data on the effects of GUS on AMPAR:NMDAR ratios (Kallarackal et al., 2013) suggests that detection of an effect size with p=0.6 would require a total n=21 to have 0.95 power. These studies are designed to establish a correlation between restoration of stress-induced behavioral and synaptic phenotypes. Such an initial step may lead to more synapse- and behavior-specific studies, and one can then characterize other synapses electrophysiologically and biochemically, particularly in the NAc. The results of the studies on signaling pathways are valuable in designing effective experimental interventions, such as targeted knockdown and overexpression of deltaFosB (Grueter et al., 2013), to establish causality.

Thus, it is determined whether alpha5 GABA-NAM's rapid reversal of stress-induced behavioral phenotype is accompanied by rapid changes in the stress-induced synaptic phenotype. One can also identify the signaling pathways through which these changes are mediated.

It is determined that partial inverse agonists of the benzodiazepine site of GABARs containing α5 subunits (for example) have antidepressant efficacy. In one embodiment, stress-induced synaptic changes cause stress-induced behavioral changes. In other embodiments, there is mapping of specific synapses affected by stress and the corresponding behavioral consequence of that dysfunction, such as the correlation between TA-CA1 synaptic strength and memory consolidation (Kallarackal et al., 2013).

In specific embodiments, one tests whether 5-HT1BR-induced potentiation and activity-dependent synaptic plasticity share common signaling mechanisms at TA-CA1 synapses. 5-HT1BRs potentiate TA-CA1 synapses by a strengthening of postsynaptic AMPAR responses mediated by phosphorylation of AMPARs by CaMK (Cal et al., 2013). Another parallel signaling pathway, involving ras and activation of ERK, is also activated. Inhibition of ERK blocks 5-HT1BR-mediated potentiation by preventing CaMK from being able to phosphorylate GluA1Rs.

One can determine how potentiation of TA-CA 1 synapses by 5-HT1BRs is enhanced after GUS. The magnitude of 5-HT1BR-induced potentiation at TA-CA1 synapses is greater after CUS and in specific embodiments this was because of a low initial strength of excitatory synapses (Cai et al., 2013). This was confirmed with electrophysiology and biochemistry (Kallarackal et al., 2013). 5HT1BR-mediated potentiation is also persistent in slices from CUS animals, unlike controls, and this is mediated by a persistent phosphorylation of S831 of GluA1Rs. In specific embodiments, phosphorylation of S845 in GluR1 subunits iss critical and. One can compare changes in S845 phosphorylation in control and CUS tissue. Administration of corticosterone is necessary and sufficient to mimic both of these consequences of CUS.

One can determine why potentiation of TA-CA1 synapses by 5-HT1BRs is absent after chronic SSRI treatment. Long-term SSRI treatment abolishes 5-HT1BR-induced potentiation (Cai et al., 2013). There is no evidence that chronic fluoxetine treatment in non-CUS animals caused upregulation of AMPARs or persistent increases in synaptic strength, indicating that the lack of serotonin responses in animals chronically treated with SSRis is not due to prior maximization of synaptic strength. One can study changes in the activation of various second messenger pathways for evidence of disruptions that can explain the results. LTP is absent in naive rats given fluoxetine, suggesting that CaMK activation may be impaired.

One can determine whether activation of 5-HT1BRs and potentiation of glutamatergic synapses are necessary for the behavioral therapeutic effects of ADs. SSRIs cannot reverse stress-induced anhedonia if 5-HT1BRs are blocked pharmacologically or knocked out. Furthermore, SSRIs cannot reverse anhedonia in GluA1 S831A mice, implicating serotonin-mediated potentiation. S831A transgenic mice, but not 5-HT1BR knock-out mice, were anhedonic even in the absence of CUS, supporting a model of depression in which cognitive and emotional disturbances result from a dysfunction of excitatory synapses, rather than a dysfunction of serotonergic signaling (Cai et al., 2013; Kallarackal et al., 2013).

GENERAL METHODS. All studies are performed, and all data are analyzed, with the experimenter 'blinded' to the drug treatment, genotype, or behavioral protocol used. Unless otherwise noted, male Sprague-Dawley rats of 4-6 weeks old are used.

Electrophysiology in vitro. Performed as in Kallarackal et al. (2013). For AMPA:NMDA ratios, $Mg^{2+}$-free saline is used to produce a robust NMDAR-mediated response. AMPA responses are quantified as the initial rising phase of the response (FIG. 10A). NMDA responses are determined after application of DNQX (50 µM).

Electrophysiology in vivo. Tungsten microelectrodes (tip impedances=0.5MΩ) are implanted stereotaxically in str. pyramidale of area CA 1, layer II of the EC, layer V of the medial PFC, or the shell of the NAc and secured to the skull with cement. After implantation, rats will be habituated to stay still under light restraint (a metal pole connecting the headstage to a rigid arm) in a narrow tube. On-going electrical activity will be recorded in the absence of anesthesia. Field potentials will be analyzed using Spike2 software.

Western blotting. Performed as previously (Kallarackal et al., 2013) with commercial antibodies.

Chronic unpredictable stress and social defeat stress is as described in Cai et al. (2013).

Chronic restraint stress. Animals are placed in tight fitting restraint tubes and set in cages with normal bedding in room light for 4 hrs daily over 10 days (Lim et al., 2012), then returned nightly to their home cages.

alpha5 GABA-NAM L-655,708 and MRK-0106 (Tocris) are dissolved in DMSO and then diluted in saline for injection.

Sucrose preference and novelty suppressed feeding tests were as described in Cai et al. (2013).

Social interaction test. Test rats are first placed alone for 3 min in an arena with a small holding pen at one end empty, then removed for 60 min and placed back in the arena with a novel juvenile rat in the holding pen.

Video recordings are made of the position of the rat in the arena and then analyzed post-hoc to compute an interaction ratio, defined as the ratio of the time the rat spends in an 'interaction zone' near the holding pen with the juvenile present and absent (Berton et al., 2006). Multiple SITs are performed >5 days apart.

Sexual conditioned place preference. Rats are first given a pretest, 3 weeks of conditioning, and then a preference test (Camacho et al., 2004). In the test sessions, each rat is placed in the middle compartment, and the time spent in 2 side compartments, each with unique visual cues and bedding, is measured over 30 min to determine side preference. Three times per week for 3 weeks, males are then placed in the preferred compartment for 30 min directly from their home cage with a receptive female (ovariectomized and given 10mg estradiol benzoate and 2 mg progesterone, 48 and 4 h before tests) until ejaculation. Latency to the first mount and to intromission are scored. 48 hrs after the last copulation, preference is tested as above.

Tube test. Rats are housed as pairs and receive 2 training sessions in which they are placed at one end of a 1m long, 5cm diameter tube, with a food reward at the far end. Ten times per day for 5 days, they are placed at opposite ends of the tube. The rat that comes out at the opposite end of the tube is declared the winner. A score is assigned to each rat in the pair based on the number of aggregate wins. Only pairs in which one rat wins>75% of trials are considered to have a sufficiently strong dominance to test the effects of CRS.

Urine scent marking. Rat pairs are placed in opposite sides of a cage divided by a screen with sheets of filter paper underneath. Dried sheets are stained with ninhydrin, which stains amines in urine, and photographed. The number and area of the marks are quantified using ImageJ (Lehmann et al., 2013).

Forced swim test. Rats are placed in a 50 cm diameter tank filled with room temperature water. The duration of immobility during the last 4 min of the 6-min test is scored (Maeng et al., 2008).

Figure 8:
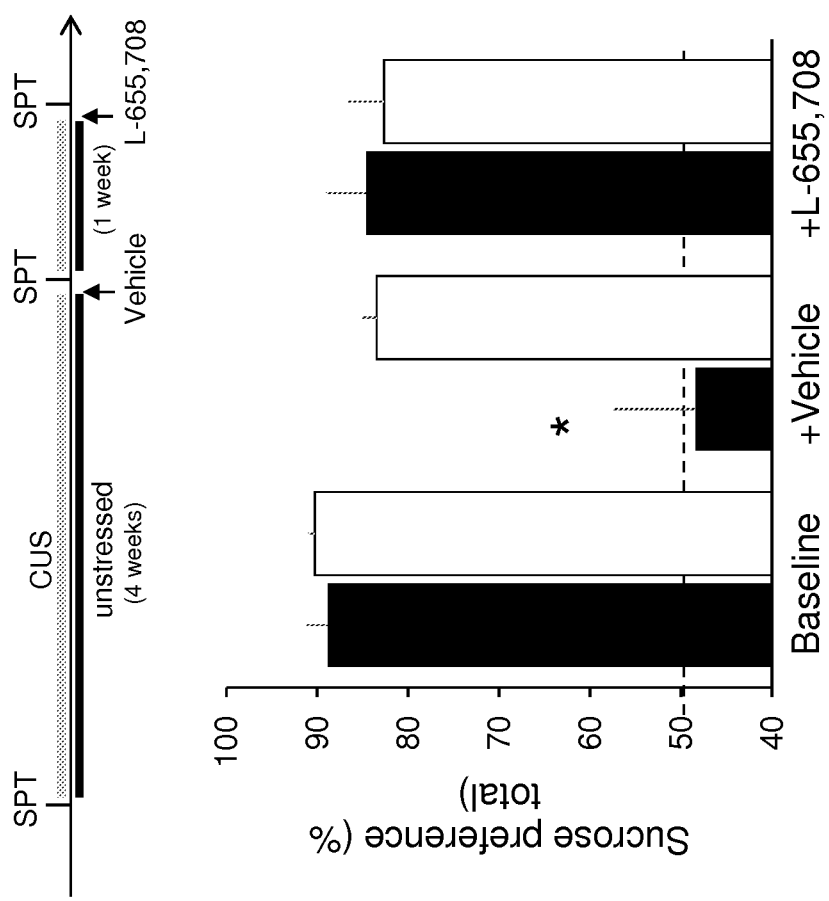
FIG. 8. Mean sucrose preference following 4 weeks of CUS+vehicle injection differed significantly from all other groups, (3×2 repeated-measures ANOVA group-time interaction $F(2,18)=12.309$, $p=0.006$; *$p<0.05$ vs all other groups, Bonferroni test) N=5 CUS rats and N=7 unstressed rats. The left bar of the pairs (black) reflects CUS rats and the right bar of the pairs (white) reflects unstressed rats.

Sucrose preference test. Rats are administered a sucrose preference test before chronic unpredictable stress or no stress. The left bar of the pairs (black) reflects CUS rats and the right bar of the pairs (white) reflects unstressed rats. After 4 weeks, mean sucrose preference following 4 weeks of CUS+vehicle injection was significantly lower than the unstressed group, indicating anhedonia, (FIG. 8. 3×2 repeated-measures ANOVA group-time interaction $F(2,18)=12.309$, $p=0.006$; *$p<0.05$ vs all other groups, Bonferroni test) N=5 CUS rats and N=7 unstressed rats. After another week of stress, rats treated with L-655,708 24 hours earlier had a restored sucrose preference, indicating antidepressant action. Unstressed rats did not have significantly different sucrose preference after 4 or 5 weeks of no stress.

MRK-016 rapidly reverses loss of sucrose preference and social interaction behaviors after chronic restraint stress (FIG. 9). After two weeks of chronic restraint stress, rats had a reduction in sucrose preference, which was not reversed after vehicle treatment ($F(3,33)=20.63$, $p<0.0001$, n=12 rats, p<0.05 compared to pre-CUS baseline, Tukey's post-hoc test). 24 hours after treatment with MRK-016, sucrose preference was not significantly different than the baseline before stress exposure, and this effect persisted for 7 days. Similarly, social interaction scores decreased significantly after chronic stress and vehicle treatment (F=(2,14)=11.84, p=0.0009, n=8 rats). *, p<0.05 compared to pre-CUS baseline, Tukey's post-hoc test). However, 24 hours after MRK-016 (3 mg/kg) treatment social interaction scores were not significantly different than the pre-stress condition, indicating rapid antidepressant action. This persisted for 7 days despite further stress exposure. and in the same animals after an additional week of CRS and 7 days after the injection of MRK-016.

Example 3

Alpha5-selective negative allosteric modulators of GABAA receptors exert a rapid antidepressant action and restore stress-induced impairment of excitatory synaptic strength Overview Selective serotonin reuptake inhibitors (SSRIs) are the first line of pharmacological treatment for depression, but SSRIs are effective in only half of patients and typically take several weeks to relieve symptoms. The NMDA receptor antagonist ketamine exerts a rapid antidepressant action, but has troubling side-effects. In the present disclosure it was considered that partial inverse benzodiazepine agonists would exert similar effects on brain activity as ketamine, but would not exert as many side effects if targeted only to $GABA_A$ receptors containing alpha5 subunits, which are enriched in the hippocampus and prefrontal cortex. In the present disclosure it is shown that the alpha5-selective inverse agonist L-655,708 reversed the alterations in hedonic behavior in the sucrose preference and social interaction tests produced by two different chronic stress paradigms in rats within 24 hrs of systemic administration. L-655,708 had no effect on hedonic behavior in unstressed animals. L-655,708 injection also restored within 24 hrs the strength of pathologically weakened excitatory synaptic transmission at the stress-sensitive temporoammonic-CA1 synapse, measured electrophysiologically, and increased levels of GluA1 subunit of the AMPA receptor, measured with Western blotting. In specific embodiments, the ability of L-655,708 to restore excitatory synaptic strength rapidly underlies its ability to restore stress-induced behavioral alterations rapidly, supporting evidence that dysfunction of multiple excitatory synapses in cortico-mesolimbic reward pathways contributes, in part, to the genesis of depression. Partial inverse agonists of the benzodiazepine receptor site of α5 subunit-containing $GABA_A$ receptors are useful as rapidly acting and clinically viable antidepressant compounds.

Introduction

The present standard of care for treating major depressive disorder is to increase the concentration of monoamine neurotransmitters by inhibiting their reuptake with medications such as selective serotonin reuptake inhibitors (SSRIs). SSRIs are fully effective in only half of depressed patients (Gaynes and Warden, 2009), however. In addition, the 3-8 week latency to achieve a therapeutic effect complicates optimization of medication and delays symptomatic relief. More effective and faster acting therapies are clearly needed to reduce the socioeconomic burden of this debilitating condition.

The discovery that inhibitors of NMDA-type glutamate receptors (NMDARs), such as ketamine, exert a rapid antidepressant action (Trullas and Skolnick, 1990; Berman et al., 2000; Zarate et al., 2006) has triggered a reevaluation of the causes of depression and potential targets for antidepressants. Unfortunately, there are concerns that ketamine's addictive and psychotomimetic properties will hinder it from reaching its potential to treat human depression (Machado-Vieira et al., 2009). Ketamine also produces a rapid antidepressant-like behavioral response in rodents subjected to chronic stress (Maeng et al., 2008; Autry et al., 2011; Li et al., 2010; 2011). This has provided critical mechanistic insights into how rapid antidepressant actions may be produced and raised hopes that new drugs can be developed that target the same effector mechanisms, without ketamine's disadvantages.

A common element linking the therapeutic actions of antidepressants, including SSRIs (Cai et al., 2013), ketamine (Pittenger and Duman, 2008; Kavalali and Monteggia, 2012; Abdallah et al., 2014), and scopolamine (Voleti et al., 2013), is their shared effects on excitatory synapses in cortico-mesolimbic reward circuits. Chronic stress produces depression-like changes in behavior as well as deleterious effects on excitatory synaptic structure and function in multiple brain regions that are associated with cognition, reward, and mood, including the hippocampus (McEwen, 2000; Kallarackal et al., 2013), prefrontal cortex (PFC) (Yuen et al., 2012; Pittenger and Duman, 2008), and nucleus accumbens (NAc) (Lim et al., 2012). Conversely, ketamine, serotonin, and SSRIs promote excitatory synaptic transmission and reverse the effects of chronic stress in these same areas (Pittenger and Duman, 2008; Li et al., 2010; Autry et al., 2011; Cai et al., 2013).

Although the mechanisms underlying ketamine's rapid antidepressant action remain under active investigation, one hypothesis is that it suppresses NMDAR-mediated excitation of inhibitory interneurons (Moghaddam et al., 1997; Farber et al., 1998; Homayoun and Moghaddam, 2007; Abdallah et al., 2014; cf. however: Autry et al., 2011). This results in a mild disinhibition of the neuronal population. Presumably because of this increase in network activity, a brief period of ketamine administration triggers several activity-dependent processes, such as induction of long-term potentiation, increased expression of the immediate early gene deltaFosB, and altered activity of the mTOR and/or eEF2 signaling pathways. This ultimately leads to the rapid induction of synapse-related genes, increased synthesis of synaptic proteins (Li et al., 2010; Autry et al., 2011), restoration of normal synaptic strength, and persistent amelioration of depressive signs and symptoms. These results indicate that it is ultimately the mild increase in activity in forebrain neural circuits that is the key mechanism via which ketamine exerts its rapid therapeutic antidepressant actions.

Based on this consideration, the inventors sought to identify other compounds that could trigger mild increases in neuronal activity, like ketamine. Partial inverse agonists at the benzodiazepine site of γ-aminobutyric acid type-A receptors ($GABA_A$Rs) are negative allosteric modulators that have been shown to promote coherent network activity (Hajos et al., 2004). $GABA_A$Rs containing the α5 subunit are exclusively expressed by prefrontal cortical neurons and hippocampal pyramidal cells, offering the means for selectively targeting cortical inputs to mesolimbic circuits, thereby minimizing psychotomimetic and sedative side effects. L-655,708 is one such partial inverse agonist of $GABA_A$R benzodiazepine sites with a 10-100 fold selectivity for $GABA_A$Rs containing the alpha5 subunit (Atack et al., 2005; 2006). alpha5-selective inverse agonists of the benzodiazepine site are not epileptogenic, hallucinogenic, or anxiogenic in humans (Atack et al., 2009).

It was considered that L-655,708 would exert a rapid antidepressant action via convergence on ketamine's downstream effector mechanisms, and therefore predicted that a single treatment of L-655,708 would rapidly (<24 hrs) reverse chronic stress-induced changes in both hedonic behavior and excitatory synaptic transmission at the archetypical stress-sensitive synapse between temporoammonic (TA) afferents and the distal dendrites of CA1 pyramidal cells.

Materials and Methods

Chronic restraint stress (CRS). Male Sprague Dawley rats (4-5 weeks-old; Harlan Laboratories) were placed in appropriately sized restraint tubes, highly restricting their movement for periods of four hours in a brightly lit lab, every day for ten days during the light phase of their diurnal cycle (Lim et al., 2012).

Chronic unpredictable stress (CUS). Male Sprague-Dawley rats (4-5 weeks-old; Harlan Laboratories) were randomly divided into control and CUS groups. Rats in the CUS group were individually housed. CUS animals were treated with two mild stressors every day for 5-6 weeks during their light phase (Willner et al., 1987). The stressors were randomly cycled to enhance unpredictability. The stressors were: forced swim, in which rats were placed in a basin containing cold water for 5 minutes; strobe lighting, in otherwise total darkness for 30 minutes; restraint, during which rats were put into appropriately sized restraint tubes for 30 minutes; exposure to white noise for 30 minutes; and food or water deprivation for 14 hours spanning the dark phase.

Sucrose preference test (SPT). Rats were given a choice between two bottles containing tap water or a 1% sucrose solution (Rygula et al., 2006). Testing was conducted overnight (16 hours), including the full duration of their dark phase. Animals were first trained with both bottles while group-housed. For subsequent tests, including during the baseline period, animals were individually housed. Sucrose preference was calculated as amount of the sucrose solution consumed as a percentage of the total amount of liquid consumed. For determining the effects of L-655,708, only unstressed rats that demonstrated a sucrose preference >75% at baseline were used.

Social interaction test (SIT). As described previously (Berton et al., 2006), rats were placed in a plastic enclosure (82×82 cm) with a 5×5 grid of squares (16.4×16.4 cm) visible underneath the clear plastic flooring. A small translucent perforated plastic box (20×16 cm) was placed against the center of one wall of the arena. During the testing conditions white overhead fluorescent lighting was used to illuminate the arena. A video camera positioned 170 cm above the floor of the arena was used to track the movements of the rats during the experiment.

Each test consisted of a "target-absent" trial followed by a "target-present" trial. During testing, an individual test rat was placed in the center of the arena and, after 30s of adaptation, the rat's movements were recorded with the video camera for 2.5 minutes. After the "target-absent" trial, the test rat was removed from the arena and placed back in its home cage. For the "target-present" trial, a novel juvenile (3-6 weeks old; always younger than the rat being tested) rat was placed in the internal box at one end of the arena and, after three minutes, the test rat was returned to the center of the arena and filmed for 2.5 minutes. Both rats were removed and the testing arena and internal box were cleaned with 70% ethanol before the next rat was tested. No test rat ever encountered the same target rat more than once.

Results were quantified as the percentage of time spent in the "interaction zone" (the five grid squares immediately surrounding the plastic cage) as measured for both the "target-absent" and "target-present" trials. These percentages were then used to calculate an interaction ratio, which is the percent time spent in the "interaction zone" during the "target-present" trial divided by that of the "target-absent".

Acute slice electrophysiology. Standard methods were used to prepare 400-μm-thick transverse hippocampal slices. Dissection and recording saline contained: 124 mM NaCl, 3 mM KCl, 1.25 mM $NaH_2PO_4$, 1.5 mM $MgSO_4$, 2.5 mM $CaCl_2$, 26 mM $NaHCO_3$, and 10 mM glucose, bubbled with 95% $O_2$/5% $CO_2$. Slices were then transferred to a submersion-type recording chamber and perfused at 0.5 2 ml/min at 20-22° C. Picrotoxin (100 μM) and CGP52432 (2 μM) were included to block $GABA_A$ and $GABA_B$ receptors, and the CA3 region was removed with a scalpel. Because TA-CA1 synapses are electrotonically remote from CA1 cell somata, extracellular recording of local field excitatory postsynaptic potentials (fEPSPs) was used. Recording pipettes (3-5 MSΩ) contained extracellular saline and were placed in stratum lacunosum-moleculare (SLM) to record TA-CA1 responses. fEPSPs were amplified 1000×, filtered at 3 kHz, and digitized at 10 kHz. Concentric bipolar tungsten electrodes were placed >500 μm from the stimulating electrodes in SLM for TA afferents. Stimuli (100 μs) were delivered at 0.05 Hz.

As in previous work (Kallarackal et al., 2013), $Mg^{2+}$-free saline was used to produce a robust NMDAR-mediated component of the fEPSP for quantification of AMPAR-mediated synaptic excitation. 3-5 consecutive responses were averaged and fEPSP slope was calculated over a 1-3 ms window. For AMPAR-mediated responses, the window was fixed in the initial rising phase of the response, 2-5 ms after its initiation. For NMDA responses, DNQX (50 μM) was bath applied for 15 min and the slope was calculated over a 3-5 ms window in the rising phase of the response, 5-10 ms after its initiation.

Responses were elicited over a range of stimulation intensities before and after application of DNQX. Responses were first compared across slices by normalizing them to the amplitude of the fiber volley. The linear portion of the relationship between response slope and FV amplitude was fit with a straight line and the slopes of the fitted lines were compared across conditions, as has been done previously (Kallarackal et al., 2013). The inventors also normalized the slope of AMPAR-mediated responses to the slope of the NMDAR-mediated response, choosing traces that had a fiber volley closest to 0.2 mV in amplitude.

Western blotting. SLM tissue punches (1 mm diameter) were dissected from area CA1 in hippocampal slices and pooled (3-4 punches/sample). Membranes were probed with antibodies directed against GluA1 (Millipore Bioscience Research Reagents) and β-actin (Cell Signaling Technology). Levels of proteins are expressed as the ratio of intensity normalized to β-actin intensity, as done previously (Kallarackal et al., 2013).

Drugs/stats. L-655,708 was purchased from Tocris Bioscience (R&D Systems, Minneapolis, Minn.) and prepared at a concentration of 5 mM in 75% saline/25% DMSO. The dose used in this study (0.7 mg/kg i.p.) was taken from the study of Martin et al (2009), in which L-655,708 was shown to reverse the amnestic properties of the anesthetic etomidate; a positive sign of its efficacy in brain. This dose is sufficient to occupy about 70% of forebrain binding sites (Atack et al., 2005)

All quantification and analyses of behavioral, electrophysiological, and Western blotting results were performed with the experimenter blinded to the condition of the animal, tissue, or protein sample. Data were first compared with an analysis of variance, followed by pairwise post-hoc comparison tests using SPSS software.

Exemplary Results

Rapid Reversal of Stress-Induced Changes in Hedonic Behavior by L-655,708

Figures 6A, 6B:
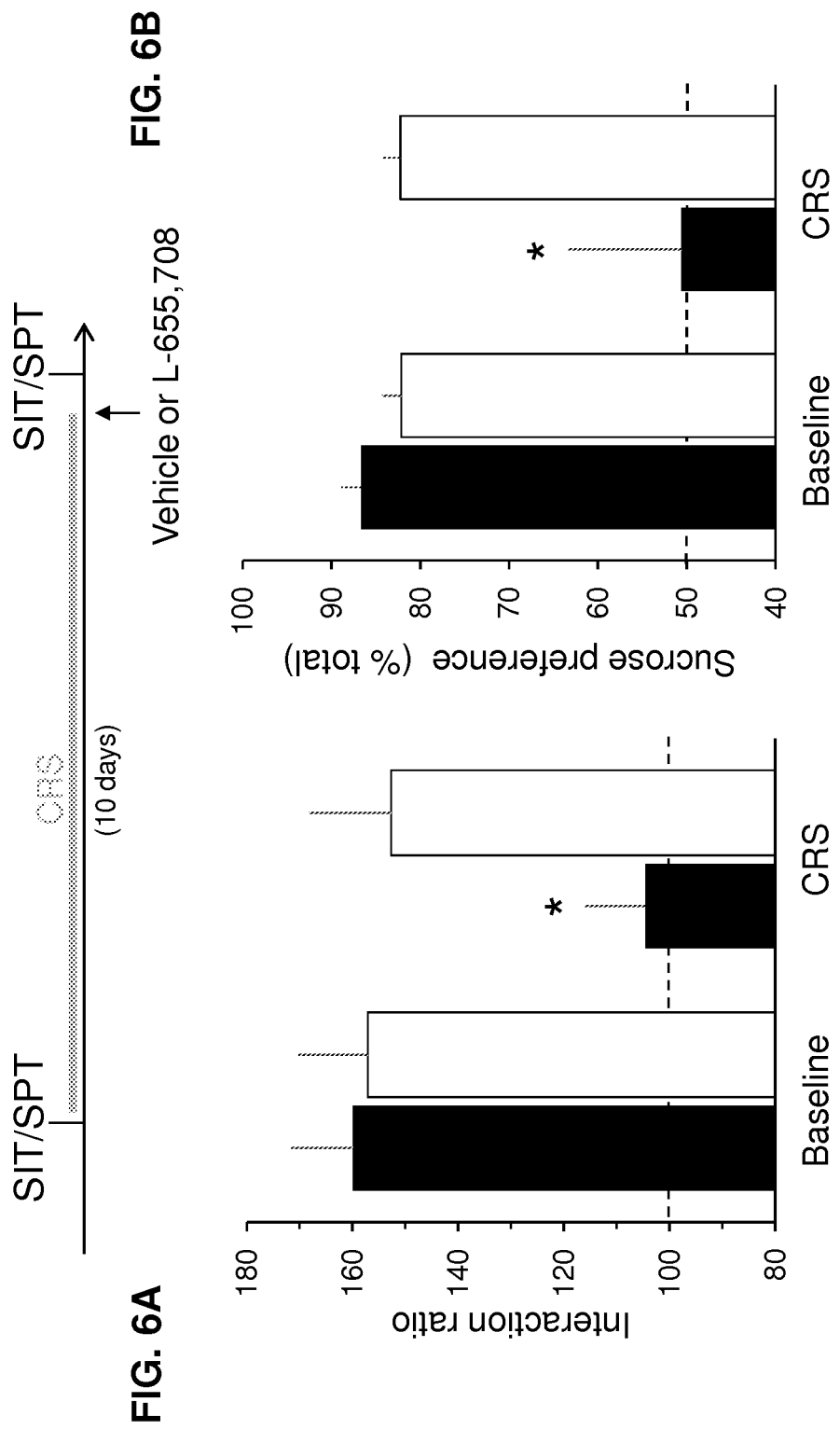
FIGS. 6A and 6B. L-655,708 rapidly reverses loss of sucrose preference and social interaction behaviors after chronic restraint stress. Quantification of results from the sucrose preference test (SPT, FIG. 6A) and the social interaction tests (SIT, FIG. 6B) at two time points: before CRS and after 10 days of CRS. 24 hrs prior to the second round of tests, rats received an injection of either vehicle (black, left bar in pairs of bars; vehicle) or L-655,708 (white, right bar in pairs of bars; L-655,708). Mean sucrose preference differed significantly following vehicle injection compared with all other groups (2×2 repeated-measures ANOVA group-time interaction $F(1,11)=7.514$, $p=0.019$; *, $p<0.05$ compared to pre-CUS baseline, Bonferroni post-hoc test; n=7 CRS+vehicle rats, 6 CRS+L-655,708 rats). Mean social interaction ratios differed significantly following vehicle injection compared with all other groups ($F(1,12)=2.85$, $p=0.115$; n=7 CRS+vehicle rats, 7 CRS+L-655,708 rats).

Several hedonic behaviors in rodents are sensitive to chronic stress and are restored by chronic, but not acute, administration of SSRIs, providing one means to screen for potential antidepressant compounds. First, it was determined whether L-655,708 would rapidly (<24 hrs) restore normal hedonic behavior following chronic restraint stress (Watanabe et al., 1992; Lim et al., 2012), consistent with the rapid antidepressant-like actions of ketamine (Li et al., 2011). Baseline measurements were first made of social interaction and sucrose preference, and then 4-5 week old rats were subjected to ten days of CRS. At the culmination of CRS treatment, rats were injected with either vehicle (75% saline, 25% DMSO; i.p.) or L-655,708 (0.7 mg/kg, i.p.). Social interaction and sucrose preference tests were then repeated 24 hrs post-injection. Chronic restraint stress produced a decrease in social interaction ratio in vehicle-injected CRS rats compared to all other groups, whereas the social interaction ratio in the L-655,708 injected rats was not significantly different than baseline ($F(1,12)=2.85$, $p=0.115$; $n=7$ vehicle-injected, 7 L-655,708 injected) (FIG. 6A). Similarly, there was a significant decrease in sucrose preference in rats that received a vehicle injection compared to their pre-stress baseline, whereas stressed rats administered L-655,708 showed levels of sucrose preference that were not different from their pre-stress baseline (2×2 repeated-measures ANOVA: $F(1,11)=7.514$, $p=0.019$) (FIG. 6B). These behavioral changes are consistent with previous descriptions of chronic SSRIs (Cai et al., 2013) and acute ketamine (Li et al., 2011).

In order to determine if the rapid reversal of stress-induced changes in behavior by L-655,708 was specific to the CRS procedures, these experiments were repeated using another chronic psychological stress paradigm, chronic unpredictable stress (CUS) (Willner et al., 1987). Social interaction tests were conducted at three sequential time points (FIG. 7): before CUS (baseline), after 4 weeks of CUS and an injection of the vehicle solution 24 hrs earlier, and after an additional week of CUS and an injection of L-655,708 24 hrs earlier (0.7 mg/kg, i.p.). The mean social interaction ratio was significantly lower in rats subjected to CUS that were given a vehicle injection compared to both baseline and unstressed rats (3×2 repeated-measures ANOVA group-time interaction: $F(2,50)=6.538$, $p=0.005$; $n=18$ CUS, 9 unstressed rats) (FIG. 10A), consistent with previous descriptions of stress-induced behavioral changes (Berton et al., 2006). 24 hrs after a single injection of L-655,708, social interaction in 14 of 18 CUS rats were reversed to levels that were not significantly different than pre-stress baseline or responses in unstressed animals (FIG. 7B, black symbols). The four CUS rats injected with L-655,708 that failed to display an increase in social interaction appeared largely resilient to the CUS procedures (FIG. 7B, gray symbols).

Figure 12A:
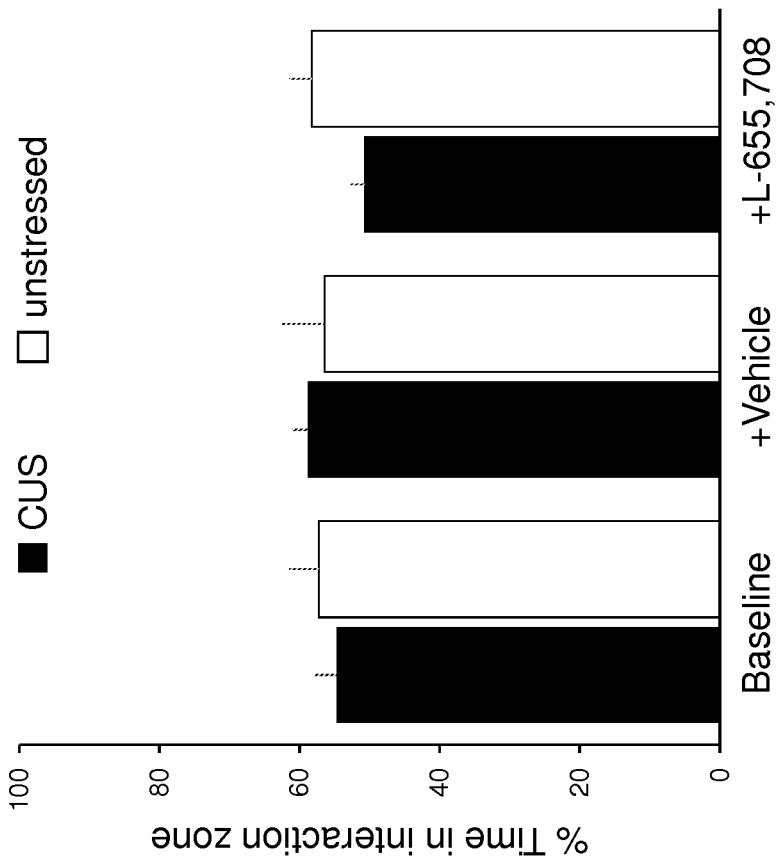
FIGS. 12A and 12B. Neither stress nor L-655,708 injection affect time in the interaction zone in the target absent condition.
Figure 12B:
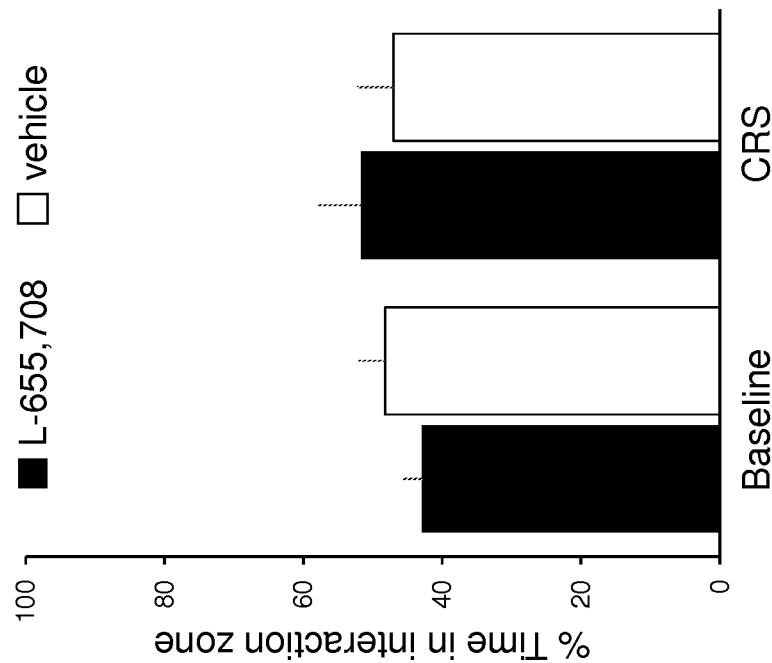

L-655,708 had no significant effect on the time rats spent in the interaction zone in the target absent condition after either CUS ($F(2,23)=1.484$, $p=0.248$) or CRS ($F(1,10)=0.971$, $p=0.348$), as well as in unstressed animals, indicating that it did not induce lasting, nonspecific effects on locomotor behavior that could account for its effects on the social interaction ratio (FIG. 12).

Unstressed rats displayed no change in either sucrose preference or social interaction 24 hrs after injection with either L-655,708 or saline (FIGS. 7C and 7D).

Taken together, these data show that L-655,708 reversed chronic stress-induced depressive-like behavioral changes in less than 24 hrs in a model-independent manner. L-655,708 administration produced no change in the behavior of unstressed animals in these tests.

Rapid reversal of stress-induced weakening of excitatory synaptic transmission by L-655,708

Chronic stress induces a reduction in excitatory synaptic transmission in many cortico-mesolimbic nuclei, including TA-CA1 synapses in the hippocampus (Kallarackal et al., 2013). Chronic, but not acute, administration of fluoxetine restores their strength with a time course that is comparable with behavioral restoration (Cai et al., 2013). Therefore, TA-CA1 synaptic transmission was examined to ask whether L-655,708 would reverse a stress-induced synaptic phenotype as rapidly as it reversed stress-induced behavioral changes.

The inventors used extracellular electrophysiological recording of fEPSPs at TA-CA1 synapses in SLM of area CA1 in brain slices prepared from unstressed rats, rats subjected to ten days of CRS and given a vehicle injection 24 hrs earlier, and rats subjected to ten days of CRS and given an L-655,708 injection 24 hrs earlier (0.7 mg/kg, i.p.). These were the same rats used for the behavioral analyses in FIG. 6. fEPSPs were recorded in ACSF lacking added $Mg^{2+}$ so as to unblock NMDA receptors. The slope was first quantified of the AMPAR component of the fEPSP elicited over a range of stimulation intensities as a function of the amplitude of the fiber volley (FV), a measure of the number of synapses activated. DNQX was then applied to block AMPAR-mediated transmission and elicited a series of NMDAR-mediated responses over the same range of stimulation intensities, as in a previous study (Kallarackal et al., 2013).

There was a decrease in the slope of the AMPAR-mediated component of the fEPSP across all stimulation intensities in slices from rats subjected to CRS and given a vehicle injection, compared to slices from unstressed rats and slices from rats subjected to CRS and given an L-655,708 injection (One-way ANOVA: $F(2,17)$, 3.675, $p=0.047$; $n=5$ unstressed, 8 CRS+vehicle, 7 CRS+L-655,708) (FIGS. 10A and 10B). There was no corresponding difference in the slope of the NMDA component of the fEPSP under these conditions ($F(2,17)$, 0.549, $p=0.588$) (FIGS. 10A and 10B). An AMPA:NMDA ratio was computed for each slice using the slope of the response elicited when the FV was ca. 0.2 mV in amplitude before and after application of DNQX. The AMPA:NMDA ratio was significantly higher in slices from CRS rats injected with L-655,708 24 hrs earlier, compared to vehicle-treated animals subjected to CRS ($p<0.05$ LSD post-hoc), and was not different than responses in tissue from unstressed rats (One-way ANOVA: $F(2,17)$, 4.345, $p=0.03$) (FIG. 10C).

These results replicate the earlier observations that AMPAR-mediated signaling, but not NMDAR-mediated signaling, is impaired by chronic stress at TA-CA1 synapses and it is now demonstrated that this impairment can be reversed rapidly by treatment with L-655,708. The behavioral antidepressant efficacy of L-655,708 is associated with a restoration of excitatory neurotransmission at this stress-sensitive synapse.

Rapid reversal of stress-induced downregulation of GluA1 expression by L-655,708

Restoration of stress-impaired AMPAR-mediated transmission produced by treatment with either chronic SSRIs (Kallarackal et al., 2013) or ketamine (Li et al., 2011) is associated with an increase in the expression of the GluA1 subunit of the AMPAR. It was considered whether L-655,708 would also restore GluA1 expression as rapidly as it reverses the stress-induced behavioral and synaptic phenotypes.

Figure 11A:
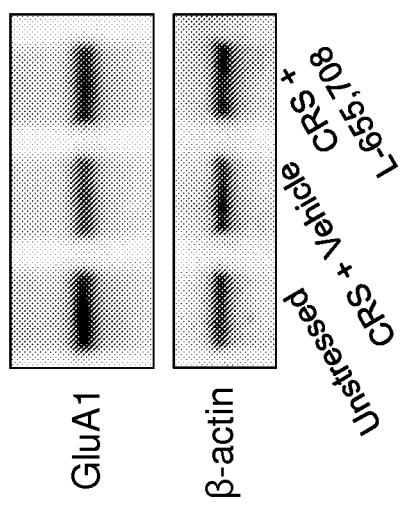
FIGS. 11A and 11B. L-655,708 rapidly reverses stress-induced decreases in GluA1 expression at TA-CA1 synapses of the rat hippocampus.
Figure 11B:
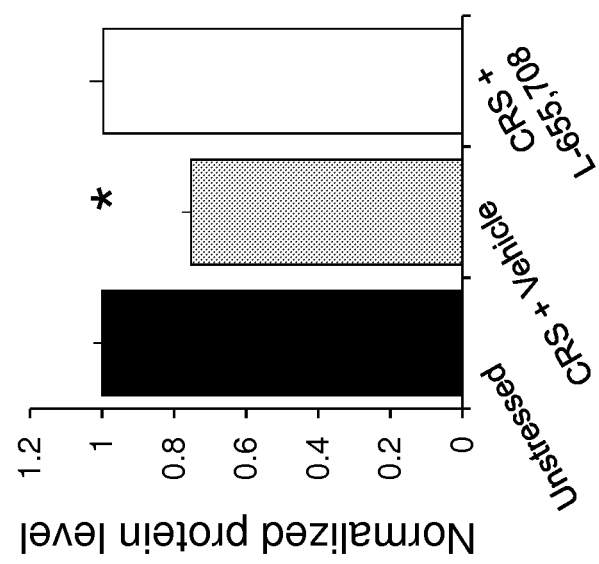

SLM tissue was harvested from slices taken from unstressed rats, rats subjected to ten days of CRS and given a vehicle injection 24 hrs earlier, and rats subjected to ten days of CRS and given an injection of L-655,708 24 hrs earlier (0.7 mg/kg, i.p.). These were the same rats used for FIG. 6. As reported previously for CUS, rats subjected to CRS and injected with vehicle displayed a significantly lower level of GluA1 protein in SLM as compared to unstressed control rats (Kruskal-Wallis H test: $\chi2(2)=10.62$, p=0.0049; n=6 unstressed rats, 6 CRS+vehicle, 8 CRS+L-655,708) (FIG. 11). In contrast, stressed rats injected with L-655,708 24 hrs earlier displayed levels of GluA1 in that were not significantly different than levels in unstressed controls.

These results demonstrate that the stress-induced decrease in GluA1 protein expression, which is correlated with both weakened excitatory synaptic transmission at TA-CA1 synapses and altered hedonic behaviors, is reversed rapidly by treatment with L-655,708. The $\alpha5$ subunit-selective inverse benzodiazepine agonist L-655,708 thus displays antidepressant efficacy at behavioral, electrophysiological, and molecular endpoints.

Significance of Certain Embodiments

It is described herein that L-655,708, a partial inverse agonist at the benzodiazepine site of the $GABA_AR$ that is highly selective for receptors containing alpha5 subunits, reverses the behavioral and synaptic phenotypes produced by two different chronic stress paradigms within 24 hrs of a single systemic administration.

The motivated, appetitive behaviors assayed in the social interaction and sucrose preference tests assay the hedonic properties of two distinct stimuli, food and sociality. In both the sucrose preference and social interaction tests, rats must respond in an active manner to display the high levels of sucrose preference and social interaction that are normally observed. Chronic stress is known to decrease the rewarding properties of a variety of natural and unnatural stimuli in rodents, including their high preference for palatable sucrose-containing solution (Pothion et al., 2004) and the naturally rewarding value of social interactions (Berton et al., 2006). The loss of the rewarding properties of these stimuli is considered to be analogous to anhedonia, or the inability to experience reward, a core symptom of human depression. Importantly, normal behavior in both the sucrose preference test (Rygula et al., 2006) and social interaction test (Berton et al., 2006) are restored with chronic, but not acute, administration of SSRIs, thus providing a strong predictive indication of the potential human antidepressant efficacy of L-655,078 or other alpha5-selective inverse agonists of the benzodiazepine site.

alpha5-containing $GABA_A$ receptors as an antidepressant drug target. $GABA_A$ receptors are heteropentameric ion channels, most commonly containing alpha, beta, and gamma subunits in a 2:2:1 stoichiometry (Sieghart and Sperk, 2002). The interface between a gamma2 subunit and an $\alpha$ subunit forms the benzodiazepine receptor, a site of allosteric modulation that alters channel gating and $GABA_AR$ function. In addition to benzodiazepine agonists (positive modulators), there are inverse agonists that act at the benzodiazepine site to decrease $GABA_A$ receptor function (negative modulators). The molecular identity of the $\alpha$ subunit in the benzodiazepine receptor site determines its pharmacological profile. $GABA_ARs$ containing $\alpha1$ subunits mediate the sedative and amnestic effects of benzodiazepines preferentially, whereas $GABA_ARs$ containing $\alpha2$ and $\alpha3$ subunits mediate their anxiolytic effects (Rudolph et al., 1999); Mohler et al., 2002). Partial inverse agonists with low affinity for these receptor subtypes offer the potential advantage of a wider therapeutic concentration range and a lower likelihood of producing negative side effects, such as anxiety or epileptiform discharge.

$\alpha5$-subunit mRNA is abundant in pyramidal cells in the hippocampus and deep layers of the neocortex, and $\alpha5$-containing $GABA_ARs$ are localized at synaptic and extrasynaptic sites in the dendrites (Fritschy and Mohler, 1995; Wainwright et al., 2000; Serwanski et al., 2006). $\alpha5$-containing $GABA_ARs$ mediate tonic inhibition (Caraiscos et al., 2004) and lower the excitability of pyramidal cells (Bonin et al., 2006), so negative allosteric modulators of $\alpha5$-containing $GABA_ARs$ should promote coherent activity (Hajos et al., 2004; Towers et al., 2004). Drugs targeting these receptors are thus an attractive means to selectively alter activity within cortico-mesolimbic circuits without altering activity in other circuits. Indeed, deletion of the $\alpha5$ gene alters learning in hippocampal-dependent tasks but not hippocampal-independent ones (Collinson et al., 2002). Interestingly, alpha5 subunits are up-regulated in mice after chronic stress (Matsumoto et al., 2007), suggesting a role for the alpha5 subunit in the cognitive deficits associated with chronic stress and depression, in particular embodiments.

Mechanisms of L-655,708 action. The observation that L-655,708 rapidly restores pathologically weakened AMPAR-mediated excitatory transmission at TA-CA1 synapses of the hippocampus indicates a likely mechanism by which L-655,708 exerts its antidepressant efficacy in behavioral testing. SSRIs (Cai et al., 2013), ketamine (Autry et al., 2011; Li et al., 2010), and L-655,708 all enhance excitatory synaptic strength at multiple sites within the cortico-mesolimbic reward circuitry, thereby providing strong support for an association between the restoration of excitatory synaptic strength and the reversal of depressive behavioral phenotypes (Duman, 2014). TA-CA1 synapses are not uniquely sensitive to stress or responsive to antidepressants, but they do serve as a convenient archetype of stress-induced changes that are likely occurring at many synapses in the cortico-mesolimbic reward circuitry (Lim et al., 2012; Yuen et al., 2012). The net effect of this weakening is likely to be a dysfunction in processing of rewarding stimuli which may underlie common symptoms of depression, such as anhedonia (Nestler and Carlezon, 2006). Restoration of the strength of these synapses by effective antidepressants should restore normal responses to rewarding stimuli (Belujon and Grace, 2014).

Acute administration of ketamine improves mood and reduces depressive symptoms within 1-2 hours in humans and these effects persist for up to two weeks. Similarly, ketamine restores sucrose preference and novelty suppressed feeding behaviors rapidly (24 hrs) in chronically stressed animals (Li et al., 2011). Ketamine's therapeutic effects are induced during the brief period (ca. 1-2 hours) when it is present in the brain at sufficient concentrations to inhibit NMDARs, triggering relief of symptoms that persist for days after it is cleared from the body. During this induction phase, ketamine may preferentially reduce excitation of GABAergic inhibitory interneurons (Dwyer and Duman, 2013; Farber et al., 1998; Homayoun and Moghaddam, 2007), thereby producing a mild disinhibition of the neuronal population and increased activity in the hippocampus, entorhinal cortex, NAc, and PFC, as observed in rodents (e.g. Kittelberger et al., 2012; Middleton et al., 2008; Hunt et al., 2011) and in humans (Cornwell et al., 2012; Driesen et al., 2013). This activity is accompanied by a neurochemically detectable surge of glutamate release in the PFC and NAc (Lorrain et al., 2003; Moghaddam et al., 1997; Razoux et al., 2007). α5-selective benzodiazepine inverse agonists also produce mild disinhibition through their negative allosteric actions, and should therefore also trigger an increased coherence in oscillatory activity, as has been observed following injection of nonselective benzodiazepine inverse agonists (Hajos et al., 2004).

In specific embodiments, the ability of both L-655,708 and ketamine to promote activity accounts for their shared antidepressant efficacy because such activity strengthens excitatory synapses via convergence onto common activity-dependent signaling pathways. Potential activity-dependent processes include an increase in BDNF signaling, activation of mTOR signaling, and protein synthesis (Autry et al., 2011; Li et al., 2010; 2011). An increase in coherent circuit activity is also likely to promote the induction of long-term potentiation (e.g. Huerta and Lisman, 1993). All of these activity-dependent processes have been shown to strengthen excitatory synapses. Indeed, L-655,708 administration triggers a rapid increase in GluA1 protein levels in the distal dendrites of CA1 pyramidal cells, coincident with an increase in AMPAR-mediated synaptic excitation. Interestingly, chronic, but not acute, administration of SSRIs also promotes GluA1 protein levels in this same region (Kallarackal et al., 2013), which is densely innervated with serotonergic terminals.

Therapeutic potential. Because disinhibition promotes induction of long-term potentiation, the presumptive cellular basis of memory, partial inverse agonists of $GABA_A$Rs containing α5 subunits have been developed as cognitive enhancers (Ballard et al., 2009; Quirk et al., 1996; Atack et al., 2006; 2009). Unlike non-selective benzodiazepine inverse agonists, these compounds are not anxiogenic, hallucinogenic, or epileptogenic in humans (Atack et al., 2009).

Although SSRIs are reasonably safe and well tolerated, and are not addictive, they are effective in only a subset of patients and only after a delay of weeks-to-months. Ketamine, on the other hand, exerts a rapid antidepressant action in the majority of patients, but its therapeutic viability is extremely limited to its dissociative and anesthetic properties, as well as its potential for abuse and overdose. L-655,708 reversed stress-induced behavioral changes and restored AMPAR-mediated excitatory synaptic strength in two well-validated rodent models of antidepressant efficacy, like SSRIs and ketamine. Because these effects were induced within 24 hrs of a single systemic injection, in particular embodiments partial inverse agonists of benzodiazepine receptors acting on alpha5-subunit containing $GABA_A$Rs represent a novel, rapidly acting, effective, and clinically viable treatment for human depression.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

REFERENCES

Abdallah C G, Sanacora G, Duman R S, Krystal J H (2014). Ketamine and rapid-acting antidepressants: a window into a new neurobiology for mood disorder therapeutics. *Annu Rev Med*, in press.

Amat J, Aleksejev R M, Paul E, Watkins L R, Maier S F (2010) Behavioral control over shock blocks behavioral and neurochemical effects of later social defeat. Neurosci. 165: 1031-1038.

Atack J R, Alder L, Cook S M, Smith A J, McKernan R M (2005). In vivo labelling of α5 subunit-containing $GABA_A$ receptors using the selective radioligand [3H]L-655,708. *Neuropharmacol* 49: 220-229.

Atack J R, Bayley P J, Seabrook G R, Wafford K A, McKernan R M, Dawson G R (2006). L-655,708 enhances cognition in rats but is not proconvulsant at a dose selective for α5-containing $GABA_A$ receptors. *Neuropharmacol* 51: 1023-1029.

Atack J R, Maubach K A, Wafford K A, O'Connor D, Rodrigues A D, Evans D C, et al (2009). In vitro and in vivo properties of 3-tert-Butyl-7-(5-methylisooxazol-3-yl)-2-(1-methyl-1H-1,2,4-triazol-5-ylmethoxy)-pyrazolo[1,5-d]-[1,2,4] triazine (MRK-016), a $GABA_A$ receptor α5 subtype-selective inverse agonist. *J Pharmacol Exp Therapeutics* 331: 470-484.

Autry A E, Nosyreva E, Na E S, Los M F, Cheng P F, Kavalali E T et al (2011). NMDA receptor blockade at rest triggers rapid behavioral antidepressant responses. *Nature* 475: 91-95.

Ballard T, Knoflach F, Prinssen E, Borroni E, Vivian J A, Basile J et al (2009). RO938581, a novel cognitive enhancer acting at $GABA_A$ α5 subunit-containing receptors. *Psychopharmacol* 202: 207-223.

Belujon P, Grace A A (2014). Restoring mood balance in depression: ketamine reverses deficit in dopamine-dependent synaptic plasticity. *Biol Psychiatry* May 6. pii: S0006-3223(14)00299-6. doi: 10.1016/j.biopsych.2014.04.014.

Berman R M, Cappiello A, Anand A, Oren D A, Heninger G R, Charney D S et al (2000). Antidepressant effects of ketamine in depressed patients. *Biol Psychiatry* 47: 351-54.

Berton O, McClung C A, Dileone R J, Krishnan V, Renthal W, Russo S J et al (2006). Essential role of BDNF in the mesolimbic dopamine pathway in social defeat stress. *Science* 311: 864-868.

Bonin R P, Martin L J, MacDonald J F, Orser B A (2007). α5 GABAA receptors regulate the intrinsic excitability of mouse hippocampal pyramidal neurons. *J Neurophysiol* 98: 2244-2254.

Burgard E C, Tietz E I, Neelands T R, Macdonald R L (1996) Properties of recombinant gamma-aminobutyric acid A receptor isoforms containing the alpha 5 subunit subtype. Mol Pharmacol. 50: 119-127.

Cai X, Kallarackal A J, Kvarta M D, Goluskin S, Gaylor K, Bailey A M et al (2013). Local potentiation of excitatory synapses by serotonin and its alteration in rodent models of depression. *Nature Neuro* 16: 464-472.

Caixeta F V, Cornelio A M, Scheffer-Teixeira R, Ribeiro S, Tort A B L (2013). Ketamine alters oscillatory coupling in the hippocampus. Nature Scientific Reports 3: 2348.

Caraiscos V B, Elliott E M, You-Ten K E, Cheng V Y, Belelli D, Newell J G et al (2004). Tonic inhibition in mouse hippocampal CA1 pyramidal neurons is mediated by α5 subunit-containing γ-aminobutyric acid type A receptors. *Proc Natl Acad Sci USA* 101: 3662-3667.

Chen L, Durkin K A, Casida J E (2006) Structural model for gamma-aminobutyric acid receptor noncompetitive antagonist binding: widely diverse structures fit the same site. Proc Natl Acad Sci USA. 103: 518S-5190.

Collinson N, Kuenzi F M, Jarolimek W, Maubach K A, Cothliff R, Sur C, et al. (2002). Enhanced learning and memory and altered GABAergic synaptic transmission in mice lacking the alpha 5 subunit of the $GABA_A$ receptor. *J Neurosci* 22: 5572-5580.

Cornwell B, Salvadore G, Furey M (2012). Synaptic potentiation is critical for rapid antidepressant response to ketamine in treatment-resistant major depression. *Biological Psychiatry,* 72: 555-561.

Driesen N R, McCarthy G, Bhagwagar Z, Bloch M H, Calhoun V D, D'Souza D C et al (2013). The impact of NMDA receptor blockade on human working memory-related prefrontal function and connectivity. *Neuropsychopharmacol* 38: 2613-2622.

Duman R S, Vaidya V A, Nibuya M, Morinobu S, Rydelek L (1995). Review: Stress, Antidepressant Treatments, and Neurotrophic Factors: Molecular Mechanism. *Neuroscientist* 1: 351.

Duman R S, Voleti B (2012). Signaling pathways underlying the pathophysiology and treatment of depression: novel mechanisms for rapid-acting agents. *Trends Neurosci* 35: 47-56.

Duman R S (2014). Neurobiology of stress, depression and rapid acting antidepressants: remodeling synaptic connections. *Depress Anxiety* 31: 291-296.

Dwyer J M, Duman R S (2013). Activation of mammalian target of rapamycin and synaptogenesis: role in the actions of rapid-acting antidepressants. *Biol Psychiatry,* 73: 1189-1198.

Farber N B, Newcomer J W, Olney J W (1998). The glutamate synapse in neuropsychiatric disorders. Focus on schizophrenia and Alzheimer's disease. *Prog Brain Res* 116: 421-437.

Fritschy J M, Möhler H (1995). $GABA_A$-receptor heterogeneity in the adult rat brain: differential regional and cellular distribution of seven major subunits. *J Comp Neurol* 1359: 154-194.

Gaynes B, Warden D (2009). What did STAR* D teach us? Results from a large-scale, practical, clinical trial for patients with depression. *Psychiatry Serv* 60: 1439-1445.

Hajós M, Hoffmann W E, Orbán G, Kiss T, Erdi P (2004). Modulation of septo-hippocampal theta activity by $GABA_A$ receptors: an experimental and computational approach. *Neurosci* 126: 599-610.

Homayoun H, Moghaddam B (2007). NMDA receptor hypofunction produces opposite effects on prefrontal cortex interneurons and pyramidal neurons. *J Neuroscience* 27: 11496-11500.

Huerta P T, Lisman J E (1993). Heightened synaptic plasticity of hippocampal CA1 neurons during a cholinergically induced rhythmic state. Nature 364: 723-725.

Hunt M J, Falinska M, Leski S, Wójcik D K, Kasicki S (2011). Differential effects produced by ketamine on oscillatory activity recorded in the rat hippocampus, dorsal striatum and nucleus accumbens. J Psychopharmacol 25: 808-821.

Ibrahim L, et al. (2012) Course of Improvement in depressive symptoms to a single intravenous infusion of ketamine vs add-on riluzole: results from a 4-week, double-blind, placebo-controlled study. Neuropsychopharmacol. 37: 1526-1533.

Kallarackal A J, Kvarta M D, Cammarata E, Jaberi L, Cal X, Bailey A M, Thompson S M (2013) Chronic stress induces a selective decrease in AMPA receptor-mediated synaptic excitation at hippocampal temporoammonlc-CA1 synapses. J Neurosci. 33: 15669-15674.

Kavalali E T, Monteggia L M (2012). Synaptic mechanisms underlying rapid antidepressant action of ketamine. Am J Psychiatry 169: 1150-1156.

Kittelberger K, Hur E E, Sazegar S, Keshavan V, Kocsis B (2012). Comparison of the effects of acute and chronic administration of ketamine on hippocampal oscillations: relevance for the NMDA receptor hypofunction model of schizophrenia. Brain Struct Funct 217: 395-409.

Li N, Lee B, Liu R J, Banasr M, Dwyer J M, Iwata M, et al (2010). mTOR-dependent synapse formation underlies the rapid antidepressant effects of NMDA antagonists. Science 329: 959-964.

Li N, Liu R J, Dwyer J M, Banasr M, Lee B, Son H et al (2011). Glutamate N-methyl-D-aspartate receptor antagonists rapidly reverse behavioral and synaptic deficits caused by chronic stress exposure. Biol Psychiatry 69: 754-761.

Lim B K, Huang, K W, Grueter, B A, Rothwell, P E, and Malenka, R C (2012). Anhedonia requires MC4R-mediated synaptic adaptations in nucleus accumbens. Nature 487: 183-189.

Lorrain D S, Baccei C S, Bristow L J, Anderson J J, Varney M A (2003). Effects of ketamine and N-methyl-D-aspartate on glutamate and dopamine release in the rat prefrontal cortex: modulation by a group II selective metabotropic glutamate receptor agonist LY379268. Neurosci 117: 697-706.

Machado-Vieira R, Salvadore G, Diazgranados N, Zarate C A (2009) Ketamine and the next generation of antidepressants with a rapid onset of action. Pharmacal Ther 123: 143-150.

Maeng S, Zarate C A, Du J, Schloesser R J, McCammon J, Chen G et al (2008). Cellular mechanisms underlying the antidepressant effects of ketamine: role of alpha-amino-3-hydroxy-5-methylisoxazole-4-propionic acid receptors. Biological Psychiatry 63: 349-352.

Maguire J, Ferando I, Simonsen C, Mody I (2009) Excitability changes related to GABAA receptor plasticity during pregnancy. J Neurosci 29: 9592-9601.

Martin U, Oh G H, Orser B A (2009). Etomidate targets α5 γ-aminobutyric acid subtype A receptors to regulate synaptic plasticity and memory blockade. Anesthesiol 111: 1025-1035.

Matsumoto K, Puia G, Dong E, Pinna G (2007). GABAA receptor neurotransmission dysfunction in a mouse model of social isolation-induced stress: possible insights into a non-serotonergic mechanism of action of SSRIs in mood and anxiety disorders. Stress 10: 3-12.

McEwen B S (2000). Allostasis and allostatic load: Implications for neuropsychopharmacology. Neuropsychopharmacol 22: 108-124.

Mellon S H, Griffin L D (2002) Neurosteroids: biochemistry and clinical significance. Trends Endocrinol. Metab. 13: 35-43.

Middleton S, Jalics J, Kispersky T, Lebeau F E, Roopun A K, Kopell N J et al (2008). NMDA receptor-dependent switching between different gamma rhythm-generating microcircuits in entorhinal cortex. Proc Natl Acad Sci USA 105: 18572-18577.

Moghaddam B, Adams B, Verma A, DalyD (1997). Activation of glutamatergic neurotransmission by ketamine: A novel step in the pathway from NMDA receptor blockade. J Neurosci 17: 2921-2927.

Mohler H, Fritschy J M, Rudolph U (2002). A new benzodiazepine pharmacology. J Pharmacol Exp Therapeutics 300: 2-8.

Nestler E J, Carlezon W A (2006). The mesolimbic dopamine reward circuit in depression. Biol Psychiatry 59: 1151-1159.

Pinna G, Costa E, Guidotti A (2006) Fluoxetine and norfluoxetine stereospecifically and selectively increase brain neurosteroid content at doses that are inactive on 5-HT reuptake. Psychopharmacol 186: 362-72.

Pittenger C, Duman R S (2008). Stress, depression, and neuroplasticity: a convergence of mechanisms. Neuropsychopharmacol 33: 88-109.

Pothion S, Bizot J-C, Trovero F, Belzung C (2004). Strain differences in sucrose preference and in the consequences of unpredictable chronic mild stress. Behavioural Brain Res 155: 135-146.

Quirk K, Blurton P, Fletcher S, Leeson P, Tang F, Mellilo D et al (1996). [3H]L-655,708, a novel ligand selective for the benzodiazepine site of GABAA receptors which contain the α5 subunit. Neuropharmacol 35: 1331-1335.

Razoux F, Garcia R, Lena I (2007). Ketamine, at a dose that disrupts motor behavior and latent inhibition, enhances prefrontal cortex synaptic efficacy and glutamate release in the nucleus accumbens. Neuropsychopharmacol 32: 719-727.

Rudolph U, Crestani F, Benke D, Briinig I, Benson J A, Fritschy J M et al (1999). Benzodiazepine actions mediated by specific γ-aminobutyric acidA receptor subtypes. Nature 401: 796-800.

Rygula R, Abumaria N, Flugge G, Hiemke C, Fuchs E, Ruther E et al (2006). Citalopram counteracts depressive-like symptoms evoked by chronic social stress in rats. Behav Pharmacol 17: 19-29.

Serwanski D R, Miralles C P, Christie S B, Mehta A K, Li X, De Blas A L (2006). Synaptic and nonsynaptic localization of GABAA receptors containing the α5 subunit in the rat brain. J Comp Neurol 499: 458-470.

Shansky R M, et al. (2004) Estrogen mediates sex differences in stress-induced prefrontal cortex dysfunction. Mol Psychiatry 9: 531-538.

Sieghart W, Sperk G (2002) Subunit composition, distribution and function of GABA(A) receptor subtypes. Curr Top Med Chem 2: 795-816.

Sieghart W, Ramerstorfer J, Sarto-Jackson I, Varagic Z, Ernst M (2012) A novel GABA(A) receptor pharmacology: drugs interacting with the a(+) PH interface. Br J Pharmacol 166:476-485.

Towers S K, Gloveli T, Traub R D, Driver J E, Engel D, Fradley Ret al (2004). Alpha 5 subunit-containing GABAA receptors affect the dynamic range of mouse hippocampal kainate-induced gamma frequency oscillations in vitro. J Physiol 559: 721-728.

Trullas R, Skolnick P (1990). Functional antagonists at the NMDA receptor complex exhibit antidepressant actions. Eur J Pharmacol 18: 1-10.

Yuen E Y, Wei J, Liu W, Zhong P, Li X, Zhen Y (2012). Repeated stress causes cognitive impairment by suppressing glutamate receptor expression and function in prefrontal cortex. Neuron 73: 962-977.

Voleti B, Navarria A, Liu R J, Banasr M, Li N, Terwilliger R, et al (2013). Scopolamine rapidly increases mammalian target of rapamycin complex 1 signaling, synaptogenesis, and antidepressant behavioral responses. Biol Psychiatry 74: 742-749.

Wafford K A (2005) GABAA receptor subtypes: any clues to the mechanism of benzodiazepine dependence? Curr Opin Pharmacol. 5: 47-52.

Wainwright A, Sirinathsinghji D J, Oliver K R (2000) Expression of GABA(A) receptor alpha5 subunit-like immunoreactivity in human hippocampus. Brain Res Mol Brain Res. 80: 228-232.

Watanabe Y, Gould E, McEwen B S (1992) Stress induces atrophy of apical dendrites of hippocampal CA3 pyramidal neurons. Brain Res 588: 341-345.

Willner P, Towell A, Sampson D, Sophokleous S, Muscat R (1987). Reduction of sucrose preference by chronic unpredictable mild stress, and its restoration by a tricyclic antidepressant. Psychopharmacol (Berl) 93: 358-364.

Zarate C A, Singh J B, Carlson P J, Brutsche N E, Ameli R, Luckenbaugh D A et al (2006). A randomized trial of an N-methyl-D-aspartate antagonist in treatment-resistant major depression. Arch Gen Psychiatry 63: 856-864.

Zarate C A, et al. (2012) Replication of ketamine's antidepressant efficacy In bipolar depression: a controlled add-on trial. Bioi Psychiatry. 71:939-946.

What is claimed is:

1. A method of treating or ameliorating at least one symptom of a medical condition in an individual, comprising the step of providing to the individual a therapeutically effective amount of one or more negative modulators of $GABA_A$ receptors, wherein the medical condition is selected from the group consisting of depression having anhedonia as a symptom; major depressive disorder (MDD); suicidality; and a combination thereof, wherein the negative modulator of $GABA_A$ receptor is a partial inverse agonist of a $GABA_A$ receptor comprising an α5 subunit, said modulator selected from the group consisting of ethyl (13aS)-7-methoxy-9-oxo-11,12,13,13 a-terahydro-9H-imidazo[1,5-a]pyrrolo[2,1-c][1,4]benzodiazepine-1-carboxylate (L-655,708), 3-bromo-10-(difluoromethyl)-9H-benzo[f]imidazo[1,5-a][1,2,4]triazolo[1,5-d][1,4]diazepine (RO4938581), N-benzyl-6-ethoxy-4-oxo-1H-1,5-naphthyridine-3-carboxamide (CP-457,920), 3-tert-Butyl-7-(5-methylisoxazol-3-yl)-2-(1-methyl-1H-1,2,4-triazol-5-ylmethoxy)pyrazolo(1,5-d)(1,2,4)triazine (MRK-016), RG-1662, and a combination thereof.

2. The method of claim 1, wherein the onset of amelioration of one or more depression-related symptoms occurs within hours, days, or weeks.

3. The method of claim 1, wherein the individual has been diagnosed with the medical condition.

4. The method of claim 1, wherein the partial inverse agonist is L-655,708.

5. The method of claim 1, further comprising the step of providing to the individual a therapeutically effective amount of another therapy.

6. The method of claim 5, wherein the other therapy is selected from the group consisting of monoamine oxidase inhibitors (MAOis), selective serotonin reuptake inhibitors (SSRis), serotonin-norepinephrine reuptake inhibitors (SN-Ris), norepinephrine reuptake inhibitors (NRIs), triple reuptake inhibitors, modulators of CNS acetylcholine function, stimulants, anti-glucocorticoids, antagonists of NMDA-type glutamate receptors, tricylic antidepressants (TCAs), and a combination thereof.

7. The method of claim , wherein the other therapy is an anti-depressant.

8. The method of claim 1, wherein the medical condition is suicidality.

9. The method of claim 1, wherein the medical condition is depression having anhedonia as a symptom or suicidality.

10. The method of claim 1, wherein the medical condition is MDD or suicidality.

11. The method of claim 1, wherein the medical condition is depression having anhedonia as a symptom or MDD.

\* \* \* \* \*